United States Patent
Voss et al.

(10) Patent No.: US 10,829,446 B2
(45) Date of Patent: Nov. 10, 2020

(54) ARYL SULFONOHYDRAZIDES

(71) Applicants: MONASH UNIVERSITY, Clayton, Victoria (AU); The Walter and Eliza Hall Institute of Medical Research, Parkville, Victoria (AU)

(72) Inventors: Anne Kathrin Voss, Parkville (AU); Jonathan Baell, Parkville (AU); Huu Nghi Nguyen, Parkville (AU); David J. Leaver, Parkville (AU); Benjamin L. Cleary, Parkville (AU); H. Rachel Lagiakos, Parkville (AU); Bilal Nadeem Sheikh, Parkville (AU); Timothy John Thomas, Parkville (AU)

(73) Assignees: MONASH UNIVERSITY, Clayton (AU); The Walter and Eliza Hall Institute of Medical Research, Parkville (AU)

( * ) Notice: Subject to any disclaimer, the term of this patent is extended or adjusted under 35 U.S.C. 154(b) by 0 days.

(21) Appl. No.: 15/579,964

(22) PCT Filed: Jun. 9, 2016

(86) PCT No.: PCT/EP2016/063125
§ 371 (c)(1),
(2) Date: Dec. 6, 2017

(87) PCT Pub. No.: WO2016/198507
PCT Pub. Date: Dec. 15, 2016

(65) Prior Publication Data
US 2018/0222857 A1    Aug. 9, 2018

(30) Foreign Application Priority Data
Jun. 9, 2015   (GB) .................................. 1510019.1

(51) Int. Cl.
C07C 311/49        (2006.01)
C07D 231/12        (2006.01)
(Continued)

(52) U.S. Cl.
CPC ............. *C07C 311/49* (2013.01); *A61P 35/00* (2018.01); *C07D 213/56* (2013.01);
(Continued)

(58) Field of Classification Search
None
See application file for complete search history.

(56) References Cited

FOREIGN PATENT DOCUMENTS

EP        0 185 387 A1    6/1986

OTHER PUBLICATIONS

CAS registry file RN 901065-47-2 (entered STN Aug. 14, 2006) (Year: 2006).*
(Continued)

*Primary Examiner* — Amy C Bonaparte
(74) *Attorney, Agent, or Firm* — Faegre Drinker Biddle & Reath LLP

(57) ABSTRACT

Compound of formula I:

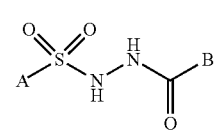

(I)

wherein:
A is selected from:
(i)

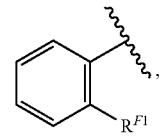

where $R^{F1}$ is H or F;
(ii)

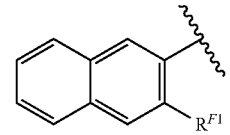

(iii) a N-containing $C_6$ heteroaryl group; and
B is

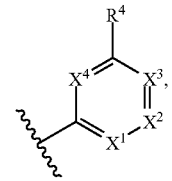

where $X^1$ is either $CR^{F2}$ or N, where $R^{F2}$ is H or F; $X^2$ is either $CR^3$ or N, where $R^3$ is selected from H, Me, Cl, F OMe; $X^3$ is either CH or N; $X^4$ is either $CR^{F3}$ or N, where $R^{F3}$ is H or F; where only one or two of $X^1$, $X^2$, $X^3$ and $X^4$ may be N; and
$R^4$ is selected from I, optionally substituted phenyl, optionally substituted $C_{5-6}$ heteroaryl; optionally substituted $C_{1-6}$ alkyl and optionally substituted $C_{1-6}$ alkoxy, which are useful in the treatment of a condition ameliorated by the inhibition of MOZ.

18 Claims, No Drawings

(51) Int. Cl.
    C07D 271/10    (2006.01)
    C07D 213/86    (2006.01)
    C07D 271/06    (2006.01)
    C07D 239/26    (2006.01)
    C07D 213/87    (2006.01)
    C07D 307/54    (2006.01)
    C07D 249/06    (2006.01)
    C07D 277/30    (2006.01)
    C07D 231/16    (2006.01)
    C07D 213/56    (2006.01)
    C07D 333/24    (2006.01)
    C07D 237/08    (2006.01)
    A61P 35/00     (2006.01)

(52) U.S. Cl.
    CPC ......... *C07D 213/86* (2013.01); *C07D 213/87* (2013.01); *C07D 231/12* (2013.01); *C07D 231/16* (2013.01); *C07D 237/08* (2013.01); *C07D 239/26* (2013.01); *C07D 249/06* (2013.01); *C07D 271/06* (2013.01); *C07D 271/10* (2013.01); *C07D 277/30* (2013.01); *C07D 307/54* (2013.01); *C07D 333/24* (2013.01); *C07C 2601/02* (2017.05); *C07C 2601/08* (2017.05); *C07C 2601/16* (2017.05); *C07C 2602/10* (2017.05)

(56) References Cited

OTHER PUBLICATIONS

CAS Registry file RN 1013283-16-3 (entered STN Apr. 9, 2008) (Year: 2008).*
Koruncev ("2-Ethylpyridine Derivatives with Antitubercular Properties", Journal of Pharmaceutical Sciences, 1974, 63(3), p. 475-477) (Year: 1974).*
RN 1015385-05-3 (entered STN Apr. 17, 2008). (Year: 2008).*
Sheik ("MOZ regulates B-cell progenitors and, consequently, Moz haploinsufficiency dramatically retards MYC-induced lymphoma development" Blood, 2015, 125, p. 1910-1921) (Year: 2015).*
Database Registry [Online] Chemical Abstracts Service, Columbus, Ohio, US; Apr. 9, 2008, XP-002761557, Database accession No. 1013283-16-3, 1 page.
Database Registry [Online] Chemical Abstracts Service, Columbus, Ohio, US; Aug. 14, 2006, XP-002761558, Database accession No. 901065-47-2, 1 page.
Database Registry [Online] Chemical Abstracts Service, Columbus, Ohio, US; Aug. 4, 2006, XP-002761559, Database accession No. 901050-46-2, 1 page.
Database Registry [Online] Chemical Abstracts Service, Columbus, Ohio, US; Dec. 1, 2003, XP-002761560, Database accession No. 622342-37-4, 1 page.
Database Registry [Online] Chemical Abstracts Service, Columbus, Ohio, US; Sep. 15, 2003, XP-002761561, Database accession No. 585565-13-5, 1 page.
Database Registry [Online] Chemical Abstracts Service, Columbus, Ohio, US; Apr. 26, 2001, XP-002761562, Database accession No. 332942-38-8, 1 page.
Database Registry [Online] Chemical Abstracts Service, Columbus, Ohio, US; Aug. 14, 2002, XP-002761563, Database accession No. 443896-79-5, 1 page.
Database Registry [Online] Chemical Abstracts Service, Columbus, Ohio, US; Aug. 16, 2002, XP-002761564, Database accession No. 444082-25-1, 1 page.
Pekhtereva, T.M. et al., "The effect of N-substituents on the chemical shifts and spin-spin coupling contants of the HNNH group in benzenesulfonylhydrazine derivatives, (XP-002761565)," retrieved from STN Database accession No. 1990:477558, Database Registry [Online] Chemical Abstracts Service, Columbus, Ohio, US; 1990, 4 pages.
Falk, H., et al., "An Efficient High-Throughput Screening Method for MYST Family Acetyltransferases, a New Class of Epigenetic Drug Targets," Journal of Biomolecular Screening, vol. 16, No. 10, Nov. 14, 2011, pp. 1196-1205.
Jones, D. H., et al., "Antiviral Chemotherapy. I. The Activity of Pyridine and Quinoline Derivatives against Neurovaccinia in Mice," Journal of Medicinal Chemistry, American Chemical Society, US, vol. 8, Sep. 1, 1965, pp. 676-680.
Mukherjee, J., et al., "Synthesis of 6,8-Dimethoxysocoumarin-3-carboxylic Acid," Indian Journal of Chemistry. Section B, Council of Scientific and Industrial Research (C S I R), IN, vol. 13, No. 8 1975, pp. 859-860.
International Search Report dated Sep. 20, 2016 for PCT/EP2016/063125.
Written Opinion dated Sep. 20, 2016 for PCT/EP2016/063125.

* cited by examiner

ARYL SULFONOHYDRAZIDES

CROSS-REFERENCE TO PRIOR APPLICATIONS

This application is a § 371 National Stage Application of PCT International Application No. PCT/EP2016/063125 filed Jun. 9, 2016, which claims benefit to British Patent Application No. 1510019.1 filed Jun. 9, 2015.

The present invention relates to aryl sulfonohydrazides, their use as pharmaceuticals, and in particular, in treating cancer and other diseases associated with the inhibition of MOZ and/or QKF.

BACKGROUND TO THE INVENTION

There are approximately 31,000 new cases of leukaemia diagnosed in the USA per year and approximately 22,000 deaths (Jemal et al 2002). Leukaemia can be divided into acute forms (e.g. acute myeloid leukaemia: AML), characterised by the presence of excessive numbers of immature leukocytes and chronic forms (e.g. chronic myeloid leukaemia: CML), characterised by excessive numbers of differentiated but nevertheless abnormal cells in the blood. In the last 30 years very little progress has been made in curing most types of leukaemia, although substantial advances have been made in management of certain types of leukaemia. Options for curing leukaemia are currently limited to high dose chemotherapy and radiotherapy followed by bone marrow transplant. These therapeutic options, whilst offering the possibility of curing the disease, are very debilitating, associated with high morbidity and are therefore inappropriate for a large number of patients. However, certain types of leukaemia can be effectively managed. For example, Imatinib, blocks the action of the BCR-ABL fusion protein is highly effective in treating CML. Nevertheless, this treatment does not cure the disease and although patients may have completely undetectable levels of the fusion gene they may be expected to relapse if the therapy is discontinued (Cortes et al., 2004). In addition, a proportion of CML patients do not respond to treatment or the cancer eventually becomes resistant to drug treatment (Moen et al., 2007).

Monocytic leukaemia zinc finger protein, Moz, was originally described in a recurrent translocation leading to acute myeloid leukaemia by Borrow et al., 1996. In that translocation Moz is fused to the CREB binding protein (CBP), another co-activator. Since the initial description, MOZ has been found mutated in a number of different recurrent translocations that cause AML. The most common rearrangement of MOZ leads to the fusion of MOZ to CBP but it is also found fused to another coactivator, TIF2. The MOZ-TIF2 fusion protein has been studied in detail. It has been shown that this fusion protein is capable of inducing self-renewal in committed granulocyte/macrophage progenitors. This activity depends on the presence of a nucleosome binding domain in MOZ. This suggests that MOZ is capable of binding to promoters that regulate stem cell genes. The MOZ-TIF2, but not the BCR-ABL fusion protein (found in CML), was able to induce self-renewal in transformed progenitor cells (Huntly et al., 2004).

Patients with MOZ fusion proteins in AML have a typical gene expression profile which includes overexpression of HOX genes (Murati et al., 2009). Hox genes are a subset of homeo domain containing genes. Leukaemias essentially fall into two groups, those in which cells gain a proliferative/survival advantage; for example, through constitutive activation of a cell surface receptor, and those in which there is a block in differentiation. This later category includes oncogenic processes that lead to up-regulation of HOX gene expression. HOXgenes are important regulators of normal blood formation and deregulation of HOX genes leads to leukaemia. Up-regulation of HOX gene expression, for instance HOXB4, leads to expansion of the haematopoietic stem cell compartment showing that HOX proteins are important in regulating stem cells at the transcriptional level. MLL1 (multi-lineage leukaemia 1) is a global regulator of HOX genes and MLL1 translocations in leukaemia lead to deregulation of HOXgene expression (Zeisig et al. 2004). A key feature of MLL translocations (like MOZ-TIF2 fusions) is the ability of the resulting fusion proteins to transform haematopoietic cells into leukaemic stem cells. This results in increased gene expression, significantly HOXgene expression. In particular, HOXA9 expression shows a strong correlation with an unfavorable prognosis (Andreeff et al. 2008). Over-expression of multiple HOX genes was associated with those AML patients having a poor prognosis and HOX genes are found in recurrent translocations leading to leukaemia (Andreeff et al. 2008). Deregulation of HOX gene expression has also been implicated in other forms of cancer, including lung, ovarian, cervical, prostate and breast carcinoma (Shah and Sukumar 2010). Moz is required for the formation of long-term repopulating hematopoietic stem cells but not for the production of mature cell types during embryonic development suggesting that Moz is specifically required for stem cell self-renewal but not proliferation in general. Many genes essential for the formation of definitive hematopoiesis during development are dispensable for the maintenance of adult hematopoiesis, for example Runx1 (Aml1) (Ichikawa et al., 2004).

Mice homozygous for the $Moz^{delta}$ allele, a C-terminal deletion, completely lack long-term re-populating haematopoietic stem cells, as do $Moz^{-/-}$, a null mutation. Surprisingly, progenitors are present, albeit in reduced numbers, early in development and these are able to form all mature blood cell types. This shows that MOZ is specifically required by the stem cell compartment (Thomas et al. 2006). More recently it has been shown that the function of MOZ in the haematopoietic system is dependent on the histone acetyltransferase activity of MOZ (Perez-Campo et al. 2009).

Moz is the founding member of a class of histone acetyl-transferases (HATs), the MYST family. These enzymes are transcription factors, primarily co-activators, which have a key role in regulating the pattern of gene expression in the cell. The MYST proteins have diverse functions in regulating cell proliferation, differentiation, and apoptosis (Thomas et al., 2007).

The MYST family is defined by a highly conserved histone acetyl transferase domain, the MYST domain, containing an atypical zinc finger. Five MYST proteins have been identified in mammals, which can be divided into three subgroups, (1) Moz and Qkf, (2) Mof and Tip60, and (3) Hbo1. Moz (MYST3) and Qkf (MYST4) are highly related, very large multidomain proteins. The amino-terminal 200 amino acids of Moz and Qkf are highly conserved between the two proteins and between animal species. Moz and Qkf have two PHD-type zinc fingers, which are found in a number of proteins regulated chromatin structure. The binding characteristics of three PHD proteins has been described recently (Li et al., 2006). These proteins bind trimethylated lysine 4 of histone 3. The MYST domain is very highly conserved between these proteins, with more than 95% amino acid strongly similar or identical (Thomas et al., 2000), the highest level of conservation found between pairs of MYST proteins. The central portion of both proteins is highly acidic. The carboxy-terminal end consists of a serine-rich and a methionine-rich domain. These domains are unique to Moz and Qkf.

Qkf (Querkopf) was first identified in a mutation screen for genes regulating the balance between proliferation and differentiation during embryonic development (Thomas et al., 2000). Mice homozygous for the Qkf mutant allele have severe defects in cerebral cortex development resulting from a severe reduction in both proliferation and differentiation of specifically the cortical progenitor population during embryonic development. Querkopf is required for the maintenance of the adult neural stem cell population and is part of a system regulating differentiation of stem cells into neurons (Merson et al. 2006). Qkf is also mutated in rare forms of leukaemia (Vizmanos et al. 2003).

The RAS signaling pathway controls cell survival and proliferation. Activating mutations in this pathway are characteristic of a range of cancer types. One member of the RAS family of signal transduction family is KRAS. Activating mutations in KRAS, are present in about 80% of pancreatic carcinomas, almost half of colon carcinomas and lung carcinomas. The most common mutations in KRAS occur in codon 12 and result in the conversion of a glycine residue to either valine or aspartic acid. The enhanced proliferation of cells expressing mutant forms of KRAS, which permanently activate the RAS signaling pathway also activates a network of other pathways including the DNA damage response and these leads to cellular senescence, which is dependent on p53 and Ink4a/Arf. This phenomena is an important barrier to cancer since cancer progression requires that the cancer cells overcome normal defenses against uncontrolled proliferation, namely apoptosis and/or cell cycle exit. Stress caused by oncogene expression may make cancer cells more susceptible to agents inducing cellular senescence. Over expression of KRASV12 can cause oncogene induced senescence. Cellular senescence is a mechanism by which cells prevent unregulated proliferation. Using a loss of function mutation in MOZ (KAT6a) we have demonstrated that MOZ is a suppressor of cellular senescence (Sheikh et al 2015a).

The present inventors have developed aryl sulfonohydrazides which inhibit the activity of MOZ and therefore may be of use in treating conditions ameliorated by the inhibition of the activity of MOZ.

SUMMARY OF THE INVENTION

Therefore, a first aspect of the present invention provides a compound of formula I:

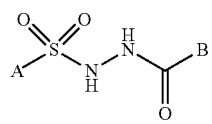

(I)

wherein:
A is selected from:
(i)

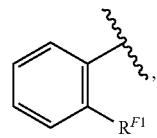

where $R^{F1}$ is H or F;
(ii)

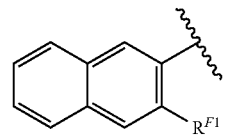

(iii) a N-containing $C_6$ heteroaryl group; and
B is

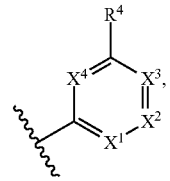

where $X^1$ is either $CR^{F2}$ or N, where $R^{F2}$ is H or F; $X^2$ is either $CR^3$ or N, where $R^3$ is selected from H, Me, Cl, F OMe; $X^3$ is either CH or N; $X^4$ is either $CR^{F3}$ or N, where $R^{F3}$ is H or F; where only one or two of $X^1$, $X^2$, $X^3$ and $X^4$ may be N; and $R^4$ is selected from I, optionally substituted phenyl, optionally substituted $C_{5-6}$ heteroaryl; optionally substituted $C_{1-6}$ alkyl and optionally substituted $C_{1-6}$ alkoxy.

In some embodiments of the first aspect of the invention, the compound is not one or more of the following compounds (P1, P2 and/or P3):

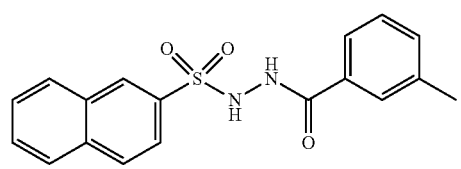

P1

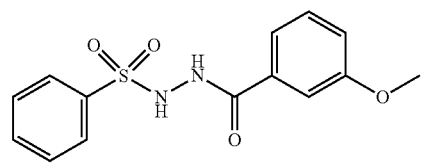

P2

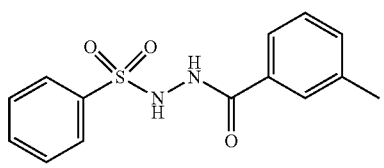

P3

A second aspect of the present invention provides a compound of the first aspect of the invention for use in a method of therapy. The second aspect also provides a pharmaceutical composition comprising a compound of the first aspect, and a pharmaceutically acceptable excipient.

A third aspect of the present invention provides a method of treatment of cancer, comprising administering to a patient in need of treatment, a compound of the first aspect of the invention or a pharmaceutical composition of the second aspect of the invention. The third aspect of the present invention also provides the use of a compound of the first aspect of the invention in the manufacture of a medicament for treating cancer, and a compound of the first aspect of the invention or pharmaceutical composition of the second aspect of the invention for use in the treatment of cancer.

As described below, the compound of the first aspect may be administered simultaneously or sequentially with radiotherapy and/or chemotherapy in the treatment of cancer.

A fourth aspect of the present invention provides a method of treatment of conditions ameliorated by the inhibition of MOZ, comprising administering to a patient in need of treatment, a compound of the first aspect of the invention or a pharmaceutical composition of the second aspect of the invention. The fourth aspect of the present invention also provides the use of a compound of the first aspect of the invention in the manufacture of a medicament for treating conditions ameliorated by the inhibition of MOZ, and a compound of the first aspect of the invention or pharmaceutical composition of the second aspect of the invention for use in the treatment of conditions ameliorated by the inhibition of MOZ.

DEFINITIONS

N-containing $C_6$ heteroaryl group: The term "N-containing $C_6$ heteroaryl group", as used herein, pertains to a monovalent moiety obtained by removing a hydrogen atom from an aromatic ring atom of a monocyclic aromatic compound, which moiety has from 6 ring atoms, of which from 1 to 4 are ring heteroatoms, at least one of which is nitrogen.

Examples of N-containing $C_6$ heteroaryl groups include, but are not limited to, those derived from:

$N_1$: pyridine (azine);
$N_1O_1$: isoxazine;
$N_2$: pyridazine (1,2-diazine), pyrimidine (1,3-diazine), pyrazine (1,4-diazine); and
$N_3$: triazine.

$C_{5-6}$ heteroaryl: The term "$C_{5-6}$ heteroaryl", as used herein, pertains to a monovalent moiety obtained by removing a hydrogen atom from an aromatic ring atom of a heteroaromatic compound, which moiety has from 5 to 6 ring atoms.

Examples of $C_{5-6}$ heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

In this context, the prefixes (e.g. $C_{5-6}$) denote the number of ring atoms, or range of number of ring atoms, whether carbon atoms or heteroatoms.

$C_{1-6}$ alkyl: The term "$C_{1-6}$ alkyl" as used herein, pertains to a monovalent moiety obtained by removing a hydrogen atom from a carbon atom of a hydrocarbon compound having from 1 to 6 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$) and hexyl ($C_6$).

Examples of saturated linear alkyl groups include, but are not limited to, methyl ($C_1$), ethyl ($C_2$), n-propyl ($C_3$), n-butyl ($C_4$), n-pentyl (amyl) ($C_5$) and n-hexyl ($C_6$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-6}$ Alkenyl: The term "$C_{2-6}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-6}$ alkynyl: The term "$C_{2-6}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-6}$ cycloalkyl: The term "$C_{3-6}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 6 carbon atoms.

Examples of cycloalkyl groups include, but are not limited to, those derived from:

saturated cyclic hydrocarbon compounds:
cyclopropane ($C_3$), cyclobutane ($C_4$), cyclopentane ($C_5$), cyclohexane ($C_6$), methylcyclopropane ($C_4$), dimethylcyclopropane ($C_5$), methylcyclobutane ($C_5$), dimethylcyclobutane ($C_6$), and methylcyclopentane ($C_6$); and unsaturated cyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), and methylcyclopentene ($C_6$).

$C_{1-6}$ alkoxy: The term "$C_{1-6}$ alkyloxy" as used herein, pertains to a group —OR, where R is a $C_{1-6}$ alkyl group as defined above.

Optional Substituents

The optional substituents may include one or more of the following groups:
(a) Halo: —F, —Cl, —Br, and —I;
(b) Cyano (nitrile, carbonitrile): —CN;
(c) $C_{1-4}$ alkyl; and
(d) $C_{1-4}$ alkoxy.

Where the optionally substituted group is phenyl, the optional substituents may be selected from:
(a) Halo: —F, —Cl, —Br, and —I;
(b) Cyano (nitrile, carbonitrile): —CN; and
(d) $C_{1-4}$ alkoxy.

Where the optionally substituted group is $C_{5-6}$ heteroaryl, the optional substituents may be selected from:

(a) Halo: —F, —Cl, —Br, and —I; and (c) $C_{1-4}$ alkyl.

Where the optionally substituted group is $C_{1-6}$ alkyl, the optional substituents may be halo (such as F). The alkyl group may be completely substituted, such that it is a perhaloalkyl group.

Where the optionally substituted group is $C_{1-6}$ alkoxy, the optional substituents may be halo (such as F). The alkyl group may be completely substituted, such that it is a perhaloalkyloxy group.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

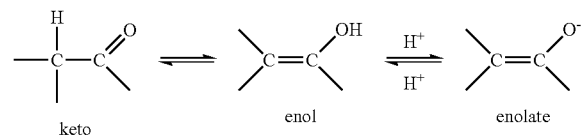

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

MOZ was first identified in a recurrent chromosomal translocation associated with acute myeloid leukemia in which MOZ is fused to the CREB binding protein (CBP), another co-activator. Since the initial description, MOZ has been found mutated in a number of different recurrent translocations that cause AML, including TIF2. The MOZ-TIF2 fusion protein has been studied in detail. It has been shown that this fusion protein is capable of inducing self-renewal in committed granulocyte/macrophage progenitors. This activity depends on the presence of a nucleosome binding domain in MOZ. This suggests that MOZ is capable of binding to promoters that regulate stem cell genes. Interestingly, the MOZ-TIF2, but not the BCR-ABL fusion protein (found in CML), was able to induce self-renewal in transformed progenitor cells.

Using a series of mouse mutants we have shown that Moz is required for the formation of long-term repopulating hematopoietic stem cells but not for the production of mature cell types. Our results showed that Moz is specifically required for stem cell self-renewal but not proliferation or differentiation of progenitors. Certain cancers containing a self-renewing population will be dependent on MOZ enzymatic activity. Therefore, inhibition of MOZ activity may block proliferation of these cancerous cells.

Thus, agents disclosed herein may be useful in the treatment of cancers associated with a self-renewing population of cells.

Not all tumour cells are equivalent in their capacity to promote cancer. It has been known for some time that the only a minority of cells are capable of transplanting the disease. These observations have led to the cancer stem cell (CSC) hypothesis. This hypothesis suggests that the long-term presence of the disease is dependent on a minority of cells, those that have tumour-initiating ability (Pelletier et al., 2003, Berndsen et al., 2007, Decker et al., 2008). As results have demonstrated that MOZ is specifically required for stem cell self-renewal, inhibition of MOZ may also block proliferation of cancer stem cells.

There is strong evidence for the existence of cancer stem cells in AML (Acute Myeloid Leukemia), CML (Chronic Myeloid Leukemia), breast cancer, lung cancer and in brain tumours. Indeed, a regulatory pathway including Moz may also be involved in other types of cancer particularly lung cancer. In the case of human AML and CML it has been shown that a rare population of cells bearing a distinctive pattern of cell surface markers, similar to those found on normal haematopoietic stem cells, have the properties of leukaemic stem cells. Leukaemic stem cells have the property of self-renewal combined with a high proliferative potential. In addition, leukaemic stem cells tend to be drug resistant. Irrespective of whether "true" cancer stem cells exist in all types of leukaemia, it is clear that the long-term persistence of malignant disease depends on genetically abnormal cells retaining the property of self-renewal. These features of leukaemia and other cancers suggests that drugs that modulate the property of self-renewal will be useful in the management and/or treatment of the disease.

Together, studies of the normal function of MOZ and its role in oncogenesis suggest that it is a master regulator of hematopoietic stem cells and part of a gene regulatory network commonly mutated in leukaemia.

The agents of the invention may therefore be useful in the treatment of cancers associated with a self-renewing population of cells, such as cancer stem cells. In particular, the agents disclosed herein may be useful in the treatment of breast cancer, lung cancer or brain tumour.

The agents of the invention may be useful in the prevention of metastasis of cancer. The agents disclosed herein may be useful in treating leukaemia. The leukaemia may be associated with a self-renewing population of cells, such as cancer stem cells. The leukemia may be AML. The leukaemia may be CML.

MOZ and QKF have been found mutated in a number of different recurrent translocations that cause AML. The MOZ-TIF2 fusion has been extensively studied and is capable of inducing self-renewal in committed granulocyte/macrophage progenitors. Compounds that are capable of inhibiting MOZ or QKF may be useful in the treatment of conditions associated with MOZ or QKF translocations, respectively.

The translocation t(8;16)(p11;p13), which results in the fusion of MOZ to CBP is present in approximately 0.7% AML cases. These are classified as M4/M5 or M5 on the French-American-British (FAB) classification. This subtype of AML has a very poor prognosis, with a mean survival time of 2 months and is more frequent among fatal childhood leukaemia than in adults (Stark et al., 1995). A recent survey of 30 cases showed that in the majority of cases Moz rearrangements occur as a result of therapy for solid tumours or other haematological malignancy (Gervais et al., 2008). Moz is also found fused to TIF2 (NCOA2) as the result of the inv(8)(p11q13), to p300: t(8;22)(p11;q13) and NCOA3: t(8;20)(p11;q13). Moz fusion proteins in AML have been shown to cause de-regulation of HOX gene expression and perturb gene regulation by CBP. Other MOZ translocations associated with AML include t(8;19)(p11;q13), t(8;13)(p11;q11), t(8;9)(p114;q32) and t(6;8)(q27;p11).

The compounds described herein may be useful for treating leukemia associated with a moz translocation. The cancer may be a cancer in which a moz fusion protein is expressed, such as a MOZ:CBP or MOZ:TIF fusion protein. The cancer may be associated with a t(8; 16)(p11;p13), inv(8)(p11q13), to p300: t(8;22)(p11;q13), NCOA3: t(8;20) (p11;q13), t(8;19)(p11;q13), t(8;13)(p11;q11), t(8;9)(p114; q32) or t(6;8)(q27;p11) translocation. The agents disclosed herein may be useful in the treatment of leukemia associated with a t(8; 16)(p11;p13) translocation.

A common feature of translocations involving MOZ is that the carboxy-terminal serine-rich and methionine-rich domains are not present in the leukemogenic fusion protein. Thus, conditions associated with C-terminal truncations or C-terminal deletions of MOZ may be treatable with the compounds capable of inhibiting MOZ activity.

Patients with MOZ fusion proteins in AML have a typical gene expression profile which includes overexpression of HOX genes. Deregulation of HOX gene expression has also been implicated in other forms of cancer, including lung, ovarian, cervical, prostate and breast carcinoma. The agents disclosed herein may also be used to treat cancers and conditions associated with deregulation of HOX gene expression, including lung, ovarian, cervical, prostate and breast carcinoma.

Patients may be selected for treatment as described herein by detecting the presence of a MOZ translocation, or a fusion protein associated with such a translocation. Translocation of human homologue of Qkf, (MORF), has also been found in AML (Panagopoulos et al., 2001). The translocation t(10;16)(q22;p13) leads to the fusion of MORF and CBP producing a fusion protein very similar to the t(8;16) (p11;p13) translocations which lead to the fusion of MOZ and CBP. Thus, the agents disclosed herein may be useful in the treatment of conditions associated with a t(10;16)(q22; p13) translocation.

Recurrent translocations of Qkf are common in uterine leiomyomata. This benign tumor is the most common human neoplasm affecting about ¾ of middle-aged women. 10q22 translocations and other genetic abnormalities are also associated with leiomyosarcomas leading to the suggestion that a common pathway is involved in the development of uterine leiomyomata and leiomyosarcomas. Runx1 is upregulated in leiomyomata and strongly upregulated in leiomyosarcomas. Agents disclosed herein may be useful in the treatment of leimyomata and/or leiomyosarcoma.

Aberrant expression of MYST4/qkf is also associated with a range of non-cancerous conditions. Inhibitors of MYST4 activity may also be therapeutic in these conditions. For example, other conditions treatable by the compounds of the invention include myelodysplastic syndrome, a haematological medical condition associated with dysplasia of myeloid cells. Myelodysplastic syndrome may occur following therapy for t(8;21)(q22;q2) M2 Acute Myeloid Leukemia (AML), or from environmental exposures to mutagens such as radiation and benzene. It may arise spontaneously. The myelodysplastic syndrome may subsequently develop into AML. Thus, the compounds of the invention may be useful for the prevention of AML in patients diagnosed with myelodysplastic syndrome. The compounds may be useful in the prevention of AML in patients undergoing treatment for myelodysplastic syndrome.

A mutated form of MYST4 has been associated with a rare form of Noonan's syndrome, and mutations in MYST4 lead to Say-Barber-Biesecker-Young-Simpson variant of Ohdo syndrome of mental retardation (also known as Ohdo Blepharaophimosis). Thus, compounds capable of inhibiting an activity of QKF may also be useful in the treatment of these disorders.

MOZ is required for proliferation of B cells. The agents disclosed herein may be useful for the treatment of conditions associated with aberrant proliferation of B cells, such as leukemia and lymphoma. They may be useful in the treatment or inhibition of relapse of pateints in remission after standard treatments for leukemia or lymphoma.

Cellular senescence is a mechanism by which cells prevent unregulated proliferation. Using a loss of function mutation in MOZ (KAT6a) we have demonstrated that MOZ is a suppressor of cellular senescence (Sheikh et al 2015a). The agents disclosed herein may be useful in the treatment of cancers in which avoidance of cellular senescence is an important mechanism for cancer progression. Over expression of KRASV12 can cause oncogene induced senescence. Therefore, diseases associated with overexpression of RAS or mutant forms of RAS may be sensitized to senescence induction, and the compounds disclosed herein may be useful in treatment of such diseases. Activating mutations in KRAS, are present in about 80% of pancreatic carcinomas, almost half of colon carcinomas and lung carcinomas. The compounds disclosed herein may therefore by useful in the treatment of pancreatic carcinoma, colon carcinoma, or lung carcinoma, and/or cancer associated with activating mutations in KRAS.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting.

Compounds of formula I, as described above, can be prepared by synthetic strategies outlined below, wherein the definitions above apply.

Compounds of Formula I:

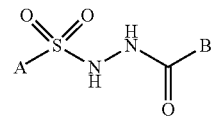

may be synthesised by coupling an acid hydrazide of formula 2 with a sulfonyl chloride of formula 3:

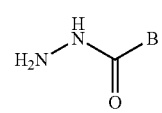

Formula 2

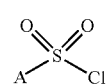

Formula 3

The coupling may take place in pyridine, for example at 10° C., followed by acidification, for example in HCl. The compounds of formula 2 and 3 may be commercially available or synthesisable using known routes.

Compounds of Formula I:

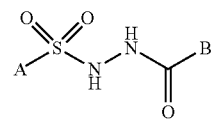

may be synthesised by coupling an sulfonyl hydrazide of formula 4 with an acid of formula 5:

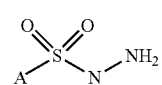

Formula 4

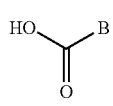

Formula 5

The coupling reaction may be carried out under appropriate coupling conditions, examples of which are described below. The compounds of formulae 4 and 5 may be commercially available, or may be synthesisable using known routes. A number of acids are synthesised in the examples below, illustrating some of the known routes.

FURTHER EMBODIMENTS

The further embodiments expressed below may be combined, where appropriate.

A

In some embodiments, A is:

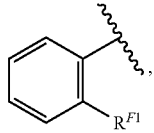

where $R^{F1}$ is H or F. In some of these embodiments, $R^{F1}$ is H. In others of these embodiments, $R^{F1}$ is F.

In some embodiments, A is:

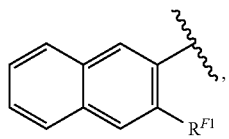

where $R^{F1}$ is H or F. In some of these embodiments, $R^{F1}$ is H. In others of these embodiments, $R^{F1}$ is F.

In some embodiments, A is a N-containing $C_6$ heteroaryl group. In some of these embodiments, A is pyridinyl. In other of these embodiments, A is isoxazinyl. In other of these embodiments, A is pyridazinyl, pyrimidinyl or pyrazinyl. In other of these embodiments, A is triazinyl. If A is a N-containing $C_6$ heteroaryl group, it may have only N ring heteroatoms, and it may have only one or two of these.

B

In some embodiments, none of $X^1$, $X^2$, $X^3$ and $X^4$ are N.

In other embodiments, one of $X^1$, $X^2$, $X^3$ and $X^4$ is N. In some of these embodiments, $X^3$ is N. In other of these embodiments, $X^2$ is N. In other of these embodiments, $X^4$ is N.

In other embodiments, two of $X^1$, $X^2$, $X^3$ and $X^4$ are N.

In some embodiments, only one of $R^{F2}$, $R^3$ and $R^{F3}$ is F.

In some embodiments, $R^{F2}$ is H. In some of these embodiments, $R^{F1}$ (if present) is F.

In other embodiments, $R^{F2}$ is F. In some of these embodiments, $R^{F1}$ (if present) is H. In some of these embodiments, $R^{F3}$ is H, and $R^3$ is not F, i.e. $R^{F2}$=F, $R^{F1}$ (if present)= $R^{F3}$=H, $R^3 \neq F$.

In some embodiments, $R^{F3}$ is H. In some of these embodiments, $R^{F1}$ (if present) is F.

In other embodiments, $R^{F3}$ is F. In some of these embodiments, $R^{F1}$ (if present) is H. In some of these embodiments, $R^{F3}$ is H, and $R^3$ is not F, i.e. $R^{F3}$=F, $R^{F1}$ (if present)= $R^{F2}$=H, $R^3 \neq F$.

In some embodiments, $R^3$ is H. In other embodiments, $R^3$ is Me. In other embodiments, $R^3$ is Cl. In other embodiments, $R^3$ is F. In other embodiments, $R^3$ is OMe.

In some embodiments when $R^3$ is F, then $R^{F2}$ and $R^{F3}$ are H. In some of these embodiments, $R^{F1}$ is H (i.e. $R^{F1}=R^{F2}=R^{F3}$=H, $R^3$=F). In other of these embodiments, $R^{F1}$ is F (i.e. $R^{F2}=R^{F3}$=H, $R^{F1}=R^3$=F).

The following table sets out a number of possible embodiments, where none of $X^1$, $X^2$, $X^3$ and $X^4$ are N:

| $R^{F1}$ | $R^{F2}$ | $R^3$ | $R^{F3}$ |
|---|---|---|---|
| H | H | H | H |
| F | H | H | H |
| H | H | H | F |
| H | H | Cl | H |
| H | F | Cl | H |
| F | H | Cl | H |
| H | H | Me | H |
| H | F | Me | H |
| F | H | Me | H |
| H | H | OMe | H |
| F | H | OMe | H |
| H | H | F | H |
| F | H | F | H |

In some embodiments, $R^4$ is I.

In other embodiments, $R^4$ is optionally substituted phenyl. The optional substituents may be selected from:

(a) Halo: —F, —Cl, —Br, and —I.
(b) Cyano (nitrile, carbonitrile): —CN;
(d) $C_{1-4}$ alkoxy.

In some embodiments, there may be a single substituent selected from halo, cyano and $C_{1-4}$ alkoxy.

If the substituent is halo, it may be selected from F and Cl, which may be in any available ring position (e.g. ortho, meta, para).

If the substituent is cyano, it may be in any available ring position (e.g. ortho, meta, para). In some of these embodiments, it may be meta.

If the substituent is $C_{1-4}$ alkoxy, it may be methoxy, which may be in any available ring position (e.g. ortho, meta, para).

In some embodiments, $R^4$ is unsubstituted phenyl.

In other embodiments, $R^4$ is optionally substituted $C_{5-6}$ heteroaryl. The optional substituents may be selected from:

(a) Halo: —F, —Cl, —Br, and —I; and
(c) $C_{1-4}$ alkyl.

If the substituent is halo, it may be F, which may be in any available ring position.

If the substituent is $C_{1-4}$ alkyl, it may be Me, which may be in any available ring position.

Exemplary $R^4$ groups include:

(a) $C_6$ ($N_1$):

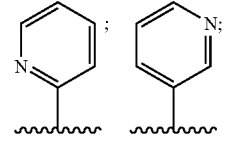

(b) $C_6$ ($N_2$):

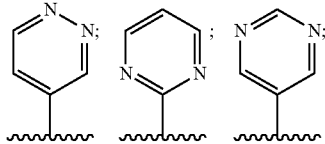

(c) $C_5$ ($O_1$ or $S_1$):

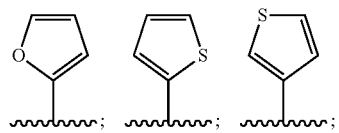

(d) C$_5$ (N$_2$):

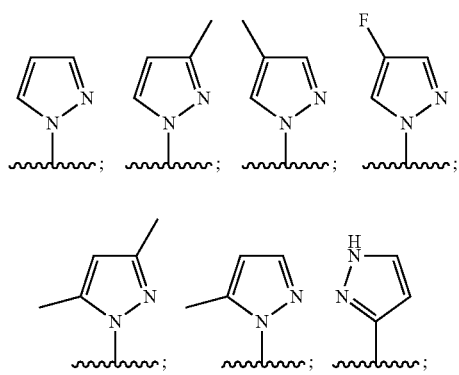

(e) C$_5$ (N$_3$):

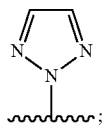

(f) C$_5$ (N$_1$S$_1$)

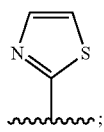

(g) C$_5$ (N$_2$O$_1$)

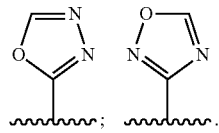

In some embodiments, R$^4$ is an unsubstituted C$_{5-6}$ heteroaryl group.

In other embodiments, R$^4$ is optionally substituted C$_{1-6}$ alkyl. The optional substituents may be halo (such as F). The alkyl group may be completely substituted, such that it is a perhaloalkyl group, for example, CF$_3$. In some embodiments where R$^4$ is optionally substituted C$_{1-6}$ alkyl, the group may be unsubstituted. Exemplary R$^4$ groups include methyl, ethyl and iso-propyl.

In other embodiments, R$^4$ is optionally substituted C$_{1-6}$ alkoxy. The optional substituents may be halo (such as F). The alkyl group may be completely substituted, such that it is a perhaloalkyloxy group, for example, —OCF$_3$. In some embodiments where R$^4$ is optionally substituted C$_{1-6}$ alkyloxy, the group may be unsubstituted. Exemplary R$^4$ groups include:

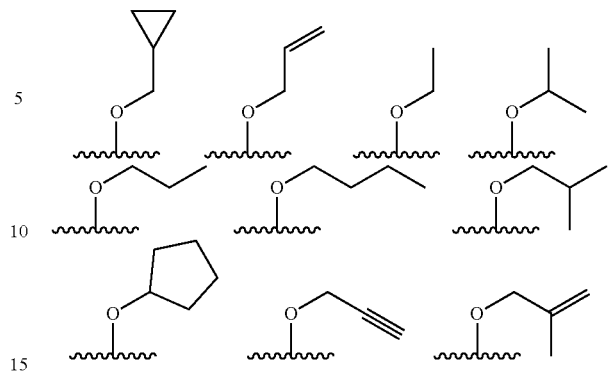

In some embodiments of the present invention there is provided a compound of formula Ia:

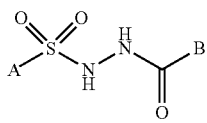

(Ia)

wherein:
A is selected from:
(i)

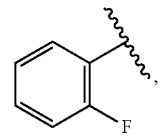

(ii)

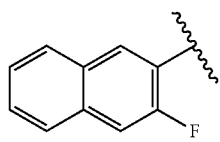 [SMILES: *c1cc2ccccc2cc1F]

(ii) a N-containing C$_6$ heteroaryl group; and
B is:

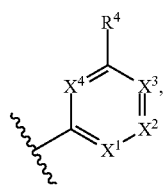

where X$^1$ is either CR$^{F2}$ or N, where R$^{F2}$ is H or F; X$^2$ is either CR$^3$ or N, where R$^3$ is selected from H, Me, Cl, F OMe; X$^3$ is either CH or N; X$^4$ is either CR$^{F3}$ or N, where R$^{F3}$ is H or F; where only one or two of X$^1$, X$^2$, X$^3$ and X$^4$ may be N; and $R^4$ is selected from I, optionally substituted phenyl, optionally substituted $C_{5-6}$ heteroaryl; optionally substituted $C_{1-6}$ alkyl and optionally substituted $C_{1-6}$ alkoxy.

In some embodiments of the present invention there is provided a compound of formula Ib:

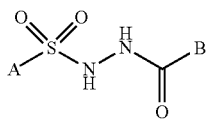
(Ib)

wherein:
A is selected from:
(i)

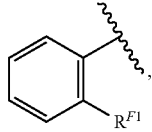

where $R^{F1}$ is H or F;
(ii)

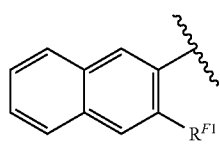

(ii) a N-containing $C_6$ heteroaryl group; and
B is:

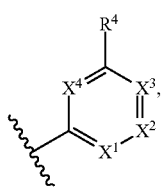

where $X^1$ is either CF or N; $X^2$ is either $CR^3$ or N, where $R^3$ is selected from H, Me, Cl, F OMe; $X^3$ is either CH or N; $X^4$ is either $CR^{F3}$ or N, where $R^{F3}$ is H or F; where only one or two of $X^1$, $X^2$, $X^3$ and $X^4$ may be N; and $R^4$ is selected from I, optionally substituted phenyl, optionally substituted $C_{5-6}$ heteroaryl; optionally substituted $C_{1-6}$ alkyl and optionally substituted $C_{1-6}$ alkoxy.

In some embodiments of the present invention there is provided a compound of formula Ic:

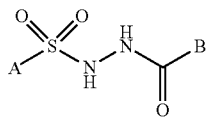
(Ic)

wherein:
A is selected from:
(i)

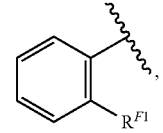

where $R^{F1}$ is H or F;
(ii)

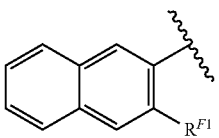

(ii) a N-containing $C_6$ heteroaryl group; and
B is:

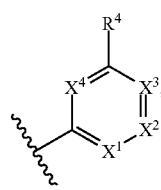

where $X^1$ is either $CR^{F2}$ or N, where $R^{F2}$ is H or F; $X^2$ is either $CR^3$ or N, where $R^3$ is selected from H, Me, Cl, F OMe; $X^3$ is either CH or N; $X^4$ is either $CR^{F3}$ or N, where $R^{F3}$ is H or F; where only one or two of $X^1$, $X^2$, $X^3$ and $X^4$ may be N; and $R^4$ is selected from I, optionally substituted phenyl, optionally substituted $C_{5-6}$ heteroaryl; optionally substituted $C_{2-6}$ alkyl and optionally substituted $C_{2-6}$ alkoxy.

In some embodiments of the present invention there is provided a compound formula Id:

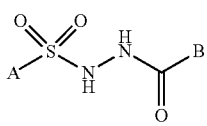
(Id)

wherein:
A is

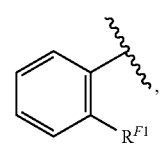

where $R^{F1}$ is H or F;

B is:

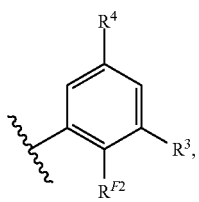

where $R^{F2}$ is H or F; $R^3$ is selected from H, F and Me; and $R^4$ is $C_{2-3}$ alkoxy;

where only one of $R^{F1}$ and $R^{F2}$ is F.

In some embodiments of the present invention there is provided a compound formula Ie:

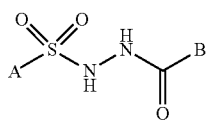 (Ie)

wherein:

A is

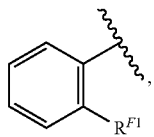

where $R^{F1}$ is H or F;

B is:

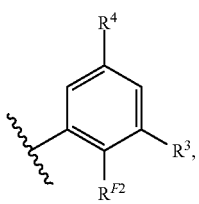

where $R^{F2}$ is H or F; $R^3$ is selected from H, F and Me; and $R^4$ is selected from:

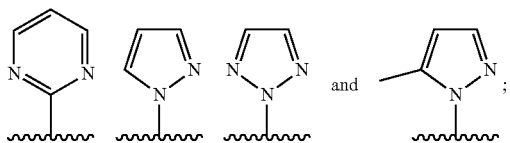

where only one of $R^{F1}$ and $R^{F2}$ is F.

EXAMPLES

The following are examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), isopropanol (i-PrOH), ether or diethyl ether ($Et_2O$), acetic acid (AcOH), acetonitrile (MeCN), dichloromethane (methylene chloride, DCM), trifluoroacetic acid (TFA), dimethylformamide (DMF), tetrahydrofuran (THF), dimethylsulfoxide (DMSO), meta-chloroperoxybenzoic acid (mCPBA), 1,1'-bis(diphenylphosphino)ferrocene (dppf), 2-dicyclohexylphosphino-2',6'-diisopropoxybiphenyl (Ruphos), tert-butyloxycarbonyl (Boc), 2-(trimethylsilyl)ethoxymethyl (SEM), 2-(1H-7-azabenzotriazol-1-yl)-1,1,3,3-tetramethyluronium hexafluorophosphate (HATU), 1-ethyl-3-(3-dimethylaminopropyl) carbodiimide (EDCI), 4-dimethylaminopyridine (DMAP), N,N-diisopropylethylamine (DIPEA), lithium bis(trimethylsilyl)amide (LiHMDS) and 1-hydroxybenzotriazole (HOBt), Tetrabutylammonium bromide (TBAB), Chloro-(2-dicyclohexylphosphino-2',6'-diisopropoxy-1,1'-biphenyl)[2-(2-aminoethyl)phenyl]palladium(I)-methyl-t-butyl ether adduct (RuPhos palladacycle precatalyst), Lithium bis(trimethylsilyl)amide (LiHMDS), Bis(trimethylaluminum)-1,4-diazabicyclo[2.2.2]octane adduct ($DABAL-AlMe_3$), 2-Dicyclohexylphosphino-2',4',6'-triisopropylbiphenyl (XPhos), dimethoxyethane (DME).

General Experimental Details $^1$H NMR $^1$H Nuclear Magnetic Resonance spectra were recorded at 400.13 Hz, on an Avance III Nanobay 400 MHz Bruker spectrometer coupled to the BACS 60 automatic sample changer. Results are recorded as follows: chemical shifts (δ) in ppm acquired in either $CDCl_3$ (7.26 ppm for $^1$H) or DMSO-$d_6$ (2.50 ppm for $^1$H) as a reference. Solvents used for NMR studies are from Cambridge Isotope Laboratories. Each proton resonance was assigned according to the following convention: chemical shift (δ), multiplicity, coupling constant (J Hz) and number of protons. In reporting of the spectral data, the following abbreviations are utilised: s, singlet; d, doublet; t, triplet; q, quartet; m, multiplet.

LCMS A

Low resolution mass spectrometry analyses were performed on an Agilent 6100 Series Single Quad LC/MS coupled with an Agilent 1200 Series HPLC, 1200 Series G1311A quaternary pump, 1200 series G1329A thermostatted autosampler and 1200 series G1314B variable wavelength detector. The conditions for liquid chromatography were: reverse phase HPLC analysis fitted with a Phenomenex Luna C8(2) 5 μm (50×4.6 mm) 100 Å column; column temperature: 30° C.; injection volume: 5 μL; solvent: 99.9% acetonitrile, 0.1% formic acid; gradient: 5-100% of solvent over 10 min; detection: 254 nm. The conditions for mass spectrometry were: quadrupole ion source; ion mode: multimode-ES; drying gas temp: 300° C.; vaporizer temperature: 200° C.; capillary voltage: 2000 V (positive), 4000 (negative); scan range: 100-1000 m/z; step size: 0.1 sec; acquisition time: 10 min.

LCMS B

All analyses were done on an Agilent 6224 TOF LC/MS Mass Spectrometer coupled to an Agilent 1290 Infinity (Agilent, Palo Alto, Calif.). All data were acquired and reference mass corrected via a dual-spray electrospray ionisation (ESI) source. Each scan or data point on the Total Ion Chromatogram (TIC) is an average of 13,700 transients, producing a spectrum every second. Mass spectra were created by averaging the scans across each peak and background subtracted against the first 10 seconds of the TIC. Acquisition was performed using the Agilent Mass Hunter Data Acquisition software version B.05.00 Build 5.0.5042.2 and analysis was performed using Mass Hunter Qualitative Analysis version B.05.00 Build 5.0.519.13.

Chromatographic separation was performed using an Agilent Zorbax SB-C18 Rapid Resolution HT 2.1×50 mm, 1.8 μm column (Agilent Technologies, Palo Alto, Calif.) using an acetonitrile gradient (5% to 100%) over 3.5 min at 0.5 mL/min.

LCMS C:

Liquid Chromatography-Mass spectrometry (LCMS) was performed on two different instruments, a Finnigan LCQ Advantage MAX carried out on a Phenomenex column (Gemini, 3 μm, 110 Å, 20×4 mm) and a Waters Auto Purification System 3100 carried out with a Waters column (XBridge, 4 μm, 100 Å, 4.6×100 mm). High Performance Liquid Chromatography (HPLC) was also carried out on two different instruments, the Waters Auto Purification System 3100 with a Waters column (XBridgePrep C18, 5 μm, OBD, 19×100 mm) and the Waters Alliance HT 2795 with a Phenomenex column (Luna, 5 μm, C18, 100 Å, 150×10 mm)

Standard Methods

Sulfonamide Coupling

To a solution of the benzoic acid hydrazide in pyridine, cooled to 100° C. with an ice bath, was added dropwise 1 mL of the benzenesulfonyl chloride. The reaction mixture was stir for 4 hours at room temperature. Then, the mixture was poured into a solution of 2 M HCl with ice. A precipitate formed and was filtered on a sintered funnel. The solid was slurried in hot isopropanol and allowed to cool down in the freezer overnight. The solvent was filtered off and the solid dried to give the desired product.

Carboxylation

To a solution of the biphenyl (1 eq.) in THF (1 M) was added n-butyllithium (2.5 M in hexanes, 1.1 eq). The reaction mixture was allowed to stir at −78° C. for 40 minutes before being poured onto a vast excess of dry ice. After the majority of dry ice evaporated, the reaction mixture was concentrated in vacuo. The resulting solid was suspended with a small amount of water, acidified with 1 M HCl and filtered. The solid was washed with 1 M HCl and petroleum benzine (PB) to yield the desired product.

Suzuki Coupling Method A

To a degassed solution of 9:1 1,4-dioxane:$H_2O$ (0.2 M), under an atmosphere of nitrogen, was added the benzoic acid (1 eq.), the boronic acid (3 eq.), $K_2CO_3$ (1.5 eq.) and the palladium catalyst (0.05 eq.). The reaction was irradiated in a CEM microwave at 80° C. for 30 minutes, then cooled and passed through a pad of Celite®. The Celite was washed with EtOAc (20 mL). The mixture was acidified using 2 M HCl (1 mL) and the organics removed in vacuo. The solid precipitate was collected via filtration to give the title compound.

Suzuki Coupling Method B

To a degassed solution of 3:1 1,4-dioxane:$H_2O$ (0.3 M), under an atmosphere of nitrogen, was added the benzoic acid (1 eq.), the boronic acid (2 eq.), 2 M aq. soln of $K_3PO_4$ (3 eq.) and the palladium catalyst (0.05 eq.). The reaction was irradiated in a CEM microwave at 150° C. for 30 minutes, then cooled and passed through a pad of Celite. The Celite was washed with EtOAc (20 mL). The mixture was acidified using 2 M HCl (1 mL) and the organics removed in vacuo. The solid precipitate was collected via filtration to give the title compound.

Suzuki Coupling Method C

The boronate (1 eq.), aryl bromide hydrobromide salt (1.1 eq.) and $PdCl_2(dppf)$ (0.05 eq.), under an atmosphere of nitrogen, were suspended in dioxane (0.2 M). A solution of $K_2CO_3$ (1.5 eq.) in water (0.3 M) was added and the mixture degassed. The reaction was irradiated in a CEM microwave at 120° C. for 30 minutes. The mixture was cooled, and the volatile solvents removed in vacuo. The aqueous residue was diluted with water and shaken with DCM. The mixture was filtered through Celite, the aqueous layer separated and washed with a further portion of DCM. The organic extracts were discarded. The aqueous phase was diluted with water and treated with 5% w/v citric acid. The resulting precipitate was collected by filtration, washed with water and dried under vacuum to give the title compound.

Suzuki Coupling Method D

The aryl bromide (1.0 eq), arylboronic acid (1.1 eq), $K_2CO_3$ (1.5 eq) and $PdCl_2(PPh_3)_2$(5 mol %), under an atmosphere of nitrogen, were suspended in a 1:1 THF:$H_2O$ mixture (4 mL per mmol). The reaction was heated to reflux and allowed to stir overnight. The mixture was then cooled to room temperature and partitioned between EtOAc and water. The organic layer was washed with water, brine, dried over $Na_2SO_4$, filtered, dry loaded onto silica and purified by column chromatography using silica as the stationary phase and a mixture of petroleum benzine/EtOAc as the eluent.

Suzuki Coupling Method E

To a degassed solution of 1,4-dioxane (0.1 M), under an atmosphere of nitrogen, was added the benzoic acid (1 eq.), bis(pinacolato)diboron (1.5 eq.), and KOAc (4.4 eq.) sequentially. The mixture was degassed once again and then $PdCl_2(dppf)$ (5 mol %) was added. The resulting solution was heated to 110° C. overnight. The solvent was removed in vacuo to give a dark gummy residue, which was taken up into EtOAc and $H_2O$. The organic layer was separated and the aqueous was further extracted with EtOAc (2×). The combined organic layers were washed with 2 M HCl, dried over $MgSO_4$ and concentrated in vacuo to give a dark brown solid. The resulting solid was triturated with petroleum benzine to afford the title compound.

Suzuki Coupling Method F

To a degassed solution of DMF:$H_2O$ (10:1 ratio) (0.3 M), under an atmosphere of nitrogen, was added the pinacol ester (1 mmol), 2-bromopyridine or 2-chloropyrimidine (1.5 eq.), and $Cs_2CO_3$ (4.4 eq.). The whole mixture was degassed once again and then $Pd(PPh_3)_4$(5 mol %) was added. The resulting solution was heated to 110° C. overnight. The solvent was removed in vacuo to give a dark gummy residue, which was taken up into EtOAc and $H_2O$, then acidified with 2 M HCl to pH 2. The organic layer was separated and the aqueous layer was further extracted with EtOAc (2×). The combined organic layers were dried over $MgSO_4$ and concentrated in vacuo to give a black oily residue. The residue was dry loaded onto silica gel in vacuo then purified by flash column chromatography, eluting with 10-30% EtOAc/petroleum benzine and 1% acetic acid to afford the title compound.

Ullmann Transformation Method A $Na_2CO_3$ (1 eq.) was added to a degassed solution of water (0.35 M) and the appropriate bromobenzoic acid (1 eq.) and was refluxed for 30 minutes. A further portion of $Na_2CO_3$ (1.5 eq.) was added to the reaction and refluxed for a further 30 minutes. Separately CuBr$_2$ (0.1 eq.) and trans-N, N-dimethylcyclohexane-1,2-diamine (0.2 eq.) were added to degassed water (0.04 M) and an intense blue colour was observed. This mixture was added to the refluxing aqueous solution and allowed to stir at this temperature overnight. The resulting solution was allowed to cool to room temperature and was acidified with conc. HCl and extracted into EtOAc. The organics were dried with MgSO$_4$, filtered, and the solvent removed in vacuo to give the desired product.

Ullmann Coupling Method B

The benzoic acid (1 eq.), substituted N-heterocycle (1.5 eq.), K$_2$CO$_3$ (4.5 eq.), and CuI (0.24 eq.) were suspended in dry, degassed DMF (0.1 M), under an atmosphere of nitrogen, and to this was added trans-N, N-dimethyl-1,2-cyclohexanediamine (0.2 eq.). The resulting solution was heated to 110° C. overnight. The solvent was removed in vacuo, and the resulting material taken up into EtOAc and H$_2$O and acidified with 2 M HCl (pH ~2). The organic layer was separated and the aqueous layer was further extracted with EtOAc (2×). The combined organic layers were washed with H$_2$O and brine, then dried over MgSO$_4$ and concentrated in vacuo to give a brown oily residue. The residue was dry loaded onto silica gel in vacuo before being purified by flash column chromatography, eluting with 10-30% EtOAc/petroleum benzine and 1% acetic acid to afford the title compound.

Alkylation of Aryl Hydroxyl Method

To a solution of the hydroxyl benzoic acid (1 eq.) and the bromoalkyl derivative (3.5 eq.) in DMF (0.33 M) was added K$_2$CO$_3$ (2.5 eq.). This solution was heated to 110° C. for 4 hours, upon which time the reaction was cooled to room temperature and acidified with conc. HCl, then extracted with EtOAc. The organics were collected and dried with MgSO$_4$, filtered and the solvent removed in vacuo to give a yellow slurry. This was then dissolved in EtOH (0.1 M) and NaOH (2.5 eq.) was added to the mixture and allowed to stir at room temperature overnight. The solvent was then removed in vacuo. To the resulting solid was added water, and this was then acidified with conc. HCl. The resulting precipitate was collected by filtration to give the desired product.

Amide Coupling Method A

The benzoic acid (1 eq.), sulfonyl hydrazide (1.25 eq.), HOAt (1.25 eq.) and EDCI.HCl (1.25 eq.) were dissolved in MeCN (0.8 M), under an atmosphere of nitrogen. The solution was heated to 40° C. and allowed to stir for 17 hours, upon which time the reaction was cooled, concentrated in vacuo, then loaded directly onto silica for purification. The crude material was purified by silica gel chromatography (Isolera Biotage, 0-100% EtOAc in petroleum benzine 40-60° C.). Product-containing fractions were combined and concentrated in vacuo to give the title compound.

Amide Coupling Method B

The benzoic acid (1 eq.), sulfonyl hydrazide (1.25 eq.), HOAt (1.25 eq.) and EDCI.HCl (1.25 eq.) were dissolved in MeCN (0.8 M), under an atmosphere of nitrogen. The solution was heated to 40° C. and allowed to stir for 17 hours, upon which time the reaction was cooled, concentrated in vacuo. The residue was partitioned between water and EtOAc, and the layers separated. The aqueous layer was further washed with two portions of EtOAc. The combined organic layers were dried (Na$_2$SO$_4$) then loaded directly onto silica for purification. The crude material was purified by silica gel chromatography (Isolera Biotage, 0-100% EtOAc in petroleum benzine 40-60° C.). Product-containing fractions were combined and concentrated in vacuo to give the title compound.

Amide Coupling Method C

To a stirred solution of the carboxylic acid in acetonitrile (0.1 M) was added HBTU (1.0 eq) and the resulting reaction mixture was cooled to 0° C. N-Ethyldiisopropylamine (1 eq) was added and the reaction mixture was allowed to stir at 0° C. for 1 hour. The sulfonylhydrazide (1.2 eq.) was then added and the reaction mixture was heated to reflux overnight. The reaction mixture was then cooled to room temperature and was dry loaded onto silica in vacuo before being purified by column chromatography using silica gel as the stationary phase and a mixture of petroleum benzine/EtOAc as the eluent.

Synthesis of Key Intermediates (a) 5-Chloro-4-fluoro-[1,1'-biphenyl]-3-carboxylic acid (I1)

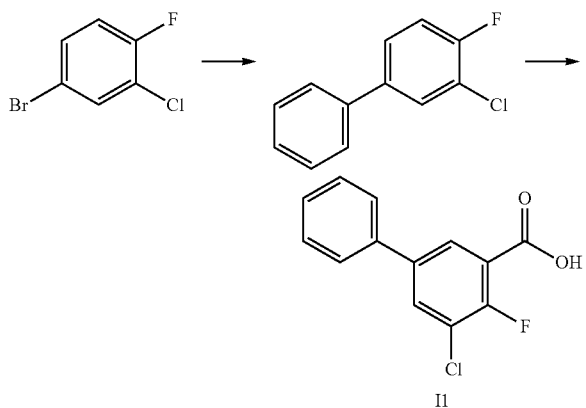

(i) 3-Chloro-4-fluoro-1,1'-biphenyl was obtained by the Suzuki coupling method D from 1-bromo-3-chloro-4-fluorobenzene as a pale yellow oil that crystallized as an off-white solid upon standing (43% yield). $^1$H NMR (400 MHz, CDCl$_3$) δ 7.60 (dd, J=7.0, 2.3 Hz, 1H), 7.53-7.46 (m, 2H), 7.44-7.41 (m, 3H), 7.38-7.35 (m, 1H), 7.19 (t, J=8.7 Hz, 1H).

(ii) 5-Chloro-4-fluoro-[1,1'-biphenyl]-3-carboxylic acid was obtained by the carboxylation method from 3-chloro-4-fluoro-1,1'-biphenyl as a colourless solid (84% yield). $^1$H NMR (400 MHz, DMSO) δ 13.76 (s, 1H), 8.09 (dd, J=6.4, 2.4 Hz, 1H), 8.01 (dd, J=6.1, 2.4 Hz, 1H), 7.78-7.64 (m, 2H), 7.49 (m, 2H), 7.45-7.36 (m, 1H). LCMS A rt 6.62 min, m/z 249.1[M−H]$^-$ (b) 4-Fluoro-5-methyl-[1,1'-biphenyl]-3-carboxylic acid (I2)

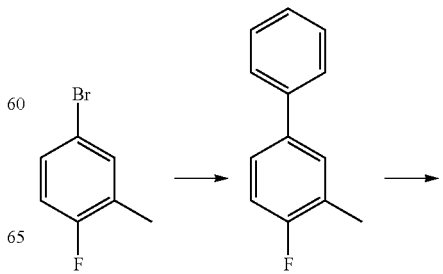

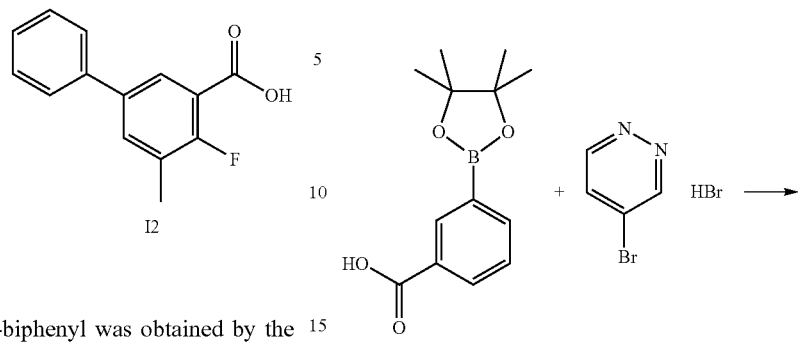

(i) 4-Fluoro-3-methyl-1,1'-biphenyl was obtained by the Suzuki coupling method D from 5-bromo-2-fluorotoluene as a colourless oil (5.90 g, 100%). $^1$H NMR (400 MHz, CDCl$_3$) δ 7.46-7.38 (m, 2H), 7.35-7.27 (m, 3H), 7.27-7.21 (m, 2H), 6.99-6.90 (m, 1H), 2.23 (d, J=1.9 Hz, 3H).

(ii) 4-Fluoro-5-methyl-[1,1'-biphenyl]-3-carboxylic acid was obtained by the carboxylation method from 4-fluoro-3-methyl-1,1'-biphenyl as a pale yellow solid (2.09 g, 33% yield). $^1$H NMR (400 MHz, DMSO) δ 13.29 (s, 1H), 7.88 (dd, J=6.4, 2.4 Hz, 1H), 7.83 (dd, J=6.4, 2.0 Hz, 1H), 7.72-7.61 (m, 2H), 7.49-7.45 (m, 2H), 7.40-7.37 (m, 1H), 2.34 (d, J=2.0 Hz, 3H). LCMS A rt 6.41 min, m/z 229.1 [M−H]$^−$.

(c) 3-Chloro-2-fluoro-5-(thiophen-2-yl)benzoic acid (I3)

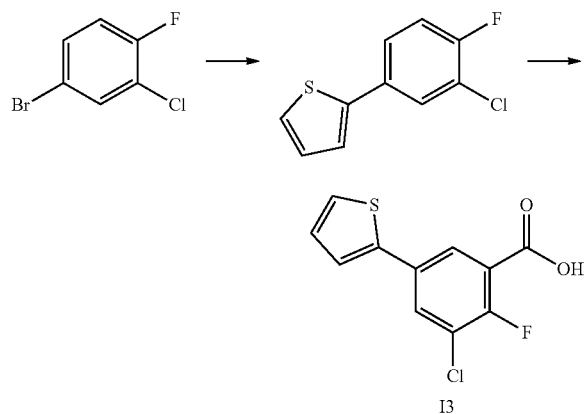

(i) 2-(3-Chloro-4-fluorophenyl)thiophene was obtained by the Suzuki coupling method D from 1-bromo-3-chloro-4-fluorobenzene as a colourless solid (347 mg, 28% yield). $^1$H NMR (400 MHz, CDCl$_3$) δ 7.61 (dd, J=6.9, 2.3 Hz, 1H), 7.43 (ddd, J=8.6, 4.5, 2.3 Hz, 1H), 7.28 (dd, J=5.1, 1.1 Hz, 1H), 7.23 (dd, J=3.6, 1.1 Hz, 1H), 7.13 (t, J=8.7 Hz, 1H), 7.06 (dd, J=5.1, 3.6 Hz, 1H).

(ii) 3-Chloro-2-fluoro-5-(thiophen-2-yl)benzoic acid was obtained by the carboxylation method from 2-(3-chloro-4-fluorophenyl)thiophene as an off white solid (64 mg, 39% yield). $^1$H NMR (400 MHz, DMSO) δ 13.25 (s, 1H), 8.02 (dd, J=7.0, 2.3 Hz, 1H), 7.80-7.67 (m, 2H), 7.65 (d, J=3.9 Hz, 1H), 7.51 (t, J=8.9 Hz, 1H).

(d) 3-(Pyridazin-4-yl)benzoic acid (I4)

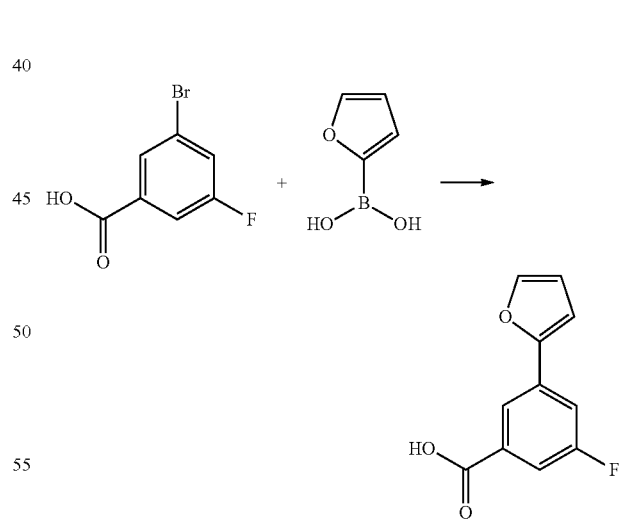

Following the Suzuki coupling method C, 3-(pyridazin-4-yl)benzoic acid was obtained as a pale brown solid (78% yield). $^1$H NMR (400 MHz, DMSO): δ 9.70-9.65 (m, 1H), 9.33-9.28 (m, 1H), 8.38 (s, 1H), 8.17 (d, J=7.8 Hz, 1H), 8.12-8.05 (m, 2H), 7.71 (t, J=7.8 Hz, 1H). Acid proton not observed. LCMS B rt 3.15 min, m/z 201.1 [M+H]$^+$.

(e) 3-Fluoro-5-(furan-2-yl)benzoic acid (I5)

Following the Suzuki coupling method A, 3-fluoro-5-(furan-2-yl)benzoic acid (I5I5) was obtained as a light brown solid (39% yield). $^1$H NMR (400 MHz, CDCl$_3$): δ 8.18 (t, J=1.4 Hz, 1H), 7.66 (ddd, J=8.8, 2.5, 1.4 Hz, 1H), 7.61 (ddd, J=9.4, 2.5, 1.5 Hz, 1H), 7.53-7.51 (m, 1H), 6.79 (dd, J=3.4, 0.8 Hz, 1H), 6.52 (dd, J=3.4, 1.8 Hz, 1H). LCMS B rt 3.65 min, m/z 205.1 [M−H]$^−$.

(f) 3-(Furan-2-yl)-5-methoxybenzoic acid (I6)

(h) 2-Phenylisonicotinic acid (I8)

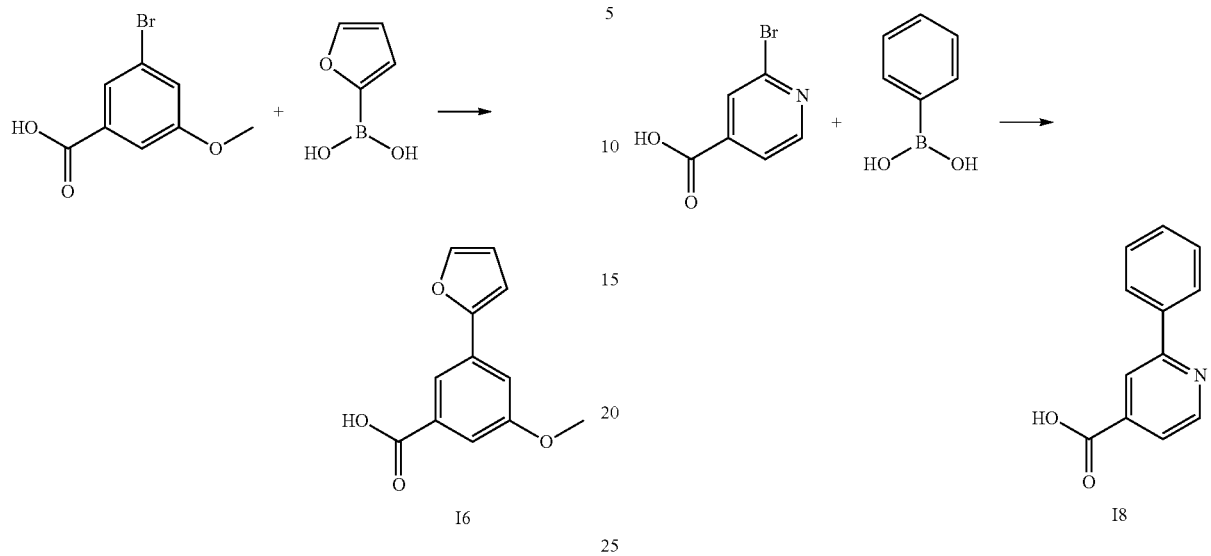

Following Suzuki coupling method A, 3-(furan-2-yl)-5-methoxybenzoic acid (I6A) was obtained as a light brown solid (71% yield). 25% of the material was starting acid. The material was used as is for the next step. ¹H NMR (400 MHz, CDCl₃): δ 8.01 (t, J=1.5, 1.5 Hz, 1H), 7.52 (dd, J=2.5, 1.4 Hz, 1H), 7.50 (dd, J=1.8, 0.7 Hz, 1H), 7.46 (dd, J=2.5, 1.5 Hz, 1H), 6.75 (dd, J=3.4, 0.8 Hz, 1H), 6.50 (dd, J=3.4, 1.8 Hz, 1H), 3.91 (s, 3H).

Following the Suzuki coupling method B, using Pd(PPh₃)₄, 2-phenylisonicotinic acid was isolated as a crude mixture with 30% of the starting acid present. Due to poor solubility, this was unable to be purified further, and the material was used as is for the next step.

(i) 2-Fluoro-5-(pyridazin-4-yl)benzoic acid (I9)

(g) 3-Chloro-5-(furan-2-yl)benzoic acid (I7)

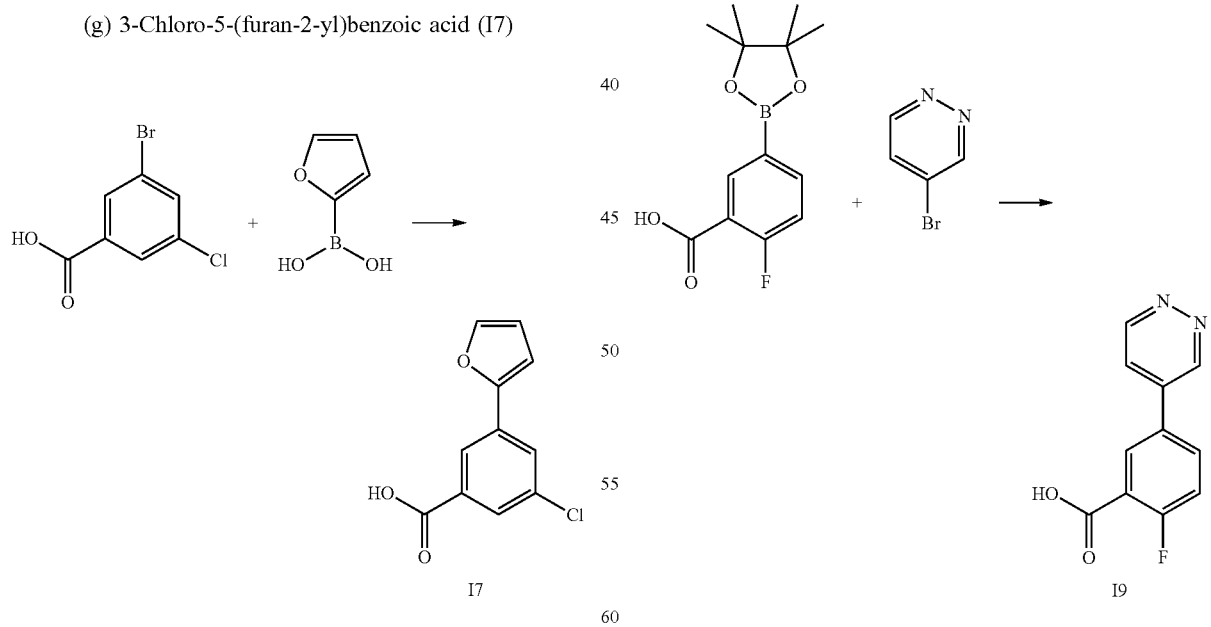

Following Suzuki coupling method A, using Pd(dppf)Cl₂, 3-chloro-5-(furan-2-yl)benzoic acid was obtained as a light brown solid (39% yield). ¹H NMR (400 MHz, DMSO): δ 8.15 (t, J=1.5, 1.5 Hz, 1H), 8.02 (t, J=1.9 Hz, 1H), 7.83 (d, J=2.0 Hz, 1H), 7.78 (t, J=1.9 Hz, 1H), 7.23 (d, J=3.4 Hz, 1H), 6.65 (dd, J=3.4, 1.8 Hz, 1H).

Following the Suzuki coupling method C, 2-fluoro-5-(pyridazin-4-yl)benzoic acid was obtained as a tan solid (21% yield). ¹H NMR (400 MHz, DMSO): δ 9.72 (dd, J=2.5, 1.2 Hz, 1H), 9.36 (dd, J=5.4, 1.2 Hz, 1H), 8.12 (dd, J=5.5, 2.5 Hz, 1H), 8.05-7.96 (m, 2H), 7.89 (dd, J=8.1, 1.8 Hz, 1H). LCMS B rt 3.12 min, m/z 219.1 [M+H]⁺.

(j) 5-Phenylnicotinic acid (I10)

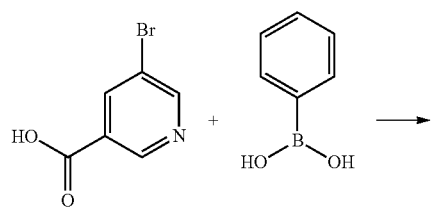

Following the Suzuki coupling method B, using Pd(dppf)Cl$_2$, 5-phenylnicotinic acid was obtained as a white solid (63% yield). $^1$H NMR (400 MHz, DMSO): δ 9.10 (d, J=18.2 Hz, 2H), 8.45 (t, J=1.8, 1.8 Hz, 1H), 7.80-7.76 (m, 2H), 7.55-7.29 (m, 3H). LCMS B rt 3.37 min, m/z 200.1 [M+H]$^+$.

(k) 3-Fluoro-5-propoxybenzoic acid (I11)

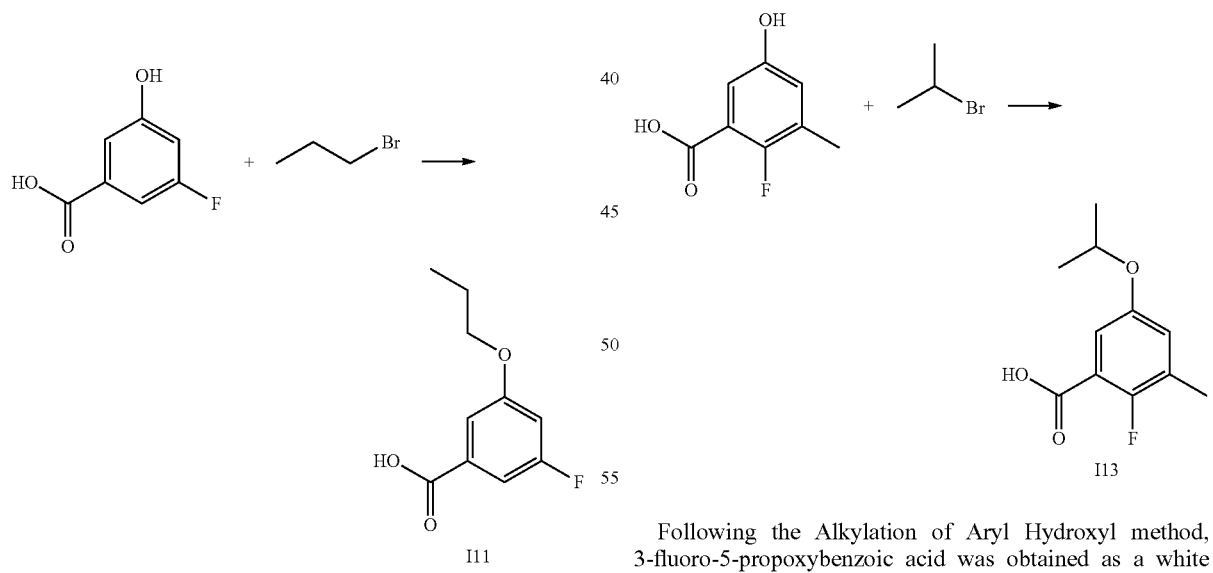

Following the Alkylation of Aryl Hydroxyl method, 3-fluoro-5-propoxybenzoic acid was obtained as a white solid (77% yield). $^1$H NMR (400 MHz, DMSO) δ 13.31 (s, 1H), 7.27 (dd, J=2.4, 1.3 Hz, 1H), 7.22 (ddd, J=8.9, 2.4, 1.3 Hz, 1H), 7.10 (dt, J=10.8, 2.4, 2.4 Hz, 1H), 3.99 (t, J=6.5, 6.5 Hz, 2H), 1.73 (h, J=7.4, 7.4, 7.4, 7.4, 7.4 Hz, 2H), 0.97 (t, J=7.4, 7.4 Hz, 3H). LCMS B rt 3.67 min, m/z 197.1 [M−H]$^−$.

(l) 2-Fluoro-3-methyl-5-propoxybenzoic acid (I12)

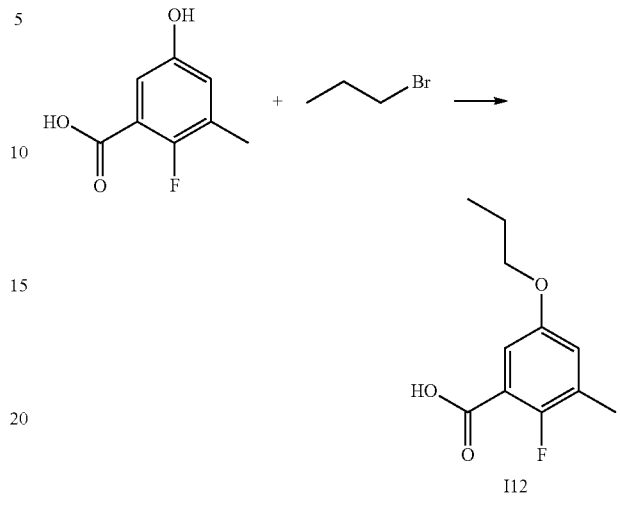

Following the Alkylation of Aryl Hydroxyl method, 3-fluoro-5-propoxybenzoic acid was obtained as a white solid (65% yield). $^1$H NMR (400 MHz, DMSO) δ 13.17 (s, 1H), 7.18-6.98 (m, 2H), 3.91 (t, J=6.5, 6.5 Hz, 2H), 2.23 (d, J=2.3 Hz, 3H), 1.70 (h, J=7.4, 7.4, 7.4, 7.4, 7.4 Hz, 2H), 0.96 (t, J=7.4, 7.4 Hz, 3H). LCMS B rt 3.68 min, m/z 213.1 [M+H]$^+$.

(m) 2-Fluoro-5-isopropoxy-3-methylbenzoic acid (I13)

Following the Alkylation of Aryl Hydroxyl method, 3-fluoro-5-propoxybenzoic acid was obtained as a white solid (59% yield). $^1$H NMR (400 MHz, DMSO): δ 13.16 (s, 1H), 7.19-6.91 (m, 2H), 4.56 (hept, J=6.0 Hz, 1H), 2.22 (d, J=2.1 Hz, 3H), 1.24 (d, J=6.0 Hz, 6H). LCMS B r.t. 3.63, m/z 213.1 [M+H]$^+$.

(n) Substituted Benzoic Acids I

The following compounds were made by the Ullmann transformation method A:

| | Structure | Starting material | Product details |
|---|---|---|---|
| A1 | 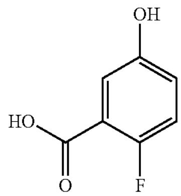 [SMILES: O=C(O)c1cc(O)ccc1F] | 5-bromo-2-fluorobenzoic acid (3.5 g, 15.98 mmol) | Off white solid (2.16 g, 87% yield). $^1$H NMR (400 MHz, DMSO) δ 7.18 (dd, J = 6.0, 3.2 Hz, 1H), 7.09 (dd, J = 10.5, 8.9 Hz, 1H), 6.98-6.93 (m, 1H). LCMS B rt 3.19 min, m/z 157.1 [M + H]$^+$. |
| A2 | 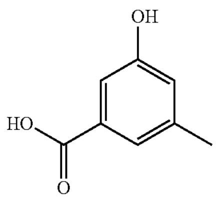 | 3-bromo-5-methylbenzoic acid (0.2, 5.82 mmol) | White solid (0.141, 100% yield). $^1$H NMR (400 MHz, DMSO) δ 7.82 (s, 1H), 7.74 (s, 1H), 7.67 (s, 1H), 2.36 (s, 3H). LCMS B rt 3.63 min, m/z 151.0 [M − H]$^-$. |
| A3 | 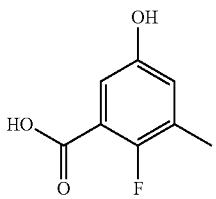 | 5-bromo-2-fluoro-3-methylbenzoic acid (0.47, 2.01 mmol) | White solid (0.301 g, 83% yield). $^1$H NMR (400 MHz, DMSO) δ 7.75 (d, J = 5.8 Hz, 2H), 2.26 (d, J = 1.8 Hz, 3H). LCMS A rt 6.09 min, m/z 171.1 [M + H]$^+$. |
| A4 | 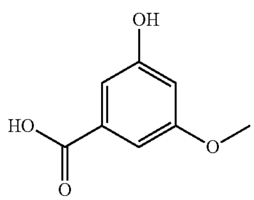 | 3-bromo-5-methoxybenzoic acid (0.65 g, 2.8 mmol) | White solid (0.457 g, 97% yield). $^1$H NMR (400 MHz, DMSO) δ 6.96 (s, 1H), 6.91 (s, 1H), 6.54 (t, J = 2.2 Hz, 1H), 3.73 (s, 3H). LCMS B, rt 3.25 min, m/z 167.1 [M − H]$^-$. |
| A5 | 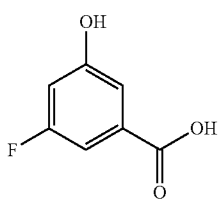 [SMILES: O=C(O)c1cc(O)cc(F)c1] | | Off white solid (0.540 g, 85% yield). $^1$H NMR (400 MHz, DMSO) δ 7.20 (dd, J = 2.1, 1.4 Hz, 1H), 7.09 (ddd, J = 9.2, 2.4, 1.3 Hz, 1H), 6.81 (dt, J = 10.6, 2.4 Hz, 1H). LCMS B rt 3.29 min, m/z 155.1 [M + H]$^+$. |

(o) Substituted Benzoic Acids II

The following compounds were made by the Alkylation of Aryl Hydroxyl method:

| | Structure | Starting material | Product details |
|---|---|---|---|
| A5 | 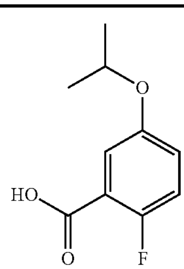 | A1 (0.2 g, 1.28 mmol) | Off white solid (0.212, 84% yield). $^1$H NMR (400 MHz, DMSO) δ 7.27 (dd, J = 5.9, 3.1 Hz, 1H), 7.23-7.12 (m, 2H), 4.71-4.47 (m, 1H), 1.24 (d, J = 6.0 Hz, 6H). LCMS B rt 3.53 min, m/z 199.1 [M + H]$^+$. |

-continued

| | Structure | Starting material | Product details |
|---|---|---|---|
| A6 | 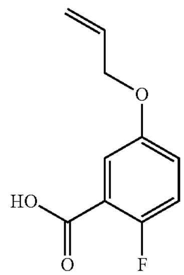 | A1 (0.350 g, 2.24 mmol) | White solid (0.271 g, 62% yield). ¹H NMR (400 MHz, DMSO) δ 7.32 (dd, J = 5.6, 3.0 Hz, 1H), 7.26-7.16 (m, 2H), 6.02 (ddt, J = 17.3, 10.4, 5.2 Hz, 1H), 5.39 (dq, J = 17.3, 1.7 Hz, 1H), 5.26 (ddd, J = 10.5, 3.1, 1.5 Hz, 1H), 4.59 (dt, J = 5.2, 1.5 Hz, 2H). LCMS A rt 5.84 min, m/z 197.0 [M + H]⁺. |
| A7 | 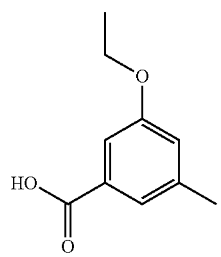 | A2 (0.2 g, 5.82 mmol) | White solid (0.141, 100% yield). ¹H NMR (400 MHz, DMSO) δ 7.34 (s, 1H), 7.22 (s, 1H), 6.98 (s, 1H), 4.04 (q, J = 7.0 Hz, 2H), 2.31 (s, 3H), 1.32 (t, J = 7.0 Hz, 3H). LCMS A rt 6.01 min, m/z 181.1 [M + H]⁺. |
| A8 | 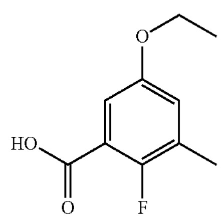 | A3 (0.18 g, 1.06 mmol) | White solid (0.301 g, 83% yield). ¹H NMR (400 MHz, DMSO) δ 7.19-6.93 (m, 2H), 4.01 (q, J = 7.0 Hz, 2H), 2.22 (d, J = 2.3 Hz, 3H), 1.30 (t, J = 7.0 Hz, 3H). LCMS A, rt 5.97 min, m/z 199.07 [M + H]⁺. |
| A9 | 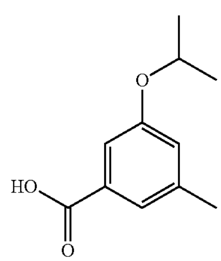 | A2 (0.15 g, 0.99 mmol) | White solid (0.185 g, 97% yield). ¹H NMR (400 MHz, DMSO) δ 7.32 (s, 1H), 7.20 (s, 1H), 6.97 (s, 1H), 4.62 (dt, J = 12.0, 6.0 Hz, 1H), 2.31 (s, 3H), 1.26 (d, J = 6.0 Hz, 6H). LCMS B rt 3.56 min, m/z 193.1 [M − H]⁻. |
| A10 | 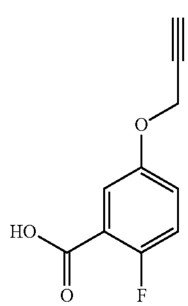 | A1 (0.150 g, 0.96 mmol) | White solid (0.091 g, 49% yield). ¹H NMR (400 MHz, DMSO) δ 7.39 (dd, J = 5.5, 3.0 Hz, 1H), 7.33-7.18 (m, 2H), 4.84 (d, J = 2.4 Hz, 2H), 3.60 (t, J = 2.4 Hz, 1H). LCMS B rt 3.42 min, m/z 195.1 [M + H]⁺. |
| A11 | 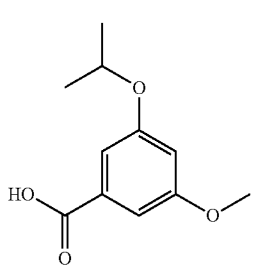 | A4 (0.150 g, 2.2 mmol) | White solid (0.178 g, 39% yield). ¹H NMR (400 MHz, DMSO) δ 7.02 (d, J = 2.2 Hz, 1H), 6.69 (t, J = 2.2 Hz, 2H), 4.73-4.56 (m, 1H), 3.77 (s, 3H), 1.26 (d, J = 6.0 Hz, 6H). LCMS A rt 6.06 min, m/z 211.2 [M + H]⁺. |

-continued

| | Structure | Starting material | Product details |
|---|---|---|---|
| A12 | (3-ethoxy-5-methoxybenzoic acid structure) | A4 (0.15 g, 0.82 mmol) | White solid (0.161 g, 92% yield). $^1$H NMR (400 MHz, DMSO) δ 7.06-7.02 (m, 2H), 6.71 (d, J = 2.3 Hz, 1H), 4.04 (q, J = 7.0 Hz, 2H), 3.77 (s, 3H), 1.32 (t, J = 7.0 Hz, 3H). LCMS A rt 5.83 min, m/z 197.1 [M + H]$^+$. |
| A13 | (5-ethoxy-2-fluorobenzoic acid structure) | A1 (0.125 g, 0.9 mmol) | White solid (0.142 g, 86% yield). $^1$H NMR (400 MHz, DMSO) δ 7.28 (dd, J = 5.8, 3.2 Hz, 1H), 7.25-7.13 (m, 2H), 4.03 (q, J = 6.9 Hz, 2H), 1.31 (t, J = 6.9 Hz, 3H). LCMS B rt 3.46 min, m/z 185.0 [M + H]$^+$. |
| A14 | (3-allyloxybenzoic acid structure) | 3-hydroxybenzoic acid | Colourless solid (75% yield). $^1$H NMR (400 MHz, DMSO) δ 7.53 (d, J = 7.7 Hz, 1H), 7.45 (dd, J = 2.4, 1.5 Hz, 1H), 7.41 (t, J = 7.9 Hz, 1H), 7.22-7.18 (m, 1H), 6.04 (ddt, J = 17.2, 10.4, 5.1 Hz, 1H), 5.40 (ddd, J = 17.3, 3.3, 1.6 Hz, 1H), 5.27 (dd, J = 10.6, 1.5 Hz, 1H), 4.62 (dt, J = 5.1, 1.4 Hz, 2H). LCMS B rt 3.41 min, m/z 177.1 [M − H]$^-$. |
| A15 | (3-cyclopropoxy-5-methylbenzoic acid structure) | A2 | Colourless solid (24% yield). $^1$H NMR (400 MHz, DMSO) δ 7.83 (s, 1H), 7.75 (s, 1H), 7.68 (s, 1H), 3.88 (dq, J = 8.9, 2.9 Hz, 1H), 2.33 (s, 3H), 0.79 (dd, J = 9.6, 3.8 Hz, 2H), 0.66 (dt, J = 8.0, 3.9 Hz, 2H). LCMS B rt 3.59 min: m/z 191.1 [M − H]$^-$. |

(p) Substituted Boronic Acids

The following compounds were made by the Suzuki coupling method E:

| | Structure | Starting material | Product details |
|---|---|---|---|
| B1 | (3-(4,4,5,5-tetramethyl-1,3,2-dioxaborolan-2-yl)benzoic acid structure) | (3-bromobenzoic acid structure) | Faint brown solid (89%). $^1$H NMR (400 MHz, CDCl$_3$) δ 8.57 (s, 1H), 8.19 (ddd, J = 21.9, 11.8, 10.1 Hz, 1H), 8.09-7.98 (m, 1H), 7.57-7.38 (m, 1H), 1.37 (s, 12H). $^{13}$C NMR (101 MHz, CDCl$_3$) δ 171.66, 139.98, 136.60, 132.84, 128.71, 127.93, 84.21, 24.89. LCMS B rt 3.67 min, m/z 249.2 [M + H]$^+$. |

-continued

| | Structure | Starting material | Product details |
|---|---|---|---|
| B2 | 3,5-dimethylphenyl Bpin CO2H | 3-bromo-5-methylbenzoic acid | Beige solid (93% yield). $^1$H NMR (400 MHz, CDCl$_3$) δ 8.36 (s, 1H), 8.01 (s, 1H), 7.86 (s, 1H), 2.42 (s, 3H), 1.36 (s, 12H). LCMS B rt 3.76 min, m/z 263.2 [M + H]$^+$. |
| B3 | 4-fluoro-3-(Bpin)benzoic acid | 5-bromo-2-fluorobenzoic acid | Faint red solid (76% yield). $^1$H NMR (400 MHz, CDCl$_3$) δ 8.50 (d, J = 7.5 Hz, 1H), 8.06-7.93 (m, 1H), 7.22-7.10 (m, 1H), 1.36 (s, 12H). LCMS B rt 3.67 min, m/z 267.1 [M + H]$^+$. |
| B4 | 2-fluoro-3-methyl-5-(Bpin)benzoic acid | 5-bromo-2-fluoro-3-methylbenzoic acid | Faint brown solid (66% yield). 1H NMR (400 MHz, CDCl3) δ 8.16 (s, 1H), 7.70 (dd, J = 2.5, 1.5 Hz, 1H), 3.88 (s, 3H), 1.36 (s, 12H). LCMS B rt 3.85 min, m/z 281.1 [M + H]$^+$. |
| B5 | 3-fluoro-5-(Bpin)benzoic acid | 3-bromo-5-fluorobenzoic acid | Faint brown solid (86% yield). 1H NMR (400 MHz, CDCl3) δ 8.16 (s, 1H), 7.70 (dd, J = 2.5, 1.5 Hz, 1H), 7.57 (d, J = 2.3 Hz, 1H), 1.36 (s, 12H). LCMS B rt 3.69 min, m/z 279.2 [M + H]$^+$. |
| B6 | 3-methoxy-5-(Bpin)benzoic acid | 3-bromo-5-methoxybenzoic acid | Faint brown solid (86% yield). 1H NMR (400 MHz, CDCl3) δ 8.16 (s, 1H), 7.70 (dd, J = 2.5, 1.5 Hz, 1H), 7.57 (d, J = 2.3 Hz, 1H), 3.88 (s, 3H), 1.36 (s, 12H). LCMS B rt 3.69 min, m/z 279.2 [M + H]$^+$. |

(q) 2-Pyridine Acids

The following compounds were made by Suzuki Coupling F:

| | Structure | Starting material | Product details |
|---|---|---|---|
| P1 | 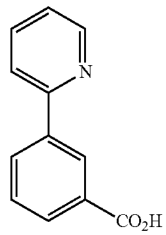 [SMILES: O=C(O)c1cccc(-c2ccccn2)c1] | B1 | Off white solid (75% yield). $^1$H NMR (400 MHz, DMSO) δ 8.71-8.68 (m, 1H), 8.67 (s, 1H), 8.29 (d, J = 7.8 Hz, 1H), 8.01 (t, J = 8.4 Hz, 2H), 7.91 (td, J = 7.8, 1.8 Hz, 1H), 7.61 (t, J = 7.7 Hz, 1H), 7.42-7.37 (m, 1H). LCMS B rt 3.17, m/z 200.1 [M + H]$^+$. |
| P2 | 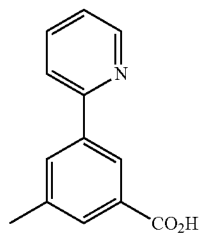 [SMILES: Cc1cc(C(=O)O)cc(-c2ccccn2)c1] | B2 | Colourless solid (70% yield). $^1$H NMR (400 MHz, DMSO) δ 8.70-8.67 (m, 1H), 8.46 (s, 1H), 8.14 (s, 1H), 8.01 (d, J = 8.0 Hz, 1H), 7.90 (td, J = 7.7, 1.8 Hz, 1H), 7.83 (s, 1H), 7.38 (ddd, J = 7.4, 4.8, 0.9 Hz, 1H), 2.45 (s, 3H). LCMS B rt 3.36 min, m/z 214.1 [M + H]$^+$. |
| P3 | 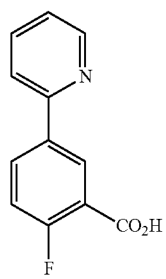 [SMILES: O=C(O)c1cc(-c2ccccn2)ccc1F] | B3 | Colourless solid (47% yield). $^1$H NMR (400 MHz, DMSO) δ 8.69 (ddd, J = 4.8, 1.7, 0.9 Hz, 1H), 8.61 (dd, J = 7.2, 2.5 Hz, 1H), 8.33 (ddd, J = 8.7, 4.6, 2.5 Hz, 1H), 8.02 (d, J = 8.0 Hz, 1H), 7.91 (td, J = 7.8, 1.8 Hz, 1H), 7.48-7.37 (m, 2H). LCMS B rt 3.37 min, m/z 218.1 [M + H]$^+$. |
| P4 | 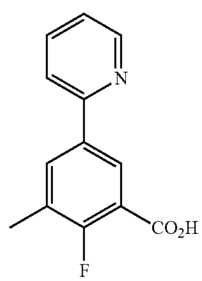 [SMILES: Cc1cc(-c2ccccn2)cc(C(=O)O)c1F] | B4 | Faint yellow solid (80% yield). $^1$H NMR (400 MHz, DMSO) δ 8.67 (ddd, J = 4.8, 1.7, 0.9 Hz, 1H), 8.39 (dd, J = 6.6, 2.3 Hz, 1H), 8.23 (dd, J = 6.3, 2.2 Hz, 1H), 7.99 (d, J = 8.0 Hz, 1H), 7.93-7.87 (m, 1H), 7.37 (ddd, J = 7.4, 4.8, 1.0 Hz, 1H), 2.35 (d, J = 2.1 Hz, 3H). LCMS B rt 3.37 min, m/z 232.2 [M + H]$^+$. |
| P5 | 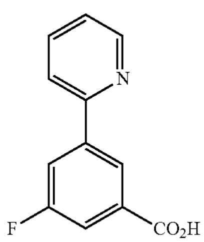 [SMILES: O=C(O)c1cc(F)cc(-c2ccccn2)c1] | B5 | Beige solid (54% yield). $^1$H NMR (400 MHz, DMSO) δ 8.72 (ddd, J = 4.8, 1.7, 0.9 Hz, 1H), 8.55 (t, J = 1.5 Hz, 1H), 8.18 (ddd, J = 10.1, 2.5, 1.6 Hz, 1H), 8.11 (d, J = 8.0 Hz, 1H), 7.95 (td, J = 7.8, 1.8 Hz, 1H), 7.73 (ddd, J = 8.9, 2.5, 1.4 Hz, 1H), 7.45 (ddd, J = 7.5, 4.8, 0.9 Hz, 1H). LCMS B rt 3.41 min, m/z 218.1 [M + H]$^+$. |
| P6 | 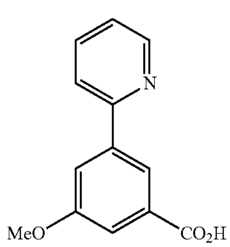 | B6 | Beige solid (62% yield). $^1$H NMR (400 MHz, DMSO) δ 8.70 (d, J = 4.0 Hz, 1H), 8.27 (s, 1H), 8.05 (d, J = 8.0 Hz, 1H), 7.92 (td, J = 7.8, 1.7 Hz, 1H), 7.87 (s, 1H), 7.51 (s, 1H), 7.41 (dd, J = 6.8, 4.9 Hz, 1H), 3.90 (s, 3H). LCMS B rt 3.27 min, m/z 230.2 [M + H]$^+$. |

(r) 2-Pyrimidine Acids

The following compounds were made by Suzuki Coupling F:

| | Structure | Starting material | Product details |
|---|---|---|---|
| P7 | 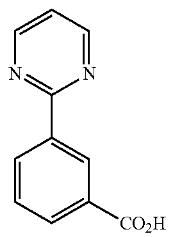 | B1 | Off-white solid (79%) yield. $^1$H NMR (400 MHz, DMSO) δ 8.99 (t, J = 1.5 Hz, 1H), 8.95 (d, J = 4.9 Hz, 2H), 8.61 (d, J = 7.9 Hz, 1H), 8.09 (d, J = 7.7 Hz, 1H), 7.68 (d, J = 7.8 Hz, 1H), 7.50 (t, J = 4.9 Hz, 1H). LCMS B rt 2.96 min, m/z 201.1 [M + H]$^+$. |
| P8 | 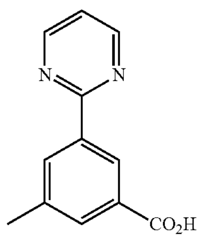 [SMILES: Cc1cc(C(=O)O)cc(-c2ncccn2)c1] | B2 | Beige solid (70% yield). $^1$H NMR (400 MHz, DMSO) δ 8.93 (d, J = 4.9 Hz, 2H), 8.79 (d, J = 0.4 Hz, 1H), 8.44 (d, J = 0.7 Hz, 1H), 7.91 (d, J = 0.7 Hz, 1H), 7.49 (d, J = 4.9 Hz, 1H), 2.47 (s, 3H). LCMS B rt 215.1 min, m/z 215.1 [M + H]$^+$. |
| P9 | 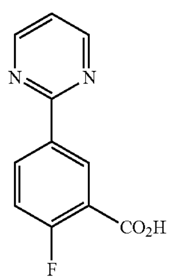 [SMILES: O=C(O)c1cc(-c2ncccn2)ccc1F] | B3 | Beige solid (78% yield). $^1$H NMR (400 MHz, DMSO) δ 8.92 (d, J = 4.8 Hz, 2H), 8.90 (d, J = 2.3 Hz, 1H), 8.59 (ddd, J = 8.6, 4.6, 2.4 Hz, 1H), 7.51-7.42 (m, 2H). LCMS B rt 3.41 min, m/z 219.1 [M + H]$^+$. |
| P10 | 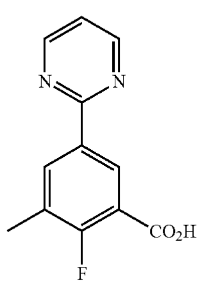 [SMILES: Cc1cc(-c2ncccn2)cc(C(=O)O)c1F] | B4 | Beige solid (89% yield). $^1$H NMR (400 MHz, DMSO) δ 8.92 (d, J = 4.9 Hz, 2H), 8.72 (dd, J = 6.8, 2.3 Hz, 1H), 8.49 (dd, J = 6.7, 1.7 Hz, 1H), 7.48 (t, J = 4.9 Hz, 1H), 2.37 (d, J = 2.1 Hz, 3H). LCMS B rt 3.49 min, m/z 233.1 [M + H]$^+$. |
| P11 | 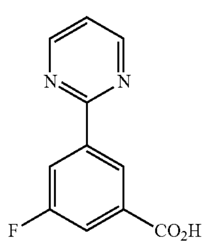 [SMILES: O=C(O)c1cc(F)cc(-c2ncccn2)c1] | B5 | Beige solid (60% yield). $^1$H NMR (400 MHz, DMSO) δ 8.95-8.89 (m, 3H), 8.59 (ddd, J = 8.6, 4.7, 2.4 Hz, 1H), 7.52-7.43 (m, 2H). LCMS B rt 3.40 min, m/z 219.1 [M + H]$^+$. |

-continued

| | Structure | Starting material | Product details |
|---|---|---|---|
| P12 | (pyrimidine attached to benzene ring with MeO and CO₂H substituents) | B6 | Beige solid (65% yield). ¹H NMR (400 MHz, DMSO) δ 8.95 (d, J = 4.9 Hz, 2H), 8.60 (t, J = 1.5 Hz, 1H), 8.14 (dd, J = 2.7, 1.5 Hz, 1H), 7.59 (dd, J = 2.7, 1.4 Hz, 1H), 7.51 (t, J = 4.9 Hz, 1H), 3.90 (s, 3H). LCMS B rt 3.43 min, m/z 231.1 [M + H]⁺. |

(s) 1H-Pyrazole Acids

The following compounds were made by the Ullmann coupling method B:

| | Structure | Starting material | Product details |
|---|---|---|---|
| P13 | (1-phenylpyrazole with CO₂H) | 3-bromobenzoic acid | Colourless solid (39% yield). ¹H NMR (400 MHz, DMSO) δ 8.61 (d, J = 2.5 Hz, 1H), 8.40-8.35 (m, 1H), 8.12-8.07 (m, 1H), 7.86 (dd, J = 7.7, 1.1 Hz, 1H), 7.79 (d, J = 1.6 Hz, 1H), 7.63 (t, J = 7.9 Hz, 1H), 6.59-6.55 (m, 1H). LCMS B rt 3.32 min, m/z 189.1 [M + H]⁺. |
| P14 | (1-(3-methylphenyl)pyrazole with CO₂H) | 3-bromo-5-methylbenzoic acid | Colourless solid (53% yield). ¹H NMR (400 MHz, DMSO) δ 8.17 (s, 1H), 7.94 (d, J = 5.0 Hz, 2H), 7.76 (d, J = 1.4 Hz, 1H), 7.68 (s, 1H), 6.55 (d, J = 1.8 Hz, 1H), 2.44 (s, 3H). LCMS B rt 3.44 min, m/z 203.1 [M + H]⁺. |
| P15 | (1-(4-fluoro-3-carboxyphenyl)pyrazole) | 5-bromo-2-fluorobenzoic acid | Colourless solid (43% yield). ¹H NMR (400 MHz, DMSO) δ 8.56 (d, J = 2.0 Hz, 1H), 8.26 (dd, J = 5.8, 2.5 Hz, 1H), 8.10-8.01 (m, 1H), 7.77 (s, 1H), 7.45 (t, J = 9.6 Hz, 1H), 6.56 (s, 1H). LCMS B rt 3.34 min, m/z 207.1 [M + H]⁺. |
| P16 | (1-(3-methyl-4-fluoro-5-carboxyphenyl)pyrazole) | 5-bromo-2-fluoro-3-methylbenzoic acid | Colourless solid (52% yield). ¹H NMR (400 MHz, DMSO) δ 8.54 (d, J = 2.4 Hz, 1H), 8.09 (s, 1H), 8.02 (s, 1H), 7.76 (d, J = 1.6 Hz, 1H), 6.58-6.54 (m, 1H), 2.35 (s, 3H). LCMS B rt 3.41 min, m/z 221.2 [M + H]⁺. |

| | Structure | Starting material | Product details |
|---|---|---|---|
| P17 | 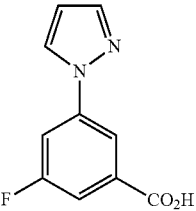 | 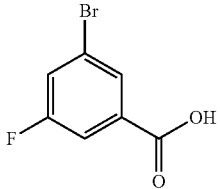 | Colourless solid (67% yield). $^1$H NMR (400 MHz, DMSO) δ 8.65 (s, 1H), 8.27 (s, 1H), 8.02 (d, J = 9.5 Hz, 1H), 7.80 (s, 1H), 7.57 (s, 1H), 6.59 (s, 1H). LCMS B rt 3.45 min, m/z 207.1 [M + H]$^+$. |
| P18 | 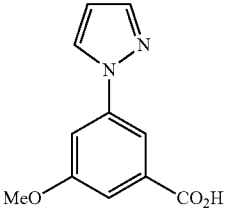 [SMILES: COc1cc(C(=O)O)cc(-n2cccn2)c1] | 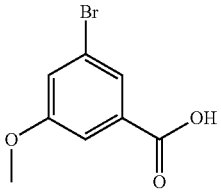 | Off white solid (59% yield). $^1$H NMR (400 MHz, DMSO) δ 8.63 (d, J = 2.3 Hz, 1H), 7.99 (s, 1H), 7.77 (d, J = 1.5 Hz, 1H), 7.65 (t, J = 2.0 Hz, 1H), 7.36 (d, J = 1.1 Hz, 1H), 6.56 (dd, J = 2.5, 1.8 Hz, 1H), 3.88 (s, 3H). LCMS B rt 3.41 min, m/z 219.1 [M + H]$^+$. |

(t) 3-Methyl-1H-Pyrazole acids

The following compounds were made by the Ullmann coupling method B:

| | Structure | Starting material | Product details |
|---|---|---|---|
| P19 | 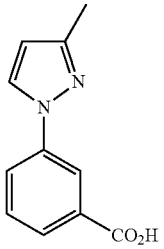 | 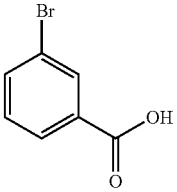 | Colourless solid (49% yield). $^1$H NMR (400 MHz, DMSO) δ 8.47 (d, J = 2.4 Hz, 1H), 8.34 (s, 1H), 8.03 (dd, J = 8.0, 1.6 Hz, 1H), 7.82 (d, J = 7.7 Hz, 1H), 7.59 (t, J = 7.9 Hz, 1H), 6.36 (d, J = 2.4 Hz, 1H), 2.29 (s, 3H). LCMS B rt 3.45 min, m/z 203.1 [M + H]$^+$. |
| P20 | 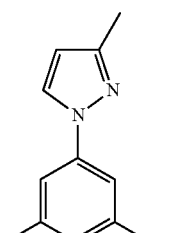 | 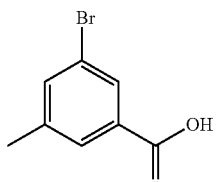 | Colourless solid (35% yield). $^1$H NMR (400 MHz, DMSO) δ 8.44 (d, J = 2.4 Hz, 1H), 8.12 (s, 1H), 7.87 (s, 1H), 7.63 (d, J = 0.7 Hz, 1H), 6.34 (d, J = 2.4 Hz, 1H), 2.42 (s, 3H), 2.27 (s, 3H). LCMS B rt 3.55 min, m/z 217.1 [M + H]$^+$. |
| P21 | 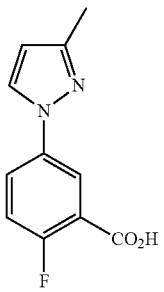 [SMILES: Cc1ccn(-c2ccc(F)c(C(=O)O)c2)n1] | 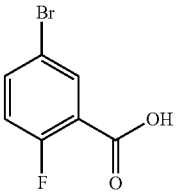 [SMILES: O=C(O)c1cc(Br)ccc1F] | Off-white solid (38% yield). $^1$H NMR (400 MHz, DMSO) δ 8.43 (d, J = 2.4 Hz, 1H), 8.22 (dd, J = 6.3, 2.9 Hz, 1H), 8.02 (ddd, J = 9.0, 3.9, 3.1 Hz, 1H), 7.43 (dd, J = 10.2, 9.1 Hz, 1H), 6.35 (d, J = 2.4 Hz, 1H), 2.27 (s, 3H). LCMS B rt 3.42, m/z 221.2 [M + H]$^+$. |

| | Structure | Starting material | Product details |
|---|---|---|---|
| P22 | 3-methyl-5-(3-methyl-1H-pyrazol-1-yl)-2-fluorobenzoic acid structure | 5-bromo-3-methyl-2-fluorobenzoic acid | Colourless solid (40% yield). $^1$H NMR (400 MHz, DMSO) δ 8.39 (d, J = 2.4 Hz, 1H), 8.02 (dd, J = 5.7, 2.9 Hz, 1H), 7.95 (dd, J = 5.5, 2.8 Hz, 1H), 6.33 (d, J = 2.3 Hz, 1H), 2.32 (d, J = 2.0 Hz, 3H), 2.26 (s, 3H). LCMS B rt 3.53 min, m/z 235.1 [M + H]$^+$. |
| P23 | 3-fluoro-5-(3-methyl-1H-pyrazol-1-yl)benzoic acid structure | 3-bromo-5-fluorobenzoic acid | Colourless solid (43%). $^1$H NMR (400 MHz, DMSO) δ 8.54 (d, J = 2.4 Hz, 1H), 8.23-8.19 (m, 1H), 7.96 (dt, J = 10.3, 2.3 Hz, 1H), 7.53 (ddd, J = 8.8, 2.4, 1.3 Hz, 1H), 6.39 (s, 1H), 2.28 (s, 3H). LCMS B rt 3.15 min, m/z 221.1 [M + H]$^+$. |
| P24 | 3-methoxy-5-(3-methyl-1H-pyrazol-1-yl)benzoic acid structure | 3-bromo-5-methoxybenzoic acid | Colourless solid (50% yield). $^1$H NMR (400 MHz, DMSO) δ 8.49 (d, J = 2.4 Hz, 1H), 7.95-7.90 (m, 1H), 7.58 (t, J = 2.2 Hz, 1H), 7.31 (dd, J = 2.2, 1.3 Hz, 1H), 6.34 (d, J = 2.4 Hz, 1H), 3.87 (s, 3H), 2.27 (s, 3H). LCMS B rt 3.51 min, m/z 233.1 [M + H]$^+$. |

(u) 4-Methyl-1H-Pyrazole Acids

The following compounds were made by the Ullmann coupling method B:

| | Structure | Starting material | Product details |
|---|---|---|---|
| P25 | 3-(4-methyl-1H-pyrazol-1-yl)benzoic acid structure | 3-bromobenzoic acid | Off-white solid (49% yield). $^1$H NMR (400 MHz, DMSO) δ 8.36 (s, 1H), 8.33-8.30 (m, 1H), 8.02 (ddd, J = 8.1, 2.3, 1.0 Hz, 1H), 7.84-7.80 (m, 1H), 7.62-7.57 (m, 2H), 2.10 (s, 3H). LCMS B rt 3.45 min, m/z 203.1 [M + H]$^+$. |
| P26 | 3-methyl-5-(4-methyl-1H-pyrazol-1-yl)benzoic acid structure | 3-bromo-5-methylbenzoic acid | Colourless solid (42% yield). $^1$H NMR (400 MHz, DMSO) δ 8.33 (s, 1H), 8.11 (d, J = 1.4 Hz, 1H), 7.86 (s, 1H), 7.64 (d, J = 0.7 Hz, 1H), 7.57 (s, 1H), 2.42 (s, 3H), 2.09 (s, 3H). LCMS B rt 3.53 min, m/z 217.1 [M + H]$^+$. |

| | Structure | Starting material | Product details |
|---|---|---|---|
| P27 | 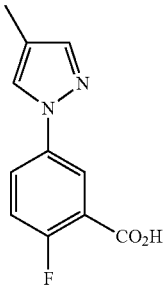 [SMILES: Cc1cnn(-c2ccc(F)c(C(=O)O)c2)c1] | 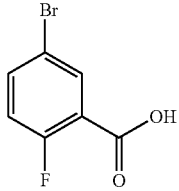 [SMILES: O=C(O)c1cc(Br)ccc1F] | Off-white solid (20% yield?). $^1$H NMR (400 MHz, DMSO) δ 8.32 (s, 1H), 8.20 (dd, J = 6.3, 2.9 Hz, 1H), 8.00 (ddd, J = 9.0, 3.9, 3.1 Hz, 1H), 7.58 (s, 1H), 7.43 (dd, J = 10.2, 9.0 Hz, 1H), 2.09 (s, 3H). LCMS B rt 3.44 min, m/z 221.1 [M + H]$^+$. |
| P28 | 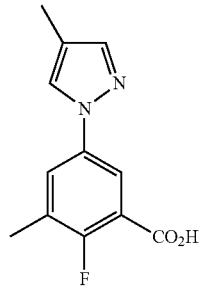 [SMILES: Cc1cnn(-c2cc(C)c(F)c(C(=O)O)c2)c1] | 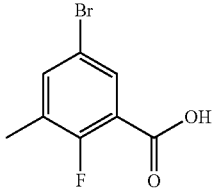 | Colourless solid (43% yield). $^1$H NMR (400 MHz, DMSO) δ 8.29 (s, 1H), 8.01 (dd, J = 5.8, 2.9 Hz, 1H), 7.94 (dd, J = 5.6, 2.7 Hz, 1H), 7.56 (s, 1H), 2.32 (d, J = 2.2 Hz, 3H), 2.09 (s, 3H). LCMS B rt 3.56 min, m/z 235.1 [M + H]$^+$. |
| P29 | 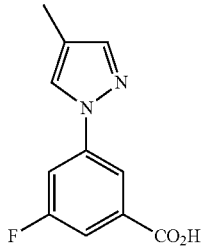 | 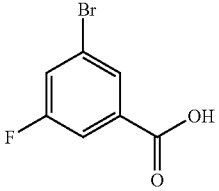 | Colourless solid (45% yield). $^1$H NMR (400 MHz, DMSO) δ 8.43 (s, 1H), 8.19 (s, 1H), 7.93 (d, J = 10.1 Hz, 1H), 7.63 (s, 1H), 7.53 (d, J = 8.0 Hz, 1H), 2.09 (s, 3H). LCMS B rt 3.55 min, m/z 221.1 [M + H]$^+$. |

(v) 4-Fluoro-1H-Pyrazole Acids

The following compounds were made by the Ullmann coupling method B:

| | Structure | Starting material | Product details |
|---|---|---|---|
| P30 | 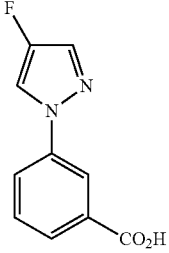 | 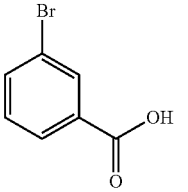 | Off-white solid (49% yield). $^1$H NMR (400 MHz, DMSO) δ 8.83 (dd, J = 4.5, 0.6 Hz, 1H), 8.34-8.31 (m, 1H), 8.04 (ddd, J = 8.2, 2.4, 1.0 Hz, 1H), 7.90-7.85 (m, 2H), 7.64 (t, J = 7.9 Hz, 1H). LCMS B rt 3.47 min, m/z 207.1 [M + H]$^+$. |

|    | Structure | Starting material | Product details |
|----|-----------|-------------------|-----------------|
| P31 | 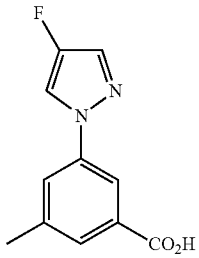 [SMILES: Cc1cc(C(=O)O)cc(-n2cc(F)cn2)c1] | | Colourless solid (42% yield). ¹H NMR (400 MHz, DMSO) δ 8.75 (dd, J = 4.5, 0.5 Hz, 1H), 8.12 (s, 1H), 7.87-7.783 (m, 2H), 7.69 (d, J = 0.6 Hz, 1H), 2.42 (s, 3H). LCMS B rt 3.52 min, m/z 221.1 [M + H]⁺. |
| P32 | 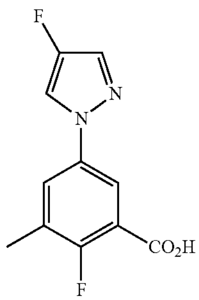 [SMILES: Cc1cc(-n2cc(F)cn2)cc(C(=O)O)c1F] | | Colourless solid (40% yield). ¹H NMR (400 MHz, DMSO) δ 8.74 (d, J = 4.5 Hz, 1H), 8.03 (dd, J = 5.5, 2.9 Hz, 1H), 7.98-7.93 (m, 1H), 7.86 (d, J = 4.2 Hz, 1H), 2.33 (d, J = 2.2 Hz, 3H). LCMS B rt 3.54 min, m/z 239.1 [M + H]⁺. |

(w) 5-Methyl-1H-Pyrazole Acids

The following compounds were made by the Ullmann coupling method B:

|    | Structure | Starting material | Product details |
|----|-----------|-------------------|-----------------|
| P33 | 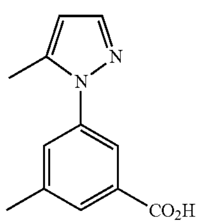 [SMILES: Cc1cc(C(=O)O)cc(-n2nccc2C)c1] | | Colourless solid (42% yield). ¹H NMR (400 MHz, DMSO) δ 8.43 (d, J = 2.4 Hz, 1H), 8.12 (s, 1H), 7.87 (s, 1H), 7.63 (s, 1H), 6.34 (d, J = 2.4 Hz, 1H), 2.42 (s, 3H), 2.27 (s, 3H). LCMS B rt 3.51 min, m/z 217.1 [M + H]⁺. |
| P34 | 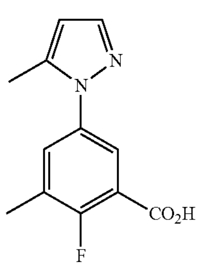 [SMILES: Cc1cc(-n2nccc2C)cc(C(=O)O)c1F] | | Colourless solid (39% yield). ¹H NMR (400 MHz, DMSO) δ 8.39 (d, J = 2.3 Hz, 1H), 8.02 (dd, J = 5.6, 2.9 Hz, 1H), 7.95 (dd, J = 5.5, 2.7 Hz, 1H), 6.34 (d, J = 2.3 Hz, 1H), 2.52-2.47 (m, 2H), 2.33 (d, J = 1.8 Hz, 3H), 2.26 (s, 3H). LCMS B rt 3.51 min, m/z 235.1 [M + H]⁺. |
| P35 | 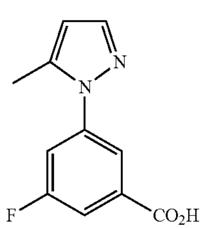 [SMILES: Cc1ccnn1-c1cc(F)cc(C(=O)O)c1] | | Off-white solid (45% yield). ¹H NMR (400 MHz, DMSO) δ 8.53 (d, J = 2.5 Hz, 1H), 8.21 (s, 1H), 7.95 (d, J = 10.2 Hz, 1H), 7.52 (d, J = 7.4 Hz, 1H), 6.39 (d, J = 2.4 Hz, 1H), 2.28 (s, 3H). LCMS B rt 3.52 min, m/z 221.1 [M + H]⁺. |

(x) 3,5-Dimethyl-1H-Pyrazole Acids

The following compound was made by the Ullmann coupling method B:

| | Structure | Starting material | Product details |
|---|---|---|---|
| P36 | 3,5-dimethyl-1H-pyrazol-1-yl phenyl CO₂H structure | Br-phenyl-COOH | Colourless solid (39% yield). $^1$H NMR (400 MHz, DMSO) δ 8.00 (t, J = 1.8 Hz, 1H), 7.94-7.90 (m, 1H), 7.76 (ddd, J = 8.0, 2.2, 1.1 Hz, 1H), 7.61 (t, J = 7.9 Hz, 1H), 6.10 (s, 1H), 2.33 (d, J = 0.4 Hz, 3H), 2.19 (s, 3H). $^{13}$C NMR (101 MHz, DMSO) δ 167.11, 148.83, 140.30, 139.82, 132.30, 129.95, 128.11, 127.88, 124.75, 108.13, 40.60, 40.39, 40.18, 39.97, 39.76, 39.56, 39.35, 13.75, 12.72. LCMS B rt 3.41 min, m/z 217.1 [M + H]⁺. |

(y) 2H-Triazole Acids

The following compounds were made by the Ullmann coupling method B:

| | Structure | Starting material | Product details |
|---|---|---|---|
| P37 | 2H-triazole-phenyl-CO₂H with methyl | Br-methyl-benzoic acid | Colourless solid (32% yield). $^1$H NMR (400 MHz, DMSO) δ 8.33 (br s, 1H), 8.13 (br s, 2H), 8.05 (s, 1H), 7.77 (s, 1H), 2.45 (s, 3H). LCMS B rt 3.49 min, m/z 204.2 [M + H]⁺. |
| P38 | 2H-triazole-phenyl-CO₂H with F | Br-F-benzoic acid | Faint yellow solid (46% yield). $^1$H NMR (400 MHz, DMSO) δ 8.38-8.35 (m, 1H), 8.20 (s, 2H), 8.05 (dt, J = 9.4, 2.3 Hz, 1H), 7.69 (ddd, J = 8.8, 2.5, 1.3 Hz, 1H). LCMS B rt 3.51 min, m/z 208.2 [M + H]⁺. |
| P39 | 2H-triazole-phenyl-CO₂H with methyl, F | Br-methyl-F-benzoic acid | Colourless solid (35% yield). $^1$H NMR (400 MHz, DMSO) δ 8.25 (dd, J = 5.8, 2.8 Hz, 1H), 8.18-8.13 (m, 3H), 2.36 (d, J = 2.3 Hz, 3H). LCMS B rt .348 min, m/z 222.1 [M + H]⁺. |

(z) Ether Acids

The following compounds were made by the Alkylation of Aryl Hydroxyl method:

| | Structure | Starting material | Product details |
|---|---|---|---|
| E1 | 3-(cyclopropylmethoxy)benzoic acid | 3-hydroxybenzoic acid (OH, CO₂H) | Off white solid (88% yield). $^1$H NMR (400 MHz, DMSO) δ 7.53-7.49 (m, 1H), 7.42-7.32 (m, 2H), 7.17 (ddd, J = 8.2, 2.7, 1.0 Hz, 1H), 3.85 (d, J = 7.0 Hz, 2H), 1.22 (dddd, J = 7.9, 5.7, 4.8, 0.8 Hz, 1H), 0.63-0.51 (m, 2H), 0.38-0.29 (m, 2H). LCMS B rt 3.57 min, m/z 191.1 [M − H]$^-$. |
| E2 | 3-(allyloxy)benzoic acid | 3-hydroxybenzoic acid | Off white solid (75% yield). $^1$H NMR (400 MHz, DMSO) δ 7.53 (d, J = 7.7 Hz, 1H), 7.45 (dd, J = 2.4, 1.5 Hz, 1H), 7.41 (t, J = 7.9 Hz, 1H), 7.22-7.18 (m, 1H), 6.04 (ddt, J = 17.2, 10.4, 5.1 Hz, 1H), 5.40 (ddd, J = 17.3, 3.3, 1.6 Hz, 1H), 5.27 (dd, J= 10.6, 1.5 Hz, 1H), 4.62 (dt, J = 5.1, 1.4 Hz, 2H). LCMS B rt 3.41 min, m/z 177.1 [M − H]$^-$. |
| E3 | 3-(cyclopropylmethoxy)-5-methylbenzoic acid | A2 | Dark beige solid (78% yield). $^1$H NMR (400 MHz, DMSO) δ 7.21 (s, 1H), 7.16 (s, 1H), 6.81 (s, 1H), 3.82 (d, J = 6.7 Hz, 2H), 2.27 (s, 3H), 1.20 (s, 1H), 0.56 (d, J = 7.0 Hz, 2H), 0.32 (d, J = 3.7 Hz, 2H). LCMS B rt 3.63 min, m/z 205.1 [M − H]$^-$. |
| E4 | 3-ethoxy-5-fluorobenzoic acid | A5 | White solid (84% yield). $^1$H NMR (400 MHz, DMSO) δ 7.26 (dd, J = 2.2, 1.3 Hz, 1H), 7.22 (ddd, J = 9.0, 2.4, 1.3 Hz, 1H), 7.07 (dt, J = 10.8, 2.4 Hz, 1H), 4.08 (q, J = 7.0 Hz, 2H), 1.32 (t, J = 7.0 Hz, 3H). LCMS B rt 3.55 min, m/z 183.1 [M − H]$^-$. |
| E5 | 3-fluoro-5-isopropoxybenzoic acid | A5 | Off white solid (82% yield). $^1$H NMR (400 MHz, DMSO) δ 7.24 (d, J = 1.2 Hz, 1H), 7.22-7.17 (m, 1H), 7.08 (dt, J = 10.9, 2.3 Hz, 1H), 4.69 (dt, J = 12.0, 6.0 Hz, 1H), 1.27 (d, J = 6.0 Hz, 6H). LCMS B rt 3.62 min, m/z 197.1 [M − H]$^-$. |
| E6 | 3-(cyclopropylmethoxy)-5-fluorobenzoic acid | A5 | Dark beige solid (86% yield). $^1$H NMR (400 MHz, DMSO) δ 7.13 (dd, J = 2.2, 1.3 Hz, 1H), 7.08 (ddd, J = 8.9, 2.4, 1.3 Hz, 1H), 6.95 (dt, J = 10.8, 2.4 Hz, 1H), 3.74 (d, J = 7.0 Hz, 2H), 1.16-1.01 (m, 1H), 0.52-0.39 (m, 2H), 0.22-0.14 (m, 2H). LCMS B rt 3.63 min, m/z 209.1 [M − H]$^-$. |

| Structure | Starting material | Product details |
|---|---|---|
| E7 | A5 | Off white solid (86% yield). $^1$H NMR (400 MHz, DMSO) δ 7.30 (dd, J = 2.1, 1.3 Hz, 1H), 7.24 (ddd, J = 8.9, 2.3, 1.3 Hz, 1H), 7.13 (dt, J = 10.8, 2.4 Hz, 1H), 6.03 (ddt, J = 17.3, 10.5, 5.2 Hz, 1H), 5.41 (dq, J = 17.3, 1.7 Hz, 1H), 5.28 (ddd, J = 10.6, 3.0, 1.4 Hz, 1H), 4.65 (dt, J = 5.2, 1.5 Hz, 2H). LCMS B rt 3.43 min, m/z 195.1 [M − H]$^-$. |
| E8 | A3 | Off white solid (82% yield). $^1$H NMR (400 MHz, DMSO) δ 7.16-7.08 (m, 2H), 6.02 (ddt, J = 17.3, 10.4, 5.1 Hz, 1H), 5.38 (dq, J = 17.3, 1.7 Hz, 1H), 5.25 (ddd, J = 10.5, 3.1, 1.5 Hz, 1H), 4.56 (dt, J = 5.1, 1.5 Hz, 2H), 2.23 (d, J = 2.3 Hz, 3H). LCMS B rt 3.58 min, m/z 211.2 [M + H]$^+$. |
| E9 | A3 | Off white solid (80% yield). $^1$H NMR (400 MHz, DMSO) δ 7.09 (d, J = 5.5 Hz, 2H), 3.80 (d, J = 7.0 Hz, 2H), 2.22 (d, J = 2.3 Hz, 3H), 1.26-1.11 (m, 1H), 0.58-0.52 (m, 2H), 0.35-0.27 (m, 2H). LCMS B rt 3.42 min, m/z 223.1 [M − H]$^-$. |

(aa) 2-Fluoro-5-(furan-2-yl)-3-methylbenzoic acid (I15)

(i) 3-(Furan-2-yl)-5-methylbenzoic acid (I14)

To a degassed solution of 9:1 1,4-dioxane:H$_2$O (4 mL) was added 3-bromo-5-methylbenzoic acid (0.300 g, 1.395 mmol), 2-furanboronic acid (0.187 g, 1.674 mmol), K$_2$CO$_3$ (0.289 g, 2.093 mmol) and PdCl$_2$(PPh$_3$)$_2$ (0.049 g, 0.070 mmol), under an atmosphere of nitrogen. The reaction was irradiated in a CEM microwave reactor at 80° C. for 30 min, then cooled and passed through a pad of Celite. The Celite was washed with a portion of EtOAc (10 mL) and the entire mixture was concentrated to dryness. The residue was taken up in DCM (20 mL) and an aq. soln. of 2 M HCl (20 mL) was added. The two layers were separated, and the aqueous layer was further extracted with DCM (2×20 mL). The organics were combined, washed with brine, dried (Na$_2$SO$_4$) and concentrated in vacuo. The crude material was purified by silica gel chromatography (Isolera Biotage, 24 g Si Cartridge, 0-40% EtOAc in petroleum benzine 40-60° C.) with the fractions containing suspected product collected and concentrated in vacuo to yield 3-(furan-2-yl)-5-methyl-benzoic acid (I14)(0.095 g, 34% yield) as a white solid. $^1$H NMR (400 MHz, CDCl$_3$): δ 8.24-8.20 (m, 1H), 7.85-7.81 (m, 1H), 7.77-7.71 (m, 1H), 7.50 (dd, J=1.8, 0.8 Hz, 1H), 6.74 (dd, J=3.4, 0.7 Hz, 1H), 6.50 (dd, J=3.3, 1.8 Hz, 1H), 2.46 (s, 3H).

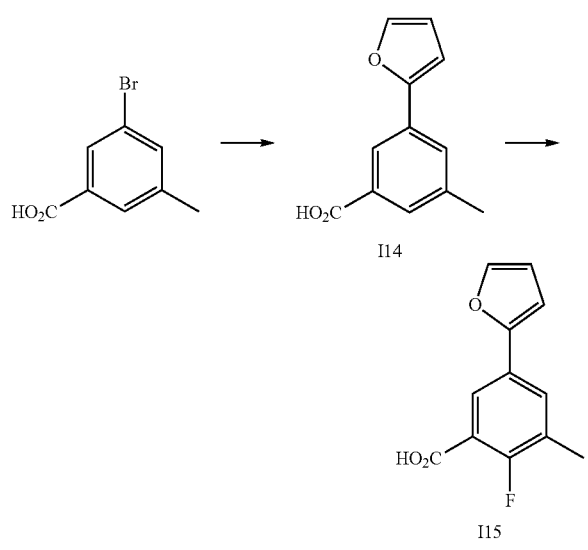

(ii) 2-Fluoro-5-(furan-2-yl)-3-methylbenzoic acid (I15)

To a degassed solution of 9:1 1,4-dioxane:H$_2$O (4 mL) was added 5-bromo-2-fluoro-3-methylbenzoic acid (I14) (0.200 g, 0.858 mmol), 2-furanboronic acid (0.106 g, 0.944 mmol), K$_2$CO$_3$ (0.178 g, 1.287 mmol) and PdCl$_2$(PPh$_3$)$_2$ (0.030 g, 0.043 mmol), under an atmosphere of nitrogen. The reaction was irradiated in a CEM microwave reactor at 80° C. for 30 min, then cooled and passed through a pad of Celite. The Celite was washed with EtOAc (20 mL). The mixture was acidified using 2 M HCl (1 mL) and concentrated in vacuo. The crude material was purified by silica gel chromatography (Isolera Biotage, 24 g Si Cartridge, 0-60% EtOAc in petroleum benzine 40-60° C.). Fractions containing the suspected product were concentrated in vacuo to give 2-fluoro-5-(furan-2-yl)-3-methylbenzoic acid (I15) (0.050 g, 26% yield) as a white solid. LCMS B rt. 3.63 min, m/z 221.1 [M+H]$^+$.

(bb) 2,4-Difluoro-5-methyl-[1,1'-biphenyl]-3-carboxylic acid (I17)

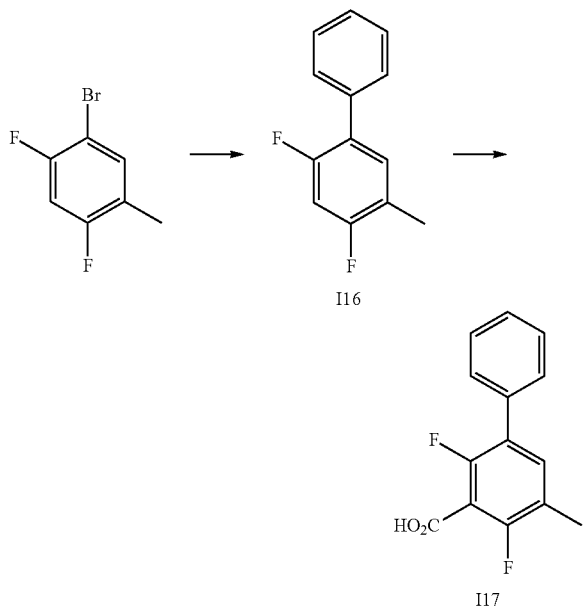

(i) 2,4-Difluoro-5-methyl-1,1'-biphenyl (I16)

The desired compound was prepared from 1-bromo-2,4-difluoro-5-methylbenzene by general procedure "Suzuki Coupling F" to obtain a colourless oil (79% yield). $^1$H NMR (400 MHz, CDCl$_3$) δ 7.55-7.35 (m, 5H), 7.29-7.22 (m, 1H), 6.88 (t, J=9.9 Hz, 1H), 2.35-2.26 (m, 3H).

(ii) 2,4-Difluoro-5-methyl-[1,1'-biphenyl]-3-carboxylic acid (I17)

The desired compound was prepared from compound I16 by general procedure "Carboxylation" to obtain a colourless solid (78% yield). $^1$H NMR (400 MHz, CDCl$_3$) δ 7.58-7.37 (m, 6H), 2.41-2.26 (m, 3H).

(cc) 2,6-Difluoro-3-methyl-5-(1H-pyrazol-1-yl)benzoic acid (I19)

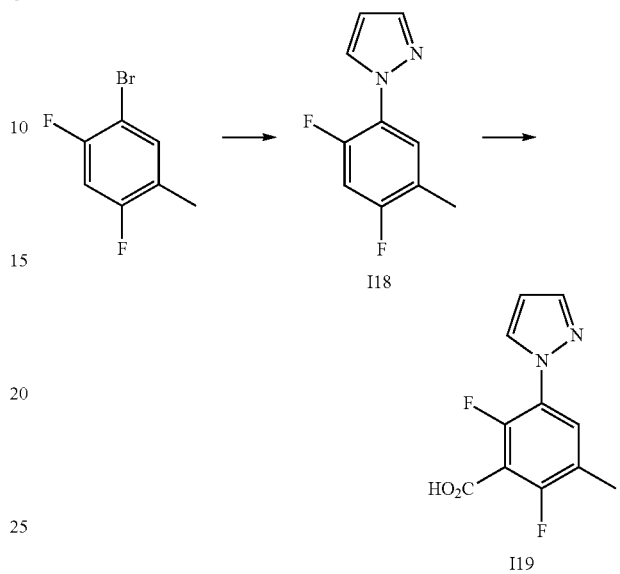

(i) 1-(2,4-Difluoro-5-methylphenyl)-1H-pyrazole (I18)

The desired compound was prepared from 1-bromo-2,4-difluoro-5-methylbenzene by general procedure "Ullmann Coupling Method B" to obtain a colourless oil (33% yield). $^1$H NMR (400 MHz, CDCl$_3$) 7.94-7.90 (m, 1H), 7.75-7.67 (m, 2H), 6.93 (dd, J=11.2, 9.0 Hz, 1H), 6.47 (dd, J=2.4, 1.9 Hz, 1H), 2.35-2.17 (m, 3H). LCMS B rt 3.61 min, m/z 195.0 [M+H]$^+$.

(ii) 2,6-Difluoro-3-methyl-5-(1H-pyrazol-1-yl)benzoic acid (I19)

The desired compound was prepared from compound I18 by general procedure "Carboxylation" to obtain a colourless solid (66% yield). $^1$H NMR (400 MHz, CDCl$_3$) δ 7.99 (s, 1H), 7.93 (t, J=7.9 Hz, 1H), 7.79 (s, 1H), 6.54 (s, 1H), 2.36 (d, J=1.7 Hz, 3H). LCMS B rt 3.66 min, m/z 239.1 [M+H]$^+$.

(dd) 3-Ethoxy-2,6-difluoro-5-methylbenzoic acid (I23)

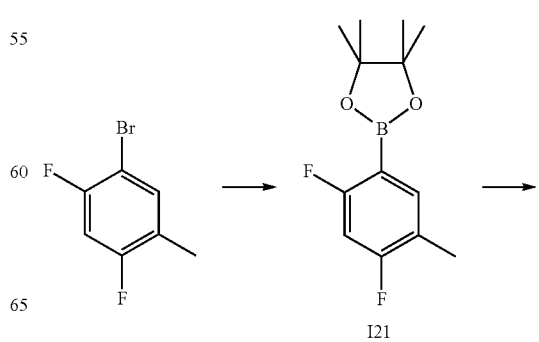

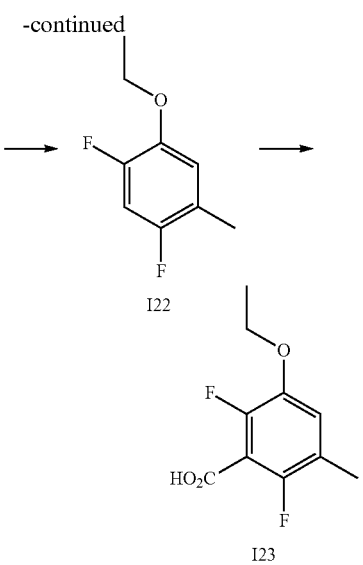

(i) 2-(2,4-Difluoro-5-methylphenyl)-4,4,5,5-tetramethyl-1,3,2-dioxaborolane (I20)

The desired compound was prepared from 1-bromo-2,4-difluoro-5-methylbenzene by general procedure "Suzuki Coupling Method E" to obtain a dark brown solid (81% yield) $^1$H NMR (400 MHz, CDCl$_3$) δ 7.48 (dd, J=9.1, 7.1 Hz, 1H), 6.65 (t, J=9.6 Hz, 1H), 2.17-2.14 (m, 3H), 1.28 (d, J=2.5 Hz, 12H).

(ii) 2,4-Difluoro-5-methylphenol (I21)

To a solution of 2-(2,4-difluoro-5-methyl-phenyl)-4,4,5,5-tetramethyl-1,3,2-dioxaborolane (I20) (1.0 g, 3.94 mmol, 1.0 eq) in a mixture of NaOH (1 M aqueous solution, 11.8 mL, 11.8 mmol, 3.0 eq) and THF (10 mL) at 0° C. was added H$_2$O$_2$ (1.34 g, 11.8 mmol, 3 eq). The reaction mixture was stirred at room temperature for 1 h, then the pH of the reaction mixture was adjusted to pH 5 by addition of 1 M HCl. The aqueous layer was extracted with EtOAc and the combined organic extracts were washed with water and brine, dried (Mg$_2$SO$_4$), filtered and evaporated in vacuo. The crude residue obtained was purified by column chromatography (petroleum ether: EtOAc, 100:1 to 50:1) to give the title compound as a colorless oil, yield (0.38 g, 67% yield). $^1$H NMR (400 MHz, CDCl$_3$) δ 6.72 (ddd, J=10.3, 8.3, 5.2 Hz, 2H), 5.03 (s, 1H), 2.12 (d, J=0.9 Hz, 3H).

(iii) 1-Ethoxy-2,4-difluoro-5-methylbenzene (I22)

The desired compound was prepared from 2,4-difluoro-5-methylphenol (I21) by general procedure "Alkylation of Aryl Hydroxyl Method" to obtain a yellow liquid (55% yield).
$^1$H NMR (400 MHz, CDCl$_3$) δ 6.77 (ddd, J=12.6, 9.9, 8.5 Hz, 2H), 4.05 (q, J=7.0 Hz, 2H), 2.24-2.19 (m, 3H), 1.42 (t, J=7.0 Hz, 3H).

(iv) 3-Ethoxy-2,6-difluoro-5-methylbenzoic acid (I23)

The desired compound was prepared from 1-ethoxy-2,4-difluoro-5-methylbenzene (I22) by general procedure "Carboxylation" to give a colourless solid (78% yield). $^1$H NMR (400 MHz, CDCl$_3$) δ 6.96 (dd, J=8.4, 7.5 Hz, 1H), 4.11 (q, J=7.0 Hz, 2H), 2.34-2.21 (m, 3H), 1.45 (t, J=7.0 Hz, 3H).

(ee) 4-Fluoro-[1,1'-biphenyl]-3-carboxylic acid (I24)

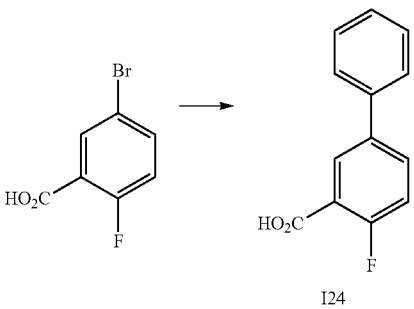

4-Fluoro-[1,1'-biphenyl]-3-carboxylic acid was made as per general "Suzuki Coupling F", from 5-bromo-2-fluorobenzoic acid (1 g, 4.57 mmol) and phenylboronic acid (0.724 g, 5.94 mmol). However after the reaction mixture was cooled down it was passed through a bed of celite, evaporated in-vacuo, acidified with 1 M HCl and the resulting white precipitate was filtered off and dried in an oven at 130° C. (0.988 g, 100%). $^1$H NMR (400 MHz, DMSO) δ 13.38 (s, 1H), 8.08 (dd, J=7.0, 2.5 Hz, 1H), 7.93 (ddd, J=8.5, 4.5, 2.6 Hz, 1H), 7.77-7.61 (m, 2H), 7.49 (dd, J=10.3, 4.8 Hz, 2H), 7.41 (ddd, J=7.8, 7.3, 5.9 Hz, 2H).

Example 1

The following compounds were synthesised according to the Amide Coupling method B from commercially available starting materials:

| | Structure | Product details |
|---|---|---|
| 1 | 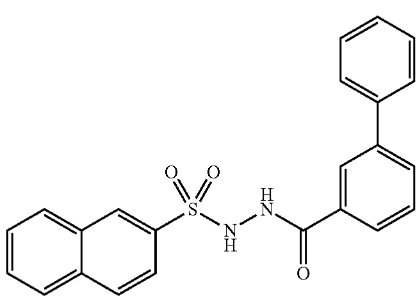 [SMILES: O=C(NNS(=O)(=O)c1ccc2ccccc2c1)c1cccc(-c2ccccc2)c1] | Yellow solid (54% yield). $^1$H NMR (Acetone-d6) δ 8.55 (s, 1H), 7.98-7.95 (m, 5H), 7.82-7.79 (m, 1H), 7.70-7.58 (m, 5H, H), 7.51-7.35 (m, 4H). LCMS C rt 7.73 min, m/z 403.2 [M + H]$^+$. |

| | Structure | Product details |
|---|---|---|
| 2 | 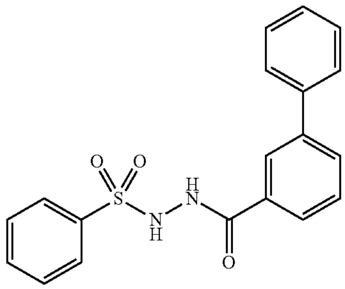 [SMILES: O=C(NNS(=O)(=O)c1ccccc1)c1cccc(-c2ccccc2)c1] | White solid (13% yield). $^1$H NMR (DMSO) δ 10.78 (s, 1H), 10.01 (s, 1H), 7.96 (s, 1H), 7.85-7.81 (m, 3H), 7.71-7.68 (m, 2H), 7.64-7.59 (m, 2H), 7.54-7.51 (m, 5H), 7.39-7.46 (m, 1H). LCMS C rt 7.03 min, m/z 353.1 [M + H]$^+$. |
| 3 | 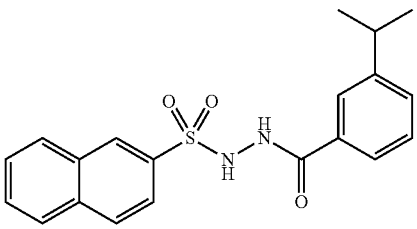 [SMILES: CC(C)c1cccc(C(=O)NNS(=O)(=O)c2ccc3ccccc3c2)c1] | White solid (8% yield). $^1$H NMR (Acetone-d6) δ 10.03 (s, 1H), 8.52 (s, 1H), 8.08-7.94 (m, 4H), 7.67-7.59 (m, 3H), 7.52-7.49 (m, 1H), 7.41-7.38 (m, 1H), 7.32-7.29 (m, 1H), 2.88 (sept, 1H J = 6.93 Hz), 1.18 (d, 6H, J = 6.93 Hz). LCMS C rt 7.53 min, m/z 369.1 [M + H]$^+$. |
| 4 | 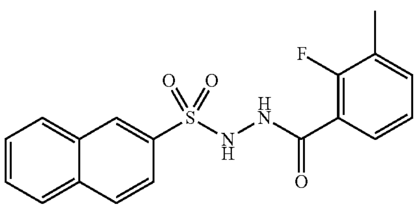 [SMILES: Cc1cccc(C(=O)NNS(=O)(=O)c2ccc3ccccc3c2)c1F] | White solid (23% yield) as a white solid; $^1$H NMR (DMSO): δ 10.53 (s, 1H), 10.17 (s, 1H), 8.49 (s, 1H), 8.15-8.00 (m, 3H), 7.89-7.86 (m, 1H), 7.71-7.63 (m, 2H), 7.37-7.35 (m, 1H), 7.15-7.08 (m, 2H), 2.19 (s, 3H), LCMS C rt 6.92 min, m/z 359.1 [M + H]. |
| 5 | 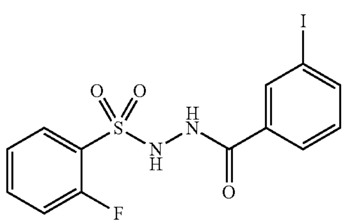 [SMILES: O=C(NNS(=O)(=O)c1ccccc1F)c1cccc(I)c1] | Faint yellow solid (64% yield). $^1$H NMR (400 MHz, DMSO) δ 10.8 (s, 1H), 10.3 (s, 1H), 8.0 (s, 1H), 7.90 (d, 1H), 7.80 (t, 1H), 7.70 (d, 2H), 7.40 (t, 1H), 7.32-7.20 (m, 2H). |
| 6 | 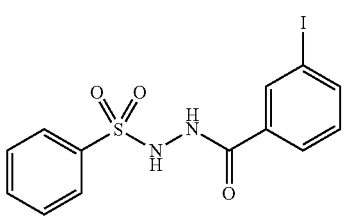 [SMILES: O=C(NNS(=O)(=O)c1ccccc1)c1cccc(I)c1] | Colourless solid (66% yield). $^1$H NMR (400 MHz, DMSO-d$_6$) δ 10.75 (s, 1H), 10.0 (s, 1H), 8.0 (s, 1H), 7.9 (d, 1H), 7.82 (d, 2H), 7.7-7.6 (m, 2H), 7.52 (t, 2H), 7.25 (t, 1H). |
| 7 | 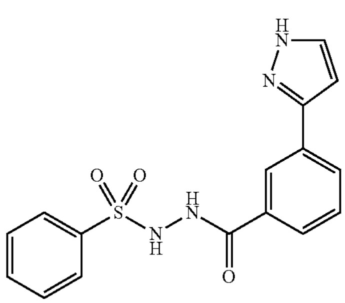 [SMILES: O=C(NNS(=O)(=O)c1ccccc1)c1cccc(-c2cc[nH]n2)c1] | Colourless sticky solid (15.9 mg, 18% yield). $^1$H NMR (400 MHz, DMSO) δ 12.98 (s, 1H), 10.76 (s, 1H), 10.04 (d, J = 2.4 Hz, 1H), 8.13 (s, 1H), 7.96 (d, J = 8.3 Hz, 1H), 7.86-7.79 (m, 3H), 7.65-7.47 (m, 5H), 6.74 (d, J = 2.0 Hz, 1H). LCMS A rt 5.39 min, m/z 343.1 [M + H]$^+$. |

-continued

| | Structure | Product details |
|---|---|---|
| 8 | 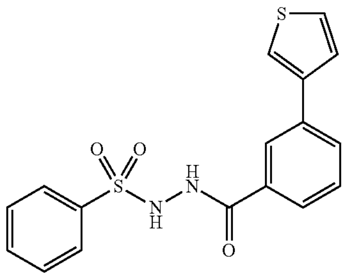 [SMILES: O=C(NNS(=O)(=O)c1ccccc1)c1cccc(-c2ccsc2)c1] | Colourless solid (13.1 mg, 7% yield). $^1$H NMR (400 MHz, DMSO) δ 10.74 (s, 1H), 10.05 (s, 1H), 8.02 (s, 1H), 7.93 (dd, J = 2.9, 1.3 Hz, 1H), 7.88-7.84 (m, 3H), 7.68 (dd, J = 5.0, 2.9 Hz, 1H), 7.66-7.42 (m, 6H). LCMS A rt 6.21 min, m/z 359.1 [M + H]$^+$. |
| 9 | 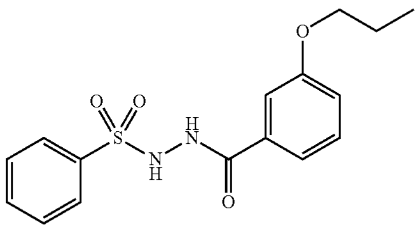 [SMILES: CCCOc1cccc(C(=O)NNS(=O)(=O)c2ccccc2)c1] | Colourless solid (30.7 mg, 13% yield). $^1$H NMR (400 MHz, DMSO) δ 10.66 (s, 1H), 10.02 (s, 1H), 7.83 (d, J = 7.4 Hz, 2H), 7.63 (t, J = 7.4 Hz, 1H), 7.53 (t, J = 7.6 Hz, 2H), 7.33 (t, J = 7.9 Hz, 1H), 7.28-7.15 (m, 2H), 7.09 (dd, J= 8.1, 1.8 Hz, 1H), 3.93 (t, J = 6.5 Hz, 2H), 1.85-1.60 (sex. J = 7.1 Hz, 2H), 0.97 (t, J = 7.4 Hz, 3H). LCMS A rt 6.21, m/z 335.1 [M + H]$^+$. |
| 10 | 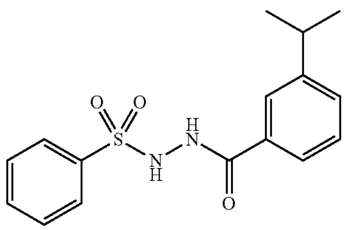 [SMILES: CC(C)c1cccc(C(=O)NNS(=O)(=O)c2ccccc2)c1] | HOBt was used instead of HOAt<br>Colourless solid (0.254 g, 91% yield). $^1$H NMR (400 MHz, DMSO) δ 10.64 (s, 1H), 9.98 (s, 1H), 7.93-7.71 (m, 2H), 7.70-7.58 (m, 1H), 7.55-7.51 (m, 3H), 7.48 (d, J = 7.6 Hz, 1H), 7.41 (d, J = 7.8 Hz, 1H), 7.34 (t, J = 7.6 Hz, 1H), 2.90 (hept, J = 6.8 Hz, 1H), 1.19 (d, J = 6.9 Hz, 6H). LCMS A rt 6.27, m/z 319.1 [M + H]$^+$. |
| 11 | 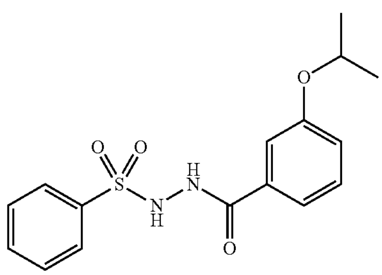 [SMILES: CC(C)Oc1cccc(C(=O)NNS(=O)(=O)c2ccccc2)c1] | Colourless solid (70 mg, 15% yield). $^1$H NMR (400 MHz, DMSO) δ 10.61 (br s, 1H), 9.99 (br s, 1H), 7.83 (d, J = 7.5 Hz, 2H), 7.63 (t, J = 7.4 Hz, 1H), 7.53 (t, J = 7.6 Hz, 2H), 7.32 (t, J = 7.9 Hz, 1H), 7.25-7.12 (m, 2H), 7.07 (dd, J = 8.1, 2.0 Hz, 1H), 4.62 (sept., 6.0 Hz, 1H), 1.26 (d, J = 6.0 Hz, 6H). LCMS A rt 6.12, m/z 335.1 [M + H]$^+$. |
| 12 | 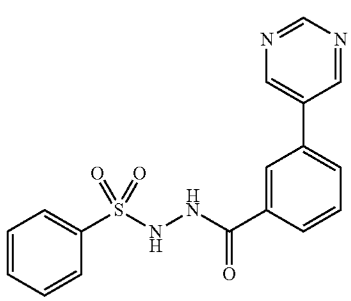 [SMILES: O=C(NNS(=O)(=O)c1ccccc1)c1cccc(-c2cncnc2)c1] | Colourless solid (9.5 mg, 10% yield). $^1$H NMR (400 MHz, DMSO) δ 13.84 (s, 1H), 10.83 (d, J = 3.4 Hz, 1H), 10.14 (d, J = 3.4 Hz, 1H), 9.19 (s, 2H), 8.12 (s, 1H), 8.00 (d, J = 7.8 Hz, 1H), 7.86 (d, J = 7.3 Hz, 2H), 7.74 (d, J = 7.8 Hz, 1H), 7.63 (q, J = 7.3 Hz, 2H), 7.58-7.43 (m, 2H). LCMS A rt 5.32 min, m/z 355.1 [M + H]$^+$. |
| 13 | 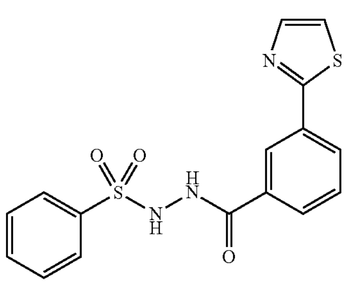 [SMILES: O=C(NNS(=O)(=O)c1ccccc1)c1cccc(-c2nccs2)c1] | Colourless solid (42.7 mg, 34% yield). $^1$H NMR (400 MHz, DMSO) δ 10.93 (s, 1H), 10.13 (s, 1H), 8.24 (s, 1H), 8.11 (dd, J = 5.3, 4.0 Hz, 1H), 7.97 (d, J = 3.2 Hz, 1H), 7.91-7.81 (m, 3H), 7.77 (d, J= 7.9 Hz, 1H), 7.69-7.41 (m, 4H). LCMS A rt 5.80 min, m/z 360.1 [M + H]$^+$. |

|   | Structure | Product details |
|---|---|---|
| 14 | 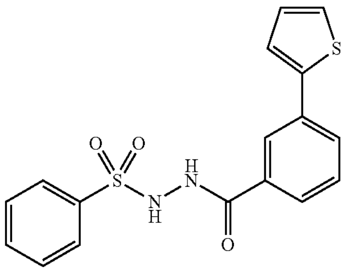 [SMILES: O=C(NNS(=O)(=O)c1ccccc1)c1cccc(-c2cccs2)c1] | HOBt was used instead of HOAt<br>Colourless solid (87 mg, 40% yield). ¹H NMR (400 MHz, DMSO) δ 10.83 (d, J = 3.3 Hz, 1H), 10.09 (d, J = 3.3 Hz, 1H), 7.93 (s, 1H), 7.86-7.82 (m, 3H), 7.71-7.43 (m, 7H), 7.17 (dd, J = 5.1, 3.6 Hz, 1H). LCMS A rt 6.27, m/z 359.1 [M + H]⁺. |
| 15 | 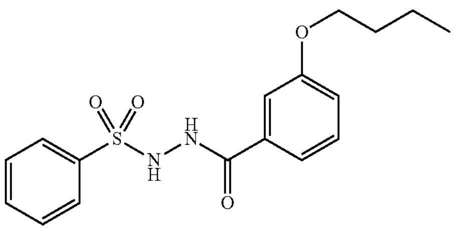 [SMILES: CCCCOc1cccc(C(=O)NNS(=O)(=O)c2ccccc2)c1] | Colourless solid (70 mg, 39% yield). ¹H NMR (400 MHz, DMSO) δ 10.66 (br s, 1H), 10.01 (br s, 1H), 7.89-7.73 (m, 2H), 7.69-7.58 (m, 1H), 7.55-7.51 (m, 2H), 7.33 (t, J = 7.9 Hz, 1H), 7.24-7.20 (m, 2H), 7.08 (dd, J = 8.1, 1.8 Hz, 1H), 3.97 (t, J = 6.5 Hz, 2H), 1.75-1.62 (pent. J = 6.6 Hz, 2H), 1.51-1.33 (sex., J = 7.5 Hz, 2H), 0.93 (t, J = 7.4 Hz, 3H). LCMS A rt 6.46 min, m/z 349.1 [M + H]⁺. |
| 16 | 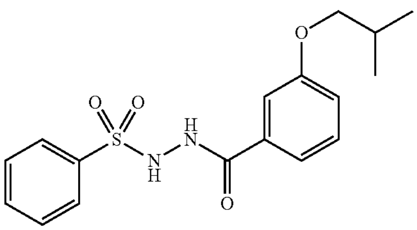 [SMILES: CC(C)COc1cccc(C(=O)NNS(=O)(=O)c2ccccc2)c1] | Colourless solid (52 mg, 29% yield). ¹H NMR (400 MHz, DMSO) δ 10.66 (br s, 1H), 10.03 (br s, 1H), 7.93-7.75 (m, 2H), 7.68-7.58 (m, 1H), 7.55-7.51 (m, 2H), 7.33 (t, J = 7.9 Hz, 1H), 7.24-7.21 (m, 2H), 7.09 (ddd, J = 8.2, 2.5, 0.8 Hz, 1H), 3.75 (d, J = 6.5 Hz, 2H), 2.05-1.94 (m, 1H), 0.98 (d, J = 6.7 Hz, 6H). LCMS A rt 6.15 min, m/z 349.1 [M + H]⁺. |
| 17 | 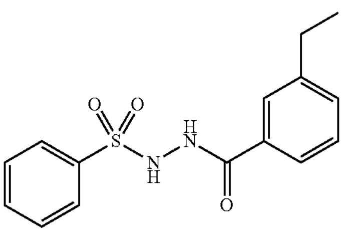 [SMILES: CCc1cccc(C(=O)NNS(=O)(=O)c2ccccc2)c1] | HOBt was used instead of HOAt<br>Colourless solid (45 mg, 25% yeld). ¹H NMR (400 MHz, DMSO) δ 10.64 (br s. 1H), 10.01 (br s, 1H), 7.88-7.79 (m, 2H), 7.62 (ddd, J= 8.7, 2.4, 1.2 Hz, 1H), 7.55-7.47 (m, 4H), 7.39-7.33 (m, 2H), 2.62 (q, J = 7.6 Hz, 2H), 1.17 (t, J = 7.6 Hz, 3H). LCMS A rt 6.15 min, m/z 305.1 [M + H]⁺. |
| 18 | 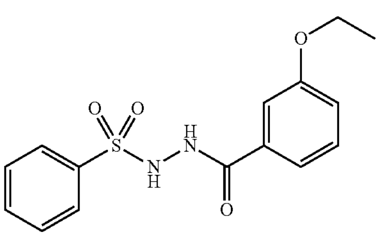 [SMILES: CCOc1cccc(C(=O)NNS(=O)(=O)c2ccccc2)c1] | Colourless solid (57 mg, 16% yield). ¹H NMR (400 MHz, DMSO) δ 10.65 (s, 1H), 10.01 (s, 1H), 7.91-7.72 (m, 2H), 7.70-7.58 (m, 1H), 7.58-7.43 (m, 2H), 7.33 (t, J = 7.9 Hz, 1H), 7.21 (dd, J = 15.2, 5.0 Hz, 2H), 7.08 (ddd, J = 8.2, 2.5, 0.7 Hz, 1H), 4.03 (q, J = 7.0 Hz, 2H), 1.32 (t, J = 7.0 Hz, 3H). LCMS A rt 6.00 min m/z 321.1 [M + H]⁺. |
| 19 | 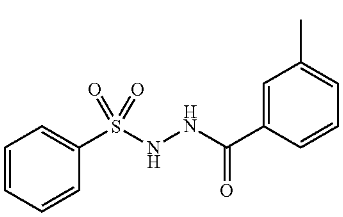 [SMILES: Cc1cccc(C(=O)NNS(=O)(=O)c2ccccc2)c1] | Colourless solid (153 mg, 36% yield). ¹H NMR (400 MHz, DMSO) δ 10.63 (d, J = 2.6 Hz, 1H), 10.01 (d, J = 3.0 Hz, 1H), 7.91-7.75 (m, 2H), 7.68-7.57 (m, 1H), 7.57-7.42 (m, 4H), 7.42-7.23 (m, 2H), 2.32 (s, 3H). LCMS A rt 5.94 min, m/z 291.1 [M + H]⁺. |

| | Structure | Product details |
|---|---|---|
| 20 | (2-fluorophenyl)sulfonyl hydrazide of 3-methylbenzoic acid | Colourless solid (267 mg, 41% yield). ¹H NMR (400 MHz, DMSO) δ 10.66 (d, J = 2.5 Hz, 1H), 10.25 (d, J = 2.6 Hz, 1H), 7.78 (td, J = 7.6, 1.6 Hz, 1H), 7.74-7.59 (m, 1H), 7.50-7.47 (m, 2H), 7.43-7.20 (m, 4H), 2.31 (s, 3H). LCMS A rt 5.96 min, m/z 309.0 [M + H]⁺. |
| 21 | phenylsulfonyl hydrazide of 3-propylbenzoic acid | Colourless solid (38 mg, 37% yield). ¹H NMR (400 MHz, DMSO) δ 10.63 (s, 1H), 9.98 (s, 1H), 8.00-7.73 (m, 2H), 7.71-7.55 (m, 1H), 7.55-7.43 (m, 4H), 7.42-7.19 (m, 2H), 2.62-2.51 (t, J = 7.8 Hz, 2H), 1.67-1.48 (sex, J = 7.5 Hz, 2H), 0.88 (t, J = 7.3 Hz, 3H). LCMS A rt 6.14 min, m/z 319.0 [M + H]⁺. |
| 22 | phenylsulfonyl hydrazide of 3-(trifluoromethoxy)benzoic acid | Colourless solid (42 mg, 29% yield). ¹H NMR (400 MHz, DMSO) δ 10.86 (br s, 1H), 10.12 (br s, 1H), 7.84 (d, J = 7.4 Hz, 2H), 7.73 (d, J = 7.3 Hz, 1H), 7.67-7.50 (m, 6H). LCMS A rt 6.22 min, m/z 361.1 [M + H]⁺. |
| 23 | phenylsulfonyl hydrazide of 3-(cyclopentyloxy)benzoic acid | Colourless solid (41 mg, 36% yield). ¹H NMR (400 MHz, DMSO) δ 10.63 (s, 1H), 9.98 (s, 1H), 8.00-7.73 (m, 2H), 7.72-7.57 (m, 1H), 7.53 (t, J = 7.6 Hz, 2H), 7.32 (t, J = 7.9 Hz, 1H), 7.21 (d, J = 7.7 Hz, 1H), 7.16 (s, 1H), 7.06 (dd, J = 8.1, 1.8 Hz, 1H), 4.85-4.81 (m, 1H), 1.98-1.77 (m, 2H), 1.70-1.65 (m, 4H), 1.61-1.58 (m, 2H). LCMS A rt 6.45 min, m/z 361.1 [M + H]⁺. |

Example 2

The following compounds were synthesised according to the Sulfonamide coupling method from commercially available starting materials:

| | Structure | Product details |
|---|---|---|
| 24 | (2-fluorophenyl)sulfonyl hydrazide of biphenyl-3-carboxylic acid | Colourless solid (59% yield). ¹HNMR (400 MHz, CDCl₃) δ 10.7 (s, 1H), 10.4 (s, 1H), 7.87-7.80 (m, 2H), 7.73 (m, 3H), 7.45-7.30 (m, 5H), 730-7.22 (m, 2H) |

-continued

| | Structure | Product details |
|---|---|---|
| 25 | 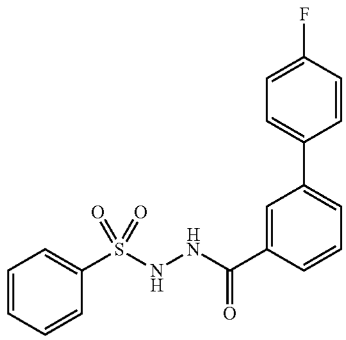 [SMILES: O=C(NNS(=O)(=O)c1ccccc1)c1cccc(-c2ccc(F)cc2)c1] | Colourless solid (61% yield). ¹H-NMR (400 MHz, CDCl₃): δ 10.8 (s, 1H), 10.08 (s, 1H), 7.90 (s, 1H), 7.80 (m, 5H), 7.60 (d, 6H), 7.35 (t, 2H). |
| 26 | 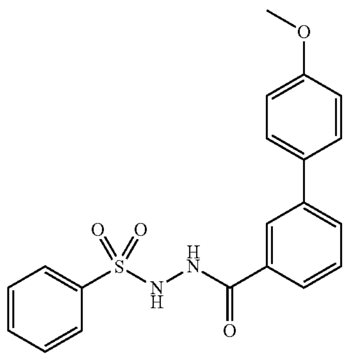 [SMILES: COc1ccc(-c2cccc(C(=O)NNS(=O)(=O)c3ccccc3)c2)cc1] | Colourless solid (56% yield). ¹H NMR (400 MHz, CDCl₃) δ 10.80 (s, 1H), 10.08 (s, 1H), 7.85 (d, 2H), 7.78 (d, 1H), 7.68-7.60 (m, 3H), 7.60-7.48 (m, 4H), 7.06 (d, 2H), 3.80 (s, 3H). |
| 27 | 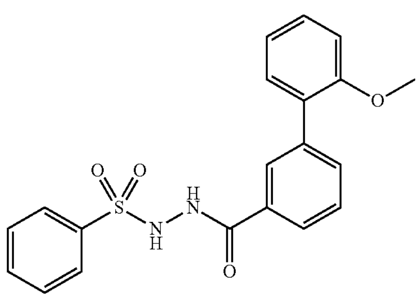 [SMILES: COc1ccccc1-c1cccc(C(=O)NNS(=O)(=O)c2ccccc2)c1] | Colourless solid (59% yield). ¹H NMR (400 MHz, CDCl₃): δ 10.8 (s, 1H), 10.08 (s, 1H), 7.78 (d, 3H), 7.60 (d, 4H), 7.51-7.27 (m, 3H), 7.10 (d, 2H), 3.77 (s, 3H). |
| 28 | 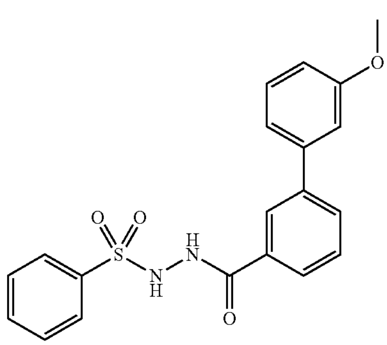 [SMILES: COc1cccc(-c2cccc(C(=O)NNS(=O)(=O)c3ccccc3)c2)c1] | Colourless solid (57% yield). ¹H NMR (400 MHz, CDCl₃): δ 10.8 (s, 1H), 10.08 (s, 1H), 7.98 (s, 1H), 7.86 (d, 4H), 7.65 (t, 4H), 7.53 (m, 4H), 7.41 (t, 1H), 7.25 (d, 2H), 7.0 (d, 1H), 3.77 (s, 3H). |

-continued

| | Structure | Product details |
|---|---|---|
| 29 | (structure: N'-(phenylsulfonyl)-2'-fluoro-[1,1'-biphenyl]-3-carbohydrazide) | Colourless solid (61% yield). $^1$H NMR (400 MHz, DMSO) δ 10.7 (s, 1H), 10.08 (s, 1H), 7.95 (s, 1H), 7.85 (d, 3H), 7.65-7.45 (m, 8H), 7.17 (t, 1H). |
| 30 | (structure: N'-(phenylsulfonyl)-3'-fluoro-[1,1'-biphenyl]-3-carbohydrazide) | Colourless solid (62% yield). $^1$H NMR (400 MHz, DMSO) δ 10.7 (s, 1H), 10.08 (s, 1H), 7.80 (d, 3H), 7.65 (t, 2H), 7.60-7.45 (m, 5H), 7.40 (m, 1H), 7.30-7.25 (m, 2H). |
| 31 | (structure: 3'-cyano-N'-(phenylsulfonyl)-[1,1'-biphenyl]-3-carbohydrazide) | Colourless solid (65% yield). $^1$H NMR (400 MHz, DMSO) δ 10.7 (s, 1H), 10.08 (s, 1H), 8.20 (s, 1H), 8.05 (d, 2H), 7.93 (d, 1H), 7.85 (t, 3H), 7.7 (m, 2H), 7.62 (t, 1H), 7.55 (m, 3H) |
| 32 | (structure: 4'-chloro-N'-(phenylsulfonyl)-[1,1'-biphenyl]-3-carbohydrazide) | Colourless solid (60% yield). $^1$H NMR (400 MHz, DMSO): δ 10.7 (s, 1H), 10.08 (s, 1H), 8.00 (s, 1H), 7.93 (d, 1H), 7.82 (d, 3H), 7.75 (d, 2H), 7.62 (m, 2H), 7.50 (m, 5H). |
| 33 | (structure: 2-fluoro-N'-(phenylsulfonyl)-[1,1'-biphenyl]-3-carbohydrazide) | Colourless solid (62% yield). $^1$H NMR (400 MHz, DMSO) δ 710.7 (s, 1H), 10.08 (s, 1H), 7.88 (d, 2H), 7.68-7.60 (m, 2H), 7.60-7.48 (m, 6H), 7.46-7.41 (m, 1H), 7.38-7.30 (m, 2H). |

-continued

| | Structure | Product details |
|---|---|---|
| 34 | 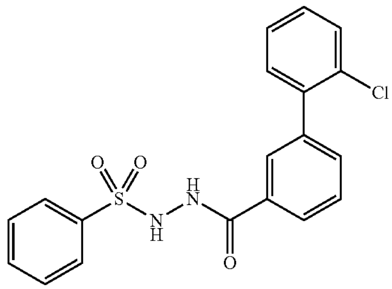 [SMILES: O=C(NNS(=O)(=O)c1ccccc1)c1cccc(-c2ccccc2Cl)c1] | Colourless solid (63% yield). ¹H NMR (400 MHz, DMSO) δ 10.75 (s, 1H), 10.05 (s, 1H), 7.84 (d, 2H), 7.72 (d, 2H), 7.65-7.50 (m, 6H), 7.45 (s, 3H). |

Example 3

The following compounds were synthesised according to the specified Amide coupling (M) from the named intermediates (Int):

| | Structure | M | Int | |
|---|---|---|---|---|
| 35 | 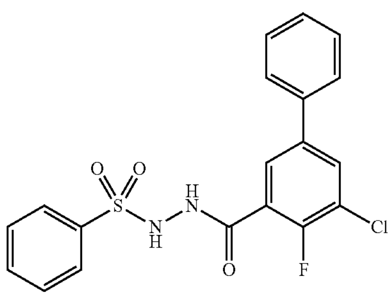 [SMILES: O=C(NNS(=O)(=O)c1ccccc1)c1cc(-c2ccccc2)cc(Cl)c1F] | C | I1 | Colourless solid (18% yield). ¹H NMR (400 MHz, DMSO) δ 10.82 (s, 1H), 10.26 (s, 1H), 8.02 (d, J = 4.2 Hz, 1H), 7.90 (d, J = 7.0 Hz, 2H), 7.78-7.30 (m, 9H). LCMS A rt 6.52 min, m/z 405.0 [M + H]⁺. |
| 36 | 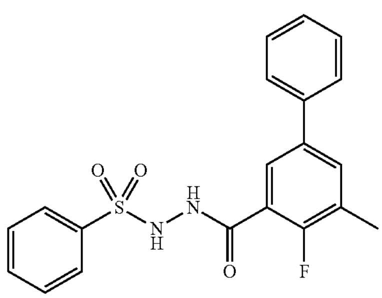 [SMILES: Cc1cc(-c2ccccc2)cc(C(=O)NNS(=O)(=O)c2ccccc2)c1F] | B | I2 | Off-white solid (35% yield). ¹H NMR (400 MHz, DMSO) δ 10.64 (s, 1H), 10.16 (s, 1H), 7.89 (d, J = 7.3 Hz, 2H), 7.72 (dd, J = 6.6, 1.7 Hz, 1H), 7.69-7.60 (m, 3H), 7.57 (t, J = 7.5 Hz, 2H), 7.48 (t, J = 7.6 Hz, 2H), 7.44-7.35 (m, 2H), 2.30 (s, 3H). LCMS A rt 6.48 min, m/z 385.1 [M + H]⁺. |
| 37 | 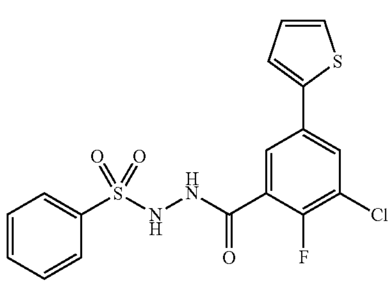 [SMILES: O=C(NNS(=O)(=O)c1ccccc1)c1cc(-c2cccs2)cc(Cl)c1F] | B | I3 | Colourless solid (60 mg, 61% yield). ¹H NMR (400 MHz, DMSO) δ 10.78 (s, 1H), 10.12 (s, 1H), 7.94 (dd, J = 6.9, 2.1 Hz, 1H), 7.84 (d, J = 7.5 Hz, 2H), 7.78 (d, J = 3.7 Hz, 1H), 7.72-7.61 (m, 2H), 7.61-7.51 (m, 3H), 7.47 (t, J = 8.9 Hz, 1H). LCMS A rt 6.55 min, m/z 411.0 [M + H]⁺. |

-continued

| | Structure | M | Int | |
|---|---|---|---|---|
| 38 | 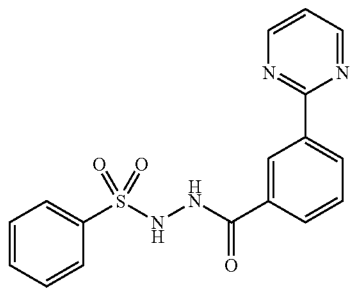 | B | P7 | Off-white solid (25 mg, 17% yield). $^1$H NMR (400 MHz, DMSO) δ 10.88 (s, 1H), 10.08 (s, 1H), 8.95 (d, J = 4.8 Hz, 2H), 8.71 (s, 1H), 8.54 (d, J = 7.8 Hz, 1H), 7.86 (d, J = 7.3 Hz, 3H), 7.74-7.30 (m, 5H). LCMS A rt 5.63 min, m/z 355.1 [M + H]$^+$. |
| 39 | 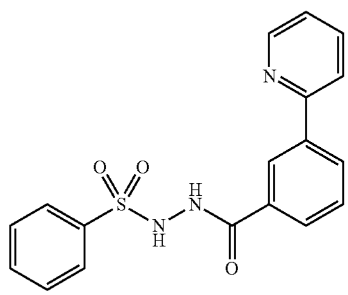 [SMILES: O=C(NNS(=O)(=O)c1ccccc1)c1cccc(-c2ccccn2)c1] | B | P1 | Colourless solid (75 mg, 48% yield). $^1$H NMR (400 MHz, DMSO) δ 10.84 (s, 1H), 10.08 (s, 1H), 8.70 (ddd, J = 4.8, 1.7, 0.9 Hz, 1H), 8.40 (s, 1H), 8.24 (d, J = 7.9 Hz, 1H), 8.01 (d, J = 8.0 Hz, 1H), 7.98-7.89 (m, 1H), 7.89-7.80 (m, 2H), 7.74 (d, J = 7.8 Hz, 1H), 7.67-7.60 (m, 1H), 7.60-7.48 (m, 3H), 7.40 (ddd, J = 7.4, 4.8, 1.0 Hz, 1H). LCMS B rt 5.40 min, m/z 354.1 [M + H]$^+$. |
| 40 | 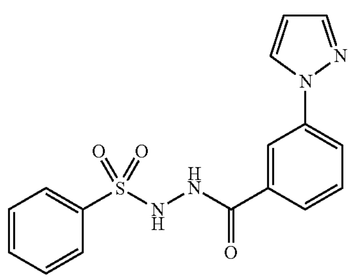 [SMILES: O=C(NNS(=O)(=O)c1ccccc1)c1cccc(-n2cccn2)c1] | B | P13 | Colourless solid (30 mg, 28% yield). $^1$H NMR (400 MHz, DMSO) δ 10.83 (s, 1H), 10.10 (s, 1H), 8.53 (s, 1H), 8.30-7.41 (m, 10H), 6.58 (s, 1H). LCMS B rt 5.73 min, m/z 343.1 [M + H]$^+$. |
| 41 | 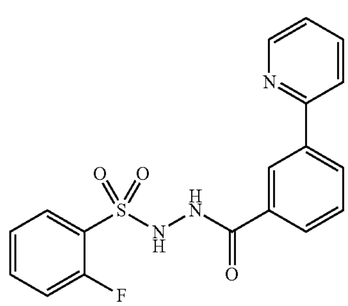 [SMILES: O=C(NNS(=O)(=O)c1ccccc1F)c1cccc(-c2ccccn2)c1] | A | P1 | Colourless solid (60% yield). $^1$H NMR (400 MHz, DMSO) δ 10.88 (d, J = 2.0 Hz, 1H), 10.35 (d, J = 2.3 Hz, 1H), 8.70 (d, J = 4.7 Hz, 1H), 8.42 (s, 1H), 8.25 (d, J = 7.9 Hz, 1H), 8.01 (d, J = 8.0 Hz, 1H), 7.93 (td, J = 7.7, 1.8 Hz, 1H), 7.82 (t, J = 7.5 Hz, 1H), 7.75 (d, J = 7.8 Hz, 1H), 7.69 (dd, J = 13.6, 7.0 Hz, 1H), 7.57 (t, J = 7.8 Hz, 1H), 7.41 (dd, J = 11.5, 6.7 Hz, 2H), 7.30 (t, J = 8.0 Hz, 1H). LCMS B rt 3.44 min, m/z 372.1 [M + H]$^+$. |
| 42 | 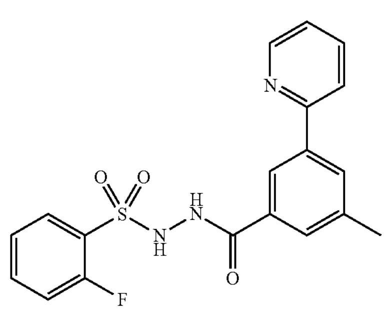 [SMILES: Cc1cc(C(=O)NNS(=O)(=O)c2ccccc2F)cc(-c2ccccn2)c1] | A | P2 | Colourless solid (72% yield). $^1$H NMR (400 MHz, DMSO) δ 10.82 (d, J = 2.4 Hz, 1H), 10.32 (d, J = 2.5 Hz, 1H), 8.68 (d, J = 4.7 Hz, 1H), 8.21 (s, 1H), 8.07 (s, 1H), 7.99 (d, J = 8.0 Hz, 1H), 7.92 (td, J = 7.7, 1.7 Hz, 1H), 7.81 (t, J = 7.5 Hz, 1H), 7.72-7.64 (m, 1H), 7.57 (s, 1H), 7.40 (t, J = 8.7 Hz, 2H), 7.30 (t, J = 8.0 Hz, 1H), 2.41 (s, 3H). LCMS B rt 3.49 min, m/z 386.1 [M + H]$^+$. |

| | Structure | M | Int | |
|---|---|---|---|---|
| 43 | 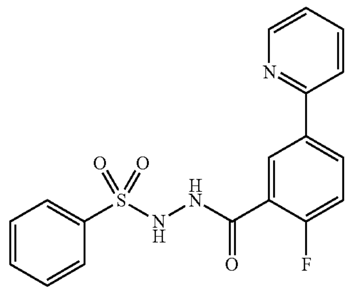 [SMILES: O=C(NNS(=O)(=O)c1ccccc1)c1cc(-c2ccccn2)ccc1F] | A | P3 | Colourless solid (65% yield). $^1$H NMR (400 MHz, DMSO) δ 10.68 (s, 1H), 10.18 (s, 1H), 8.68 (d, J = 4.8 Hz, 1H), 8.26-8.18 (m, 1H), 8.14-8.09 (m, 1H), 7.98 (d, J = 8.0 Hz, 1H), 7.94-7.86 (m, 3H), 7.65 (t, J = 7.4 Hz, 1H), 7.58 (t, J = 7.5 Hz, 2H), 7.43-7.35 (m, 2H). LCMS B rt 3.44 min, m/z 372.1 [M + H]$^+$. |
| 44 | 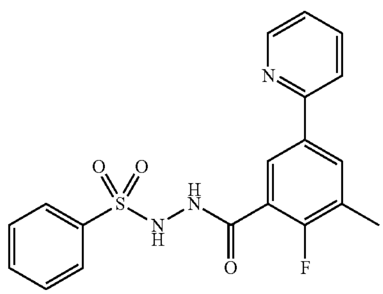 [SMILES: Cc1cc(-c2ccccn2)cc(C(=O)NNS(=O)(=O)c2ccccc2)c1F] | A | P4 | Colourless solid (67% yield). $^1$H NMR (400 MHz, DMSO) δ 10.66 (d, J = 3.3 Hz, 1H), 10.18 (d, J = 3.3 Hz, 1H), 8.67 (d, J = 4.4 Hz, 1H), 8.16-8.08 (m, 1H), 7.92 (ddd, J = 13.1, 12.7, 4.6 Hz, 5H), 7.65 (t, J = 7.4 Hz, 1H), 7.58 (t, J = 7.5 Hz, 2H), 7.38 (ddd, J = 7.1, 4.8, 1.1 Hz, 1H), 2.32 (s, 3H). LCMS B rt 3.50 min, m/z 386.1 [M + M]$^+$. |
| 45 | 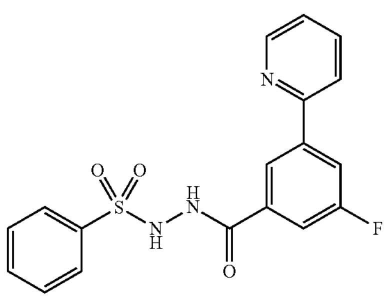 [SMILES: O=C(NNS(=O)(=O)c1ccccc1)c1cc(F)cc(-c2ccccn2)c1] | A | P5 | Colourless solid (69% yield). $^1$H NMR (400 MHz, DMSO) δ 10.94 (d, J = 2.9 Hz, 1H), 10.17 (d, J = 3.1 Hz, 1H), 8.71 (d, J = 4.6 Hz, 1H), 8.30 (s, 1H), 8.08 (t, J = 8.6 Hz, 2H), 7.95 (t, J = 8.1 Hz, 1H), 7.86 (d, J = 7.7 Hz, 2H), 7.64 (t, J = 7.3 Hz, 1H), 7.55 (t, J = 7.8 Hz, 3H), 7.44 (dd, J = 7.3, 4.9 Hz, 1H). LCMS B rt 3.55 min, m/z 372.1 [M + H]$^+$. |
| 46 | 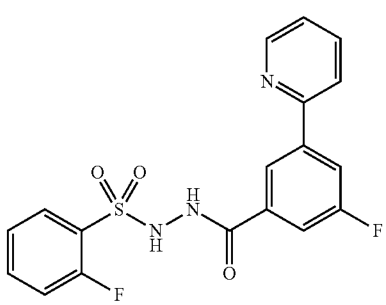 [SMILES: O=C(NNS(=O)(=O)c1ccccc1F)c1cc(F)cc(-c2ccccn2)c1] | A | P5 | Colourless solid (66% yield). $^1$H NMR (400 MHz, DMSO) δ 10.98 (br s, 1H), 10.43 (br s, 1H), 8.71 (d, J = 4.4 Hz, 1H), 8.31 (s, 1H), 8.13-8.02 (m, 2H), 7.96 (t, J = 7.7 Hz, 1H), 7.82 (t, J = 7.3 Hz, 1H), 7.70 (dd, J = 12.7, 7.3 Hz, 1H), 7.54 (d, J = 9.8 Hz, 1H), 7.43 (dd, J = 17.4, 7.9 Hz, 2H), 7.31 (t, J = 7.6 Hz, 1H). LCMS B rt 3.49 min, m/z 390.1 [M + H]$^+$. |
| 47 | 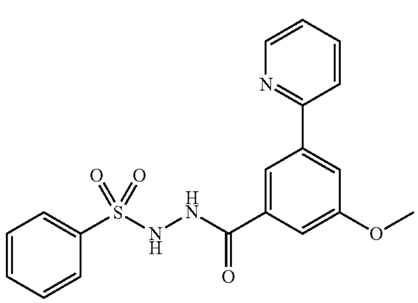 [SMILES: COc1cc(C(=O)NNS(=O)(=O)c2ccccc2)cc(-c2ccccn2)c1] | A | P6 | Colourless solid (65% yield). $^1$H NMR (400 MHz, DMSO) δ 10.83 (br s, 1H), 10.10 (br s, 1H), 8.70 (d, J = 3.6 Hz, 1H), 8.02 (d, J = 9.6 Hz, 2H), 7.93 (t, J = 7.5 Hz, 1H), 7.86 (d, J = 7.4 Hz, 2H), 7.80 (s, 1H), 7.69-7.60 (m, 1H), 7.55 (t, J = 7.4 Hz, 2H), 7.45-7.36 (m, 1H), 7.29 (s, 1H), 3.87 (s, 3H). LCMS B rt 3.48 min, m/z 384.1 [M + H]$^+$. |

| | Structure | M | Int | |
|---|---|---|---|---|
| 48 | 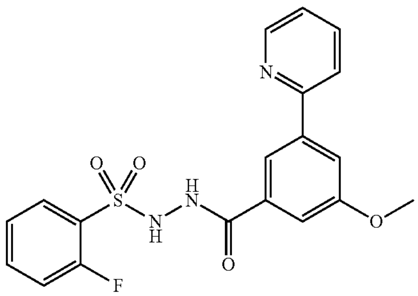 [SMILES: COc1cc(C(=O)NNS(=O)(=O)c2ccccc2F)cc(-c2ccccn2)c1] | A | P6 | Colourless solid (70% yield). $^1$H NMR (400 MHz, DMSO) δ 10.86 (d, J = 2.6 Hz, 1H), 10.34 (d, J = 2.6 Hz, 1H), 8.69 (dd, J = 6.0, 1.2 Hz, 1H), 8.04-7.98 (m, 2H), 7.92 (td, J = 7.7, 1.8 Hz, 1H), 7.84-7.77 (m, 2H), 7.73-7.65 (m, 1H), 7.41 (td, J = 8.0, 6.2 Hz, 2H), 7.33-7.26 (m, 2H), 3.86 (s, 3H). LCMS B rt 3.48 min, m/z 402.2 [M + M]$^+$. |
| 49 | 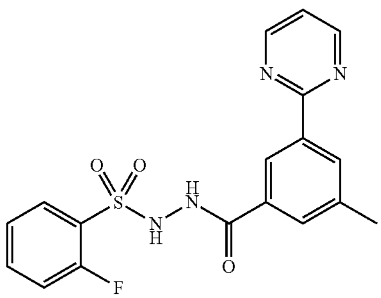 [SMILES: Cc1cc(C(=O)NNS(=O)(=O)c2ccccc2F)cc(-c2ncccn2)c1] | A | P8 | Colourless solid (67% yield). $^1$H NMR (400 MHz, DMSO) δ 10.86 (d, J = 2.5 Hz, 1H), 10.31 (d, J = 2.5 Hz, 1H), 8.93 (d, J = 4.9 Hz, 2H), 8.53 (s, 1H), 8.37 (s, 1H), 7.81 (td, J = 7.7, 1.6 Hz, 1H), 7.72-7.64 (m, 2H), 7.49 (t, J = 4.9 Hz, 1H), 7.44-7.36 (m, 1H), 7.30 (t, J = 7.7 Hz, 1H), 2.43 (s, 3H). LCMS B rt 3.69 min, m/z 387.1 [M + H]$^+$. |
| 50 | 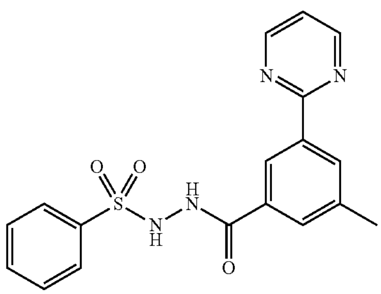 [SMILES: Cc1cc(C(=O)NNS(=O)(=O)c2ccccc2)cc(-c2ncccn2)c1] | A | P8 | Colourless solid (58% yield). $^1$H NMR (400 MHz, DMSO) δ 10.83 (br s, 1H), 10.08 (br s, 1H), 8.93 (d, J = 4.8 Hz, 2H), 8.52 (s, 1H), 8.37 (s, 1H), 7.86 (d, J = 7.5 Hz, 2H), 7.68 (s, 1H), 7.63 (t, J = 7.3 Hz, 1H), 7.54 (t, J = 7.6 Hz, 2H), 7.48 (t, J = 4.8 Hz, 1H), 2.43 (s, 3H). LCMS B rt 3.54 min, m/z 369.1 [M + H]$^+$. |
| 51 | 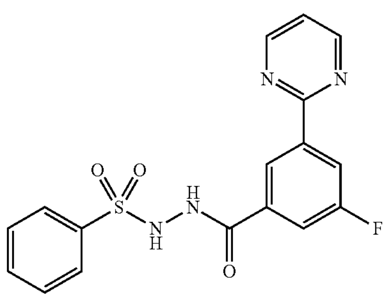 [SMILES: O=C(NNS(=O)(=O)c1ccccc1)c1cc(F)cc(-c2ncccn2)c1] | A | P11 | Colourless solid (69% yield). $^1$H NMR (400 MHz, DMSO) δ 11.00 (d, J = 2.4 Hz, 1H), 10.18 (d, J = 2.7 Hz, 1H), 8.98 (d, J = 4.8 Hz, 2H), 8.59 (s, 1H), 8.26 (d, J = 9.4 Hz, 1H), 7.87 (d, J = 7.7 Hz, 2H), 7.66 (dd, J = 19.9, 8.1 Hz, 2H), 7.56 (t, J = 6.5 Hz, 3H). LCMS B rt 3.55 min, m/z 373.2 [M + H]$^+$. |
| 52 | 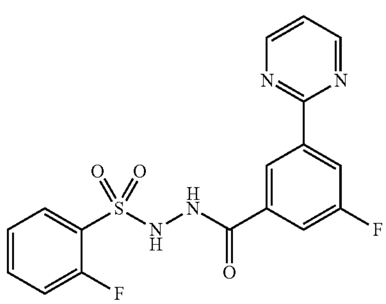 [SMILES: O=C(NNS(=O)(=O)c1ccccc1F)c1cc(F)cc(-c2ncccn2)c1] | A | P11 | Colourless solid (66% yield). $^1$H NMR (400 MHz, DMSO) δ 11.03 (d, J = 2.5 Hz, 1H), 10.43 (d, J = 2.5 Hz, 1H), 8.97 (d, J = 4.9 Hz, 2H), 8.60 (s, 1H), 8.26 (d, J = 11.1 Hz, 1H), 7.82 (t, J = 7.5 Hz, 1H), 7.70 (dd, J = 15.1, 9.0 Hz, 2H), 7.54 (t, J = 4.9 Hz, 1H), 7.45-7.38 (m, 1H), 7.31 (t, J = 7.6 Hz, 1H). LCMS B rt 3.61 min, m/z 391.1 [M + H]$^+$. |

|   | Structure | M | Int | |
|---|---|---|---|---|
| 53 | 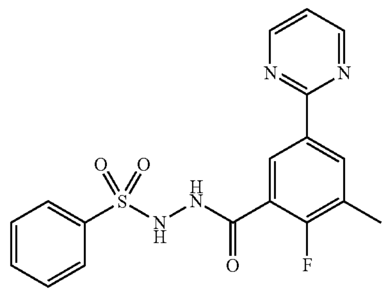 [SMILES: Cc1cc(-c2ncccn2)cc(C(=O)NNS(=O)(=O)c2ccccc2)c1F] | A | P10 | Colourless solid (67% yield). ¹H NMR (400 MHz, DMSO) δ 10.69 (d, J = 3.0 Hz, 1H), 10.20 (d, J = 3.1 Hz, 1H), 8.92 (d, J = 4.9 Hz, 2H), 8.41 (d, J = 6.7 Hz, 1H), 8.24 (dd, J = 6.0, 1.6 Hz, 1H), 7.93-7.85 (m, 2H), 7.65 (t, J = 7.3 Hz, 1H), 7.58 (t, J = 7.4 Hz, 2H), 7.48 (t, J = 4.9 Hz, 1H), 2.34 (s, 3H). LCMS B rt 3.51 min, m/z 387.1 [M + H]⁺. |
| 54 | 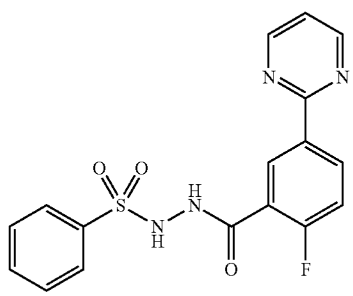 [SMILES: O=C(NNS(=O)(=O)c1ccccc1)c1cc(-c2ncccn2)ccc1F] | A | P9 | Colourless solid (65% yield). ¹H NMR (400 MHz, DMSO) δ 10.71 (br s, 1H), 10.21 (br s, 1H), 8.93 (d, J = 4.9 Hz, 2H), 8.51 (ddd, J = 8.6, 5.0, 2.3 Hz, 1H), 8.43 (dd, J = 6.8, 2.3 Hz, 1H), 7.92-7.84 (m, 2H), 7.65 (ddd, J = 6.5, 2.4, 1.2 Hz, 1H), 7.58 (t, J = 7.5 Hz, 2H), 7.46 (dt, J = 18.5, 6.9 Hz, 2H). LCMS B rt 3.50 min, m/z 373.1 [M + H]⁺. |
| 55 | 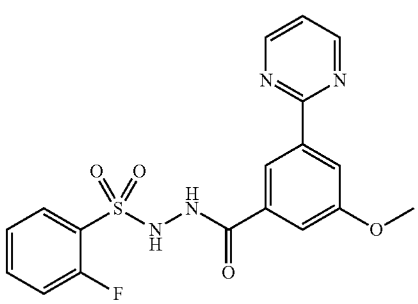 [SMILES: COc1cc(C(=O)NNS(=O)(=O)c2ccccc2F)cc(-c2ncccn2)c1] | A | P12 | Colourless solid (54% yield). ¹H NMR (400 MHz, DMSO) δ 10.90 (br s, 1H), 10.34 (br s, 1H), 8.94 (d, J = 4.9 Hz, 2H), 8.33 (d, J = 1.4 Hz, 1H), 8.07-8.02 (m, 1H), 7.82 (dd, J = 11.2, 3.7 Hz, 1H), 7.69 (dd, J = 12.4, 6.5 Hz, 1H), 7.50 (t, J = 4.9 Hz, 1H), 7.45-7.36 (m, 2H), 7.33-7.25 (m, 1H), 3.87 (s, 3H). LCMS B rt 3.46 min, m/z 403.1 [M + H]⁺. |
| 56 | 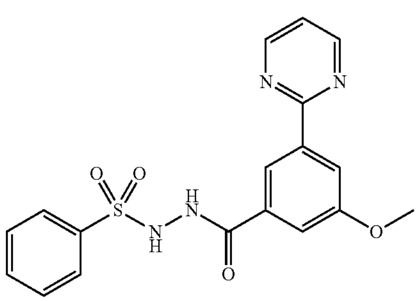 [SMILES: COc1cc(C(=O)NNS(=O)(=O)c2ccccc2)cc(-c2ncccn2)c1] | A | P12 | Colorless solid (65% yield). ¹H NMR (400 MHz, DMSO) δ 10.87 (br s, 1H), 10.10 (br s, 1H), 8.95 (d, J = 4.9 Hz, 2H), 8.33 (s, 1H), 8.07 (s, 1H), 7.86 (d, J = 7.8 Hz, 2H), 7.64 (t, J = 7.4 Hz, 1H), 7.53 (dt, J = 9.7, 6.4 Hz, 3H), 7.42 (s, 1H), 3.88 (s, 3H). LCMS B rt 3.45 min, m/z 385.1 [M + H]⁺. |
| 57 | 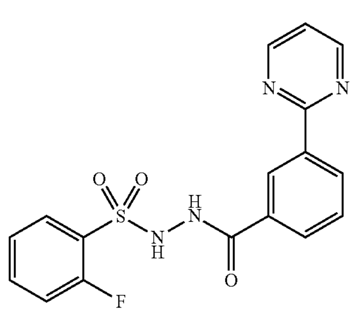 [SMILES: O=C(NNS(=O)(=O)c1ccccc1F)c1cccc(-c2ncccn2)c1] | A | P7 | Colourless solid (66% yield). ¹H NMR (400 MHz, DMSO) δ 10.92 (d, J = 2.5 Hz, 1H), 10.34 (d, J = 2.5 Hz, 1H), 8.94 (d, J = 4.9 Hz, 2H), 8.73 (d, J = 1.5 Hz, 1H), 8.54 (d, J = 5.1 Hz, 1H), 7.88-7.78 (m, 2H), 7.73-7.65 (m, 1H), 7.61 (t, J = 7.8 Hz, 1H), 7.50 (t, J = 4.9 Hz, 1H), 7.44-7.37 (m, 1H), 7.30 (td, J = 7.7, 1.0 Hz, 1H). LCMS B rt 3.44 min, m/z 373.1 [M + H]⁺. |

| | Structure | M | Int | |
|---|---|---|---|---|
| 58 | 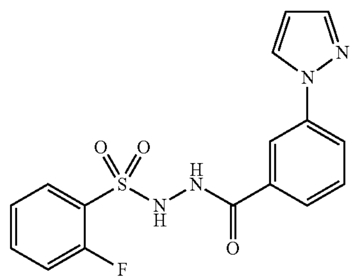 [SMILES: O=C(NNS(=O)(=O)c1ccccc1F)c1cccc(-n2cccn2)c1] | A | P13 | Colourless solid (68% yield). $^1$H NMR (400 MHz, DMSO) δ 10.88 (d, J = 2.1 Hz, 1H), 10.37 (d, J = 2.3 Hz, 1H), 8.52 (d, J = 2.4 Hz, 1H), 8.15 (s, 1H), 8.01 (d, J = 7.8 Hz, 1H), 7.87-7.76 (m, 2H), 7.69 (dd, J = 13.7, 8.7 Hz, 1H), 7.59 (dt, J = 15.5, 7.7 Hz, 2H), 7.46-7.35 (m, 1H), 7.30 (t, J = 8.0 Hz, 1H), 6.61-6.50 (m, 1H). LCMS B rt 3.47 min, m/z 361.1 [M + H]$^+$. |
| 59 | 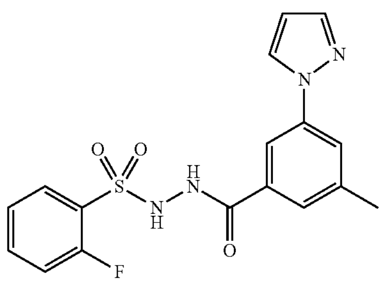 [SMILES: Cc1cc(C(=O)NNS(=O)(=O)c2ccccc2F)cc(-n2cccn2)c1] | A | P14 | Colourless solid (71% yield). $^1$H NMR (400 MHz, DMSO) δ 10.81 (s, 1H), 10.36 (s, 1H), 8.48 (d, J = 2.5 Hz, 1H), 7.95 (s, 1H), 7.87-7.75 (m, 3H), 7.73-7.63 (m, 1H), 7.41 (dd, J = 17.2, 7.3 Hz, 2H), 7.30 (t, J = 7.6 Hz, 1H), 6.60-6.48 (m, 1H), 2.39 (s, 3H). LCMS B rt 3.52 min. m/z 374.1 [M + H]$^+$. |
| 60 | 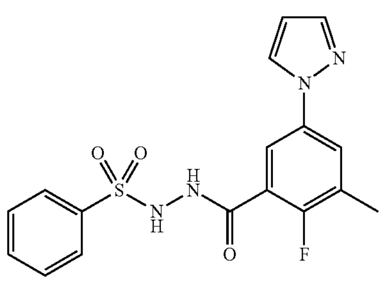 [SMILES: Cc1cc(-n2cccn2)cc(C(=O)NNS(=O)(=O)c2ccccc2)c1F] | A | P16 | Colourless solid (67% yield). $^1$H NMR (400 MHz, DMSO) δ 10.67 (br s, 1H), 10.22 (br s, 1H), 8.49 (d, J = 2.5 Hz, 1H), 7.95-7.86 (m, 3H), 7.77 (d, J = 1.6 Hz, 1H), 7.68-7.61 (m, 2H), 7.58 (t, J = 7.5 Hz, 2H), 6.58-6.53 (m, 1H), 2.32 (d, J = 1.4 Hz, 3H). LCMS B rt 3.57 min, m/z 375.2 [M + H]$^+$. |
| 61 | 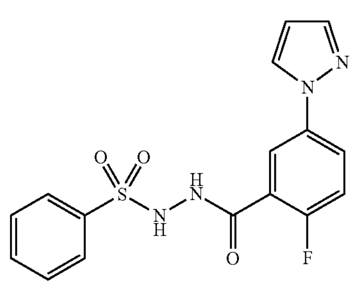 [SMILES: O=C(NNS(=O)(=O)c1ccccc1)c1cc(-n2cccn2)ccc1F] | A | P15 | Colourless solid (78% yield). $^1$H NMR (400 MHz, DMSO) δ 10.71 (s, 1H), 10.21 (s, 1H), 8.52 (d, J = 2.2 Hz, 1H), 8.04-7.95 (m, 1H), 7.89 (d, J = 7.5 Hz, 2H), 7.83 (dd, J = 5.7, 2.7 Hz, 1H), 7.77 (s, 1H), 7.65 (t, J = 7.3 Hz, 1H), 7.58 (t, J = 7.5 Hz, 2H), 7.43 (t, J = 9.2 Hz, 1H), 6.56 (s, 1H). LCMS B rt 3.46 min, m/z 361.1 [M + H]$^+$. |
| 62 | 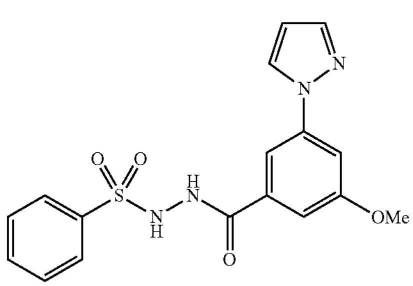 [SMILES: COc1cc(C(=O)NNS(=O)(=O)c2ccccc2)cc(-n2cccn2)c1] | A | P18 | Colourless solid (63% yield). $^1$H NMR (400 MHz, DMSO) δ 10.82 (s, 1H), 10.11 (s, 1H), 8.54 (d, J = 2.3 Hz, 1H), 7.89-7.82 (m, 2H), 7.79-7.72 (m, 2H), 7.64 (t, J = 7.4 Hz, 1H), 7.55 (dd, J = 10.8, 4.1 Hz, 3H), 7.16 (s, 1H), 6.59-6.53 (m, 1H), 3.85 (s, 3H). LCMS B rt 3.56 min, m/z 372.1 [M + H]$^+$. |

| | Structure | M | Int | |
|---|---|---|---|---|
| 63 | 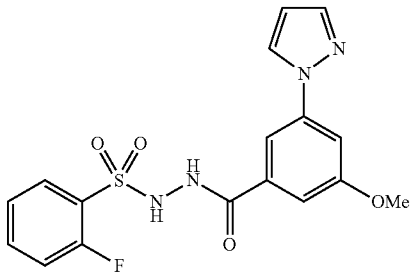 [SMILES: COc1cc(C(=O)NNS(=O)(=O)c2ccccc2F)cc(-n2cccn2)c1] | A | P18 | Colourless solid (72% yield). $^1$H NMR (400 MHz, DMSO) δ 10.85 (d, J = 2.2 Hz, 1H), 10.37 (d, J = 2.4 Hz, 1H), 8.54 (d, J = 2.4 Hz, 1H), 7.81 (t, J = 6.9 Hz, 1H), 7.76 (d, J = 6.0 Hz, 2H), 7.70 (dd, J = 13.2, 7.4 Hz, 1H), 7.57 (s, 1H), 7.46-7.37 (m, 1H), 7.31 (t, J = 7.6 Hz, 1H), 7.17 (s, 1H), 6.64-6.47 (m, 1H), 3.85 (s, 3H). LCMS B rt 3.53 min, m/z 391.1 [M + H]$^+$. |
| 64 | 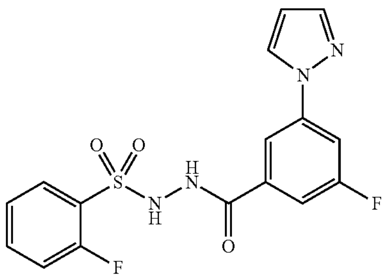 [SMILES: O=C(NNS(=O)(=O)c1ccccc1F)c1cc(F)cc(-n2cccn2)c1] | A | P17 | Colourless solid (67% yield). $^1$H NMR (400 MHz, DMSO) δ 10.97 (s, 1H), 10.45 (s, 1H), 8.58 (d, J = 2.4 Hz, 1H), 8.06 (s, 1H), 7.95 (dt, J = 10.1, 2.1 Hz, 1H), 7.84-7.78 (m, 2H), 7.70 (ddd, J = 8.2, 7.4, 1.7 Hz, 1H), 7.45-7.38 (m, 2H), 7.34-7.28 (m, 1H), 6.61 (dd, J = 2.5, 1.8 Hz, 1H). LCMS B rt 3.57 min, m/z 379.1 [M + H]$^+$. |
| 65 | 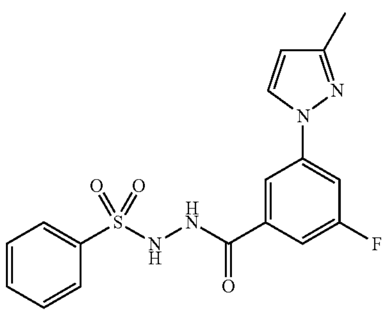 | A | P17 | Colourless solid (60% yield). $^1$H NMR (400 MHz, DMSO) δ 10.93 (d, J = 1.9 Hz, 1H), 10.19 (d, J = 2.6 Hz, 1H), 8.59 (d, J = 2.5 Hz, 1H), 8.05 (s, 1H), 7.94 (d, J = 10.0 Hz, 1H), 7.84 (dd, J = 18.2, 4.4 Hz, 3H), 7.64 (t, J = 7.4 Hz, 1H), 7.55 (t, J = 7.6 Hz, 2H), 7.41 (d, J = 8.7 Hz, 1H), 6.63-6.58 (m, 1H), 2.25 (s, 3H). LCMS B rt 3.52 min, m/z 360.1 [M + H]$^+$. |
| 66 | 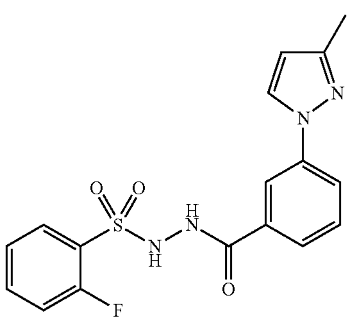 [SMILES: Cc1ccn(-c2cccc(C(=O)NNS(=O)(=O)c3ccccc3F)c2)n1] | A | P19 | Colourless solid (68% yield). $^1$H NMR (400 MHz, DMSO) δ 10.87 (d, J = 1.8 Hz, 1H), 10.36 (d, J = 2.1 Hz, 1H), 8.38 (d, J = 2.2 Hz, 1H), 8.10 (s, 1H), 7.94 (d, J = 7.7 Hz, 1H), 7.81 (t, J = 6.9 Hz, 1H), 7.69 (dd, J = 12.3, 6.8 Hz, 1H), 7.55 (dt, J = 15.5, 7.6 Hz, 2H), 7.45-7.37 (m, 1H), 7.30 (t, J = 7.6 Hz, 1H), 6.36 (d, J = 2.2 Hz, 1H), 2.28 (s, 3H). LCMS B rt 3.51 min, m/z 375.1 [M + H]$^+$. |
| 67 | 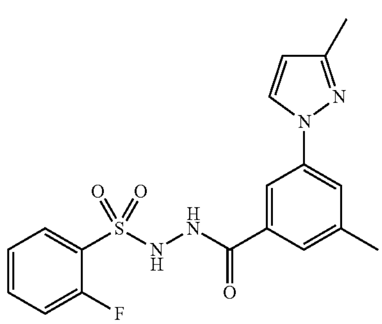 [SMILES: Cc1cc(C(=O)NNS(=O)(=O)c2ccccc2F)cc(-n2ccc(C)n2)c1] | A | P20 | Colourless solid (71% yield). $^1$H NMR (400 MHz, DMSO) δ 10.79 (s, 1H), 10.34 (s, 1H), 8.35 (d, J = 2.1 Hz, 1H), 7.90 (s, 1H), 7.86-7.79 (m, 2H), 7.69 (dd, J = 12.4, 6.7 Hz, 1H), 7.40 (t, J = 9.2 Hz, 2H), 7.30 (t, J = 7.6 Hz, 1H), 6.35 (d, J = 2.2 Hz, 1H), 2.37 (s, 3H), 2.27 (s, 3H). LCMS B rt 3.66 min, m/z 389.1 [M + H]$^+$. |

| | Structure | M | Int | |
|---|---|---|---|---|
| 68 | 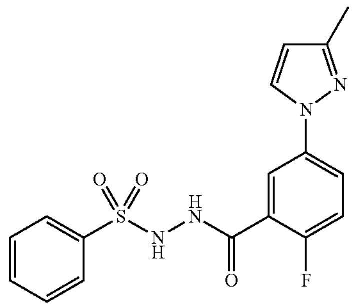 [SMILES: Cc1ccn(-c2ccc(F)c(C(=O)NNS(=O)(=O)c3ccccc3)c2)n1] | A | P21 | Colourless solid (78% yield). ¹H NMR (400 MHz, DMSO) δ 10.67 (s, 1H), 10.20 (s, 1H), 8.38 (d, J = 2.4 Hz, 1H), 7.95-7.85 (m, 3H), 7.81-7.75 (m, 1H), 7.66 (t, J = 8.0 Hz, 1H), 7.61-7.53 (m, 2H), 7.39 (t, J = 9.3 Hz, 1H), 6.35 (d, J = 2.4 Hz, 1H), 2.27 (s, 3H). LCMS B rt 3.57 min, m/z 375.1 [M + H]⁺. |
| 69 | 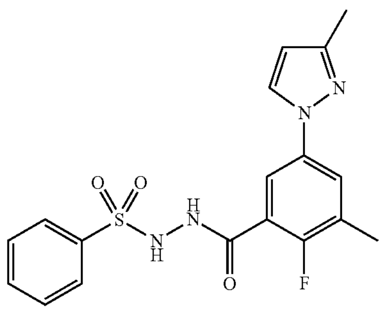 [SMILES: Cc1ccn(-c2cc(C)c(F)c(C(=O)NNS(=O)(=O)c3ccccc3)c2)n1] | A | P22 | Colourless solid (60% yield). ¹H NMR (400 MHz, DMSO) δ 10.65 (s, 1H), 10.19 (s, 1H), 8.34 (d, J = 2.0 Hz, 1H), 7.89 (d, J = 7.8 Hz, 2H), 7.85 (d, J = 5.5 Hz, 1H), 7.66 (t, J = 7.3 Hz, 1H), 7.58 (t, J = 7.5 Hz, 3H), 6.34 (d, J = 2.0 Hz, 1H), 2.30 (s, 3H), 2.27 (s, 3H). LCMS B rt 3.62 min m/z 389.1 [M + H]⁺. |
| 70 | 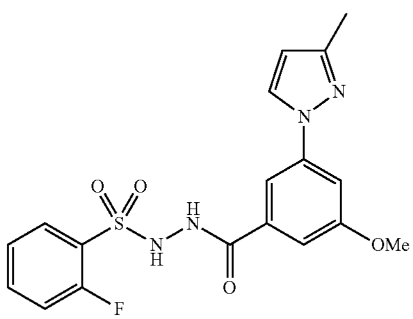 [SMILES: COc1cc(C(=O)NNS(=O)(=O)c2ccccc2F)cc(-n2ccc(C)n2)c1] | A | P24 | Colourless solid (69% yield). ¹H NMR (400 MHz, DMSO) δ 10.84 (d, J = 2.3 Hz, 1H), 10.36 (d, J = 2.4 Hz, 1H), 8.40 (d, J = 2.3 Hz, 1H), 7.81 (t, J = 7.5 Hz, 1H), 7.74-7.67 (m, 2H), 7.50 (s, 1H), 7.45-7.37 (m, 1H), 7.31 (t, J = 7.6 Hz, 1H), 7.13 (s, 1H), 6.36 (d, J = 2.3 Hz, 1H), 3.85 (s, 3H), 2.27 (s, 3H). LCMS B rt 3.60 min, m/z 405.1 [M + H]⁺. |
| 71 | 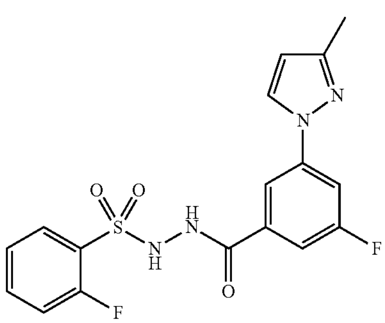 [SMILES: Cc1ccn(-c2cc(F)cc(C(=O)NNS(=O)(=O)c3ccccc3F)c2)n1] | A | P23 | Colourless solid (59% yield). ¹H NMR (400 MHz, DMSO) δ 10.96 (s, 1H), 10.44 (s, 1H), 8.45 (d, J = 2.4 Hz, 1H), 8.01 (s, 1H), 7.88 (d, J = 10.2 Hz, 1H), 7.82 (t, J = 7.5 Hz, 1H), 7.75-7.66 (m, 1H), 7.37 (ddd, J = 23.2, 17.1, 8.9 Hz, 3H), 6.40 (d, J = 2.4 Hz, 1H), 2.29 (s, 3H). LCMS B rt 3.25 min, m/z 393.1 [M + H]⁺. |
| 72 | 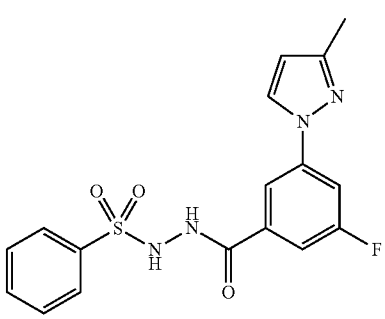 [SMILES: Cc1ccn(-c2cc(F)cc(C(=O)NNS(=O)(=O)c3ccccc3)c2)n1] | A | P23 | Colourless solid (54% yield). ¹H NMR (400 MHz, DMSO) δ 10.92 (s, 1H), 10.20 (s, 1H), 8.45 (d, J = 2.5 Hz, 1H), 7.99 (s, 1H), 7.86 (dd, J = 10.3, 3.1 Hz, 3H), 7.64 (t, J = 7.4 Hz, 1H), 7.55 (t, J = 7.6 Hz, 2H), 7.36 (d, J = 8.4 Hz, 1H), 6.40 (d, J = 2.4 Hz, 1H), 2.28 (s, 3H). LCMS B rt 3.23 min, m/z 375.1 [M + H]⁺. |

-continued

| | Structure | M | Int | |
|---|---|---|---|---|
| 73 | 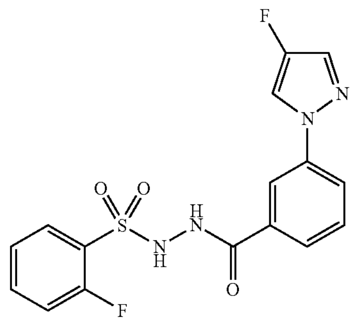 [SMILES: O=C(NNS(=O)(=O)c1ccccc1F)c1cccc(-n2cc(F)cn2)c1] | A | P30 | Colourless solid (67% yield). $^1$H NMR (400 MHz, DMSO) δ 10.88 (d, J = 2.0 Hz, 1H), 10.38 (d, J = 2.2 Hz, 1H), 8.72 (d, J = 4.5 Hz, 1H), 8.11 (s, 1H), 7.98-7.91 (m, 1H), 7.88 (d, J = 4.2 Hz, 1H), 7.81 (t, J = 7.5 Hz, 1H), 7.69 (tt, J = 4.9, 4.3 Hz, 1H), 7.60 (dt, J = 15.6, 7.8 Hz, 2H), 7.44-7.35 (m, 1H), 7.33-7.25 (m, 1H). LCMS B rt 3.58 min, m/z 379.1 [M + H]$^+$. |
| 74 | 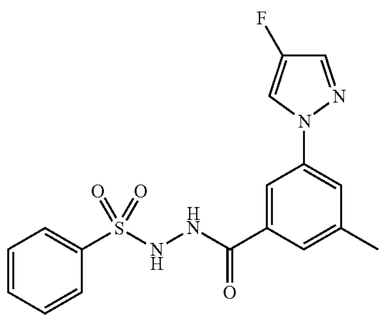 [SMILES: Cc1cc(C(=O)NNS(=O)(=O)c2ccccc2)cc(-n2cc(F)cn2)c1] | A | P31 | Colourless solid (55% yield). $^1$H NMR (400 MHz, DMSO) δ 10.75 (s, 1H), 10.18 (s, 1H), 8.68 (d, J = 4.5 Hz, 1H), 7.87 (dd, J = 12.7, 8.8 Hz, 4H), 7.79 (s, 1H), 7.63 (t, J = 7.4 Hz, 1H), 7.54 (t, J = 7.6 Hz, 2H), 7.45 (s, 1H), 2.39 (s, 3H). LCMS B rt 3.65 min, m/z 375.2 [M + H]$^+$. |
| 75 | 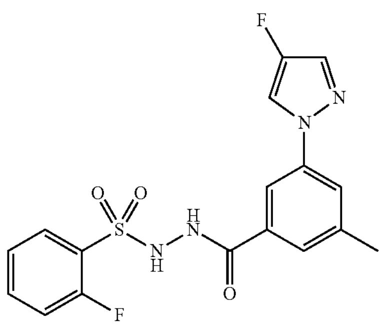 [SMILES: Cc1cc(C(=O)NNS(=O)(=O)c2ccccc2F)cc(-n2cc(F)cn2)c1] | A | P31 | Colourless solid (67% yield). $^1$H NMR (400 MHz, DMSO) δ 10.75 (s, 1H), 10.29 (s, 1H), 8.61 (d, J = 4.4 Hz, 1H), 7.85 (s, 1H), 7.80 (d, J = 4.2 Hz, 1H), 7.77-7.70 (m, 2H), 7.62 (dd, J = 13.3, 7.2 Hz, 1H), 7.40 (s, 1H), 7.37-7.30 (m, 1H), 7.27-7.20 (m, 1H), 2.32 (s, 3H). LCMS B rt 3.67 min, m/z 393.1 [M + H]$^+$. |
| 76 | 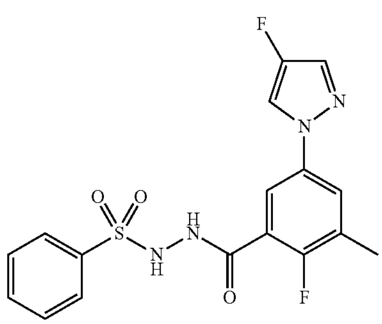 [SMILES: Cc1cc(-n2cc(F)cn2)cc(C(=O)NNS(=O)(=O)c2ccccc2)c1F] | A | P32 | Colourless solid (69% yield). $^1$H NMR (400 MHz, DMSO) δ 10.66 (s, 1H), 10.21 (s, 1H), 8.69 (d, J = 4.2 Hz, 1H), 7.91-7.82 (m, 4H), 7.68-7.61 (m, 1H), 7.61-7.54 (m, 3H), 2.30 (d, J = 1.5 Hz, 3H). LCMS B rt 3.65 min, m/z 391.1 [M − H]$^-$. |
| 77 | 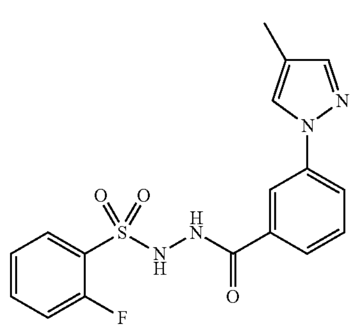 [SMILES: Cc1cnn(-c2cccc(C(=O)NNS(=O)(=O)c3ccccc3F)c2)c1] | A | P25 | Colourless solid (65% yield). $^1$H NMR (400 MHz, DMSO) δ 10.89 (s, 1H), 10.37 (s, 1H), 8.31 (s, 1H), 8.11 (s, 1H), 7.94 (d, J = 7.6 Hz, 1H), 7.82 (t, J = 7.4 Hz, 1H), 7.75-7.64 (m, 1H), 7.62-7.51 (m, 3H), 7.47-7.35 (m, 1H), 7.30 (t, J = 7.6 Hz, 1H), 2.11 (s, 3H). LCMS B rt 3.55 min, m/z 375.1 [M + H]$^+$. |

| | Structure | M | Int | |
|---|---|---|---|---|
| 78 | 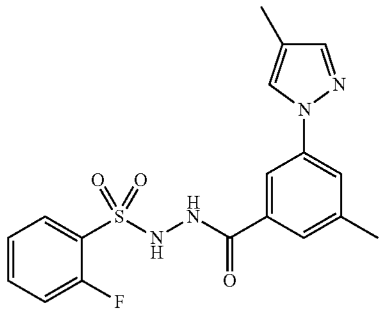 [SMILES: Cc1cc(C(=O)NNS(=O)(=O)c2ccccc2F)cc(-n2cc(C)cn2)c1] | A | P26 | Colourless solid (70% yield). $^1$H NMR (400 MHz, DMSO) δ 10.79 (s, 1H), 10.34 (s, 1H), 8.26 (s, 1H), 7.90 (s, 1H), 7.82 (d, J = 7.5 Hz, 2H), 7.74-7.64 (m, 1H), 7.58 (s, 1H), 7.44-7.35 (m, 2H), 7.30 (t, J = 7.6 Hz, 1H), 2.38 (s, 3H), 2.10 (s, 3H). LCMS B rt 3.61 min, m/z 389.1 [M + H]$^+$. |
| 79 | 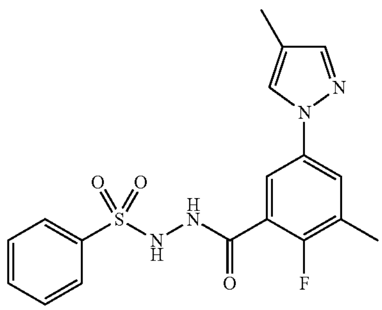 [SMILES: Cc1cnn(-c2cc(C)c(F)c(C(=O)NNS(=O)(=O)c3ccccc3)c2)c1] | A | P28 | Colourless solid (69% yield). $^1$H NMR (400 MHz, DMSO) δ 10.65 (s, 1H), 10.19 (s, 1H), 8.24 (s, 1H), 7.88 (d, J = 7.5 Hz, 2H), 7.83 (s, 1H), 7.67-7.61 (m, 1H), 7.58 (d, J = 7.3 Hz, 4H), 2.29 (s, 3H), 2.09 (s, 3H). LCMS B rt 3.58 min, m/z 389.1 [M + H]$^+$. |
| 80 | 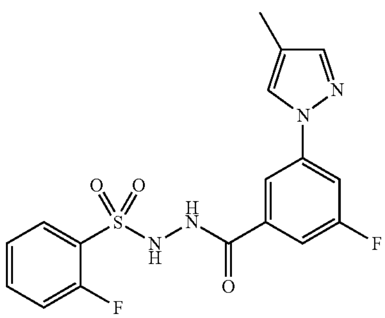 [SMILES: Cc1cnn(-c2cc(F)cc(C(=O)NNS(=O)(=O)c3ccccc3F)c2)c1] | A | P29 | Colourless solid (60% yield). $^1$H NMR (400 MHz, DMSO) δ 10.95 (s, 1H), 10.44 (s, 1H), 8.34 (s, 1H), 8.01-7.98 (m, 1H), 7.88-7.77 (m, 2H), 7.70 (ddd, J = 13.3, 7.3, 1.7 Hz, 1H), 7.63 (s, 1H), 7.45-7.27 (m, 3H), 2.10 (s, 3H). LCMS B rt 3.61 min, m/z 393.1 [M + H]$^+$. |
| 81 | 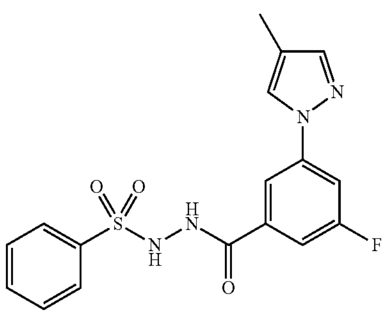 [SMILES: Cc1cnn(-c2cc(F)cc(C(=O)NNS(=O)(=O)c3ccccc3)c2)c1] | A | P29 | Colourless solid (55% yield). $^1$H NMR (400 MHz, DMSO) δ 10.91 (s, 1H), 10.17 (s, 1H), 8.35 (s, 1H), 7.99 (s, 1H), 7.85 (d, J = 7.4 Hz, 3H), 7.67-7.60 (m, 2H), 7.55 (t, J = 7.6 Hz, 2H), 7.36 (d, J = 8.9 Hz, 1H), 2.10 (s, 3H). LCMS B rt 3.59 min, m/z 375.2 [M + H]$^+$. |
| 82 | 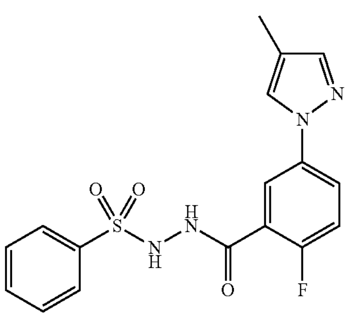 [SMILES: Cc1cnn(-c2ccc(F)c(C(=O)NNS(=O)(=O)c3ccccc3)c2)c1] | A | P27 | Colourless solid (63% yield). $^1$H NMR (400 MHz, DMSO) δ 10.67 (s, 1H), 10.21 (s, 1H), 8.29 (s, 1H), 7.89 (d, J = 7.2 Hz, 3H), 7.77 (dd, J = 5.8, 2.8 Hz, 1H), 7.66 (t, J = 7.4 Hz, 1H), 7.61-7.53 (m, 3H), 7.40 (t, J = 9.3 Hz, 1H), 2.10 (s, 3H). LCMS B rt 3.56 min, m/z 375.1 [M + H]$^+$. |

| | Structure | M | Int | |
|---|---|---|---|---|
| 83 | 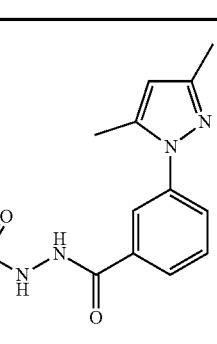 | A | P36 | Colourless solid (62% yield). $^1$H NMR (400 MHz, DMSO) δ 10.87 (d, J = 2.5 Hz, 1H), 10.35 (d, J = 2.6 Hz, 1H), 7.83-7.77 (m, 2H), 7.73-7.65 (m, 2H), 7.56 (t, J = 7.9 Hz, 1H), 7.40 (dd, J = 13.1, 5.6 Hz, 2H), 7.34-7.26 (m, 1H), 6.09 (s, 1H), 2.29 (s, 3H), 2.18 (s, 3H). LCMS B rt 3.49 min, m/z 389.2 [M + H]$^+$. |
| 84 | 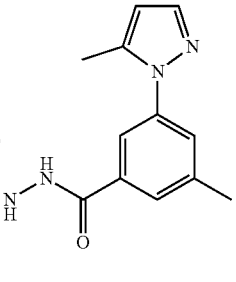 | A | P33 | Colourless solid (63% yield). $^1$H NMR (400 MHz, DMSO) δ 10.79 (s, 1H), 10.33 (s, 1H), 8.35 (d, J = 2.4 Hz, 1H), 7.90 (s, 1H), 7.81 (dd, J = 10.7, 3.2 Hz, 2H), 7.69 (dd, J = 14.2, 8.1 Hz, 1H), 7.40 (t, J = 9.2 Hz, 2H), 7.30 (td, J = 7.8, 0.9 Hz, 1H), 6.35 (d, J = 2.4 Hz, 1H), 2.38 (s, 3H), 2.27 (s, 3H). LCMS B rt 3.58 min, m/z 389.1 [M + H]$^+$. |
| 85 | 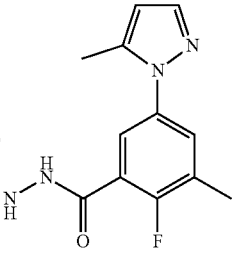 | A | P34 | Colourless solid (69% yield). $^1$H NMR (400 MHz, DMSO) δ 10.63 (s, 1H), 10.18 (s, 1H), 8.34 (d, J = 2.4 Hz, 1H), 7.89 (d, J = 7.4 Hz, 2H), 7.84 (dd, J = 6.0, 2.6 Hz, 1H), 7.65 (t, J = 7.4 Hz, 1H), 7.61-7.54 (m, 3H), 6.34 (d, J = 2.4 Hz, 1H), 2.29 (d, J = 1.5 Hz, 3H), 2.26 (s, 3H). LCMS B rt 3.58 min, m/z 389.2 [M + H]$^+$. |
| 86 | 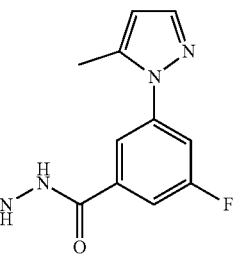 | A | P35 | Colourless solid (60% yield). $^1$H NMR (400 MHz, DMSO) δ 10.95 (s, 1H), 10.43 (s, 1H), 8.44 (d, J = 2.4 Hz, 1H), 8.00 (s, 1H), 7.87 (dt, J = 10.2, 2.1 Hz, 1H), 7.81 (td, J = 7.7, 1.6 Hz, 1H), 7.70 (ddd, J = 8.1, 4.9, 1.6 Hz, 1H), 7.47-7.27 (m, 3H), 6.39 (d, J = 2.4 Hz, 1H), 2.28 (s, 3H). LCMS B rt 3.60 min, m/z 393.1 [M + H]$^+$. |
| 87 | 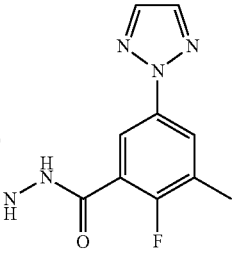 | A | P39 | Colourless solid (52% yield). $^1$H NMR (400 MHz, DMSO) δ 10.76 (s, 1H), 10.25 (s, 1H), 8.15 (s, 2H), 8.08 (dd, J = 5.9, 2.4 Hz, 1H), 7.92-7.86 (m, 2H), 7.79 (dd, J = 5.2, 2.7 Hz, 1H), 7.66 (t, J = 7.9 Hz, 1H), 7.58 (t, J = 7.5 Hz, 2H), 2.35 (d, J = 1.5 Hz, 3H). LCMS B rt 3.56 min, m/z 376.1 [M + H]$^+$. |

| | Structure | M | Int | |
|---|---|---|---|---|
| 88 | 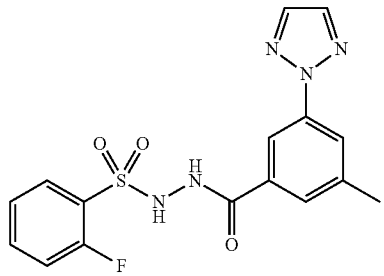 [SMILES: Cc1cc(C(=O)NNS(=O)(=O)c2ccccc2F)cc(-n2nccn2)c1] | A | P37 | Colourless solid (62% yield). $^1$H NMR (400 MHz, DMSO) δ 10.93 (s, 1H), 10.37 (s, 1H), 8.15 (s, 2H), 8.14 (s, 1H), 8.03 (s, 1H), 7.81 (td, J = 7.6, 1.6 Hz, 1H), 7.69 (ddd, J = 8.1, 5.0, 1.7 Hz, 1H), 7.57 (s, 1H), 7.45-7.35 (m, 1H), 7.30 (td, J = 7.7, 0.9 Hz, 1H), 2.43 (s, 3H). LCMS B rt 3.58 min, m/z 376.2 [M + H]$^+$. |
| 89 | 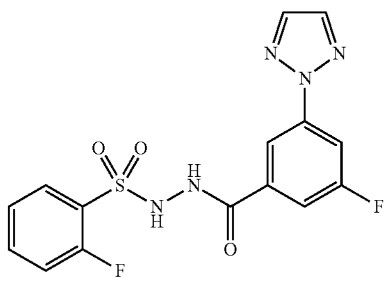 [SMILES: O=C(NNS(=O)(=O)c1ccccc1F)c1cc(F)cc(-n2nccn2)c1] | A | P38 | Colourless solid (60% yield). $^1$H NMR (400 MHz, DMSO) δ 11.10 (s, 1H), 10.48 (s, 1H), 8.21 (s, 3H), 8.01 (dt, J = 9.4, 1.9 Hz, 1H), 7.81 (dd, J = 10.6, 4.4 Hz, 1H), 7.70 (dd, J = 13.2, 7.3 Hz, 1H), 7.57 (d, J = 8.9 Hz, 1H), 7.45-7.38 (m, 1H), 7.31 (t, J = 7.6 Hz, 1H). LCMS B rt 3.60 min, m/z 380.1 [M + H]$^+$. |
| 90 | 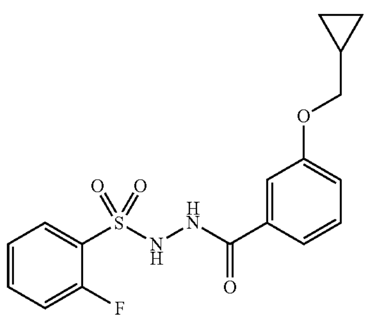 [SMILES: O=C(NNS(=O)(=O)c1ccccc1F)c1cccc(OCC2CC2)c1] | B | E1 | Colourless solid (67% yield). $^1$H NMR (400 MHz, DMSO) δ 10.67 (s, 1H), 10.25 (s, 1H), 7.78 (td, J = 7.7, 1.6 Hz, 1H), 7.72-7.65 (m, 1H), 7.42-7.36 (m, 1H), 7.35-7.27 (m, 2H), 7.22 (dd, J = 11.4, 4.9 Hz, 2H), 7.09 (dd, J = 7.8, 2.1 Hz, 1H), 3.82 (d, J = 7.0 Hz, 2H), 1.29-1.14 (m, 1H), 0.60-0.49 (m, 2H), 0.39-0.24 (m, 2H). LCMS B rt 3.63, m/z 365.1 [M + H]$^+$. |
| 91 | 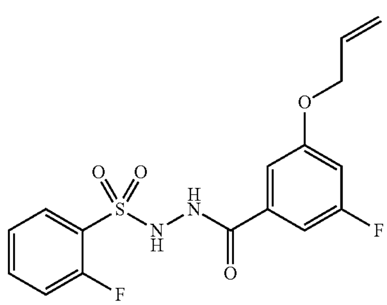 [SMILES: C=CCOc1cc(F)cc(C(=O)NNS(=O)(=O)c2ccccc2F)c1] | B | E7 | Colourless solid (61% yield). $^1$H NMR (400 MHz, DMSO) δ 10.79 (s, 1H), 10.36 (s, 1H), 7.79 (td, J = 7.7, 1.6 Hz, 1H), 7.75-7.63 (m, 1H), 7.47-7.36 (m, 1H), 7.30 (td, J = 7.8, 0.9 Hz, 1H), 7.12 (s, 1H), 7.10-7.00 (m, 2H), 6.02 (ddt, J = 17.2, 10.5, 5.2 Hz, 1H), 5.39 (dd, J = 17.3, 1.7 Hz, 1H), 5.28 (dd, J = 10.5, 1.5 Hz, 1H), 4.61 (d, J = 5.2 Hz, 2H). LCMS B rt 3.64 min, m/z 369.1 [M + H]$^+$. |
| 92 | 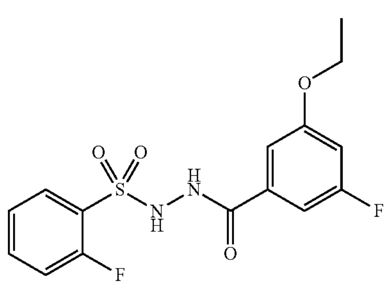 [SMILES: CCOc1cc(F)cc(C(=O)NNS(=O)(=O)c2ccccc2F)c1] | B | E4 | Colourless solid (65% yield). $^1$H NMR (400 MHz, DMSO) δ 10.78 (s, 1H), 10.34 (s, 1H), 7.86-7.61 (m, 2H), 7.40 (t, J = 8.6 Hz, 1H), 7.37-7.22 (m, 1H), 7.18-6.91 (m, 3H), 4.05 (dt, J = 6.7, 4.1 Hz, 2H), 1.32 (td, J = 6.9, 2.8 Hz, 3H). LCMS B rt 3.61 min, m/z 357.1 [M + H]$^+$. |

| | Structure | M | Int | |
|---|---|---|---|---|
| 93 | 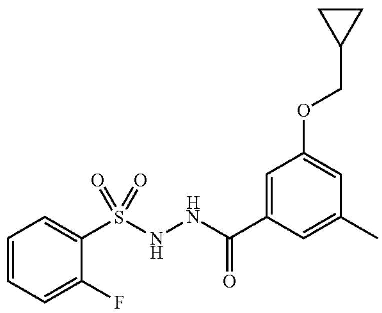 [SMILES: Cc1cc(OCC2CC2)cc(C(=O)NNS(=O)(=O)c2ccccc2F)c1] | B | E3 | Colourless solid (55% yield). $^1$H NMR (400 MHz, DMSO) δ 10.49 (s, 1H), 10.09 (s, 1H), 7.92-7.77 (m, 2H), 7.68-7.61 (m, 1H), 7.55 (t, J = 7.5 Hz, 2H), 6.97 (dd, J = 5.6, 3.1 Hz, 1H), 6.63 (dd, J = 4.7, 3.3 Hz, 1H), 3.76 (d, J = 7.0 Hz, 2H), 3.36 (m, 1H, underneath H$_2$O peak) 2.19 (d, J = 1.7 Hz, 3H), 0.60-0.51 (m, 2H), 0.34-0.26 (m, 2H). LCMS B rt 3.69 min, m/z 379.1 [M + H]$^+$. |
| 94 | 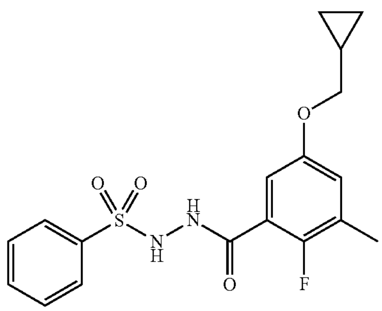 [SMILES: Cc1cc(OCC2CC2)cc(C(=O)NNS(=O)(=O)c2ccccc2)c1F] | B | E9 | Colourless solid (70% yield). $^1$H NMR (400 MHz, DMSO) δ 10.61 (d, J = 2.2 Hz, 1H), 10.23 (d, J = 2.4 Hz, 1H), 7.78 (td, J = 7.6, 1.7 Hz, 1H), 7.73-7.62 (m, 1H), 7.39 (dd, J = 9.7, 8.6 Hz, 1H), 7.32-7.26 (m, 1H), 7.04 (d, J = 18.0 Hz, 2H), 6.91 (s, 1H), 3.80 (d, J = 7.0 Hz, 2H), 3.36 (m, 1H, underneath H$_2$O peak), 2.26 (s, 3H). 0.64-0.46 (m, 2H), 0.37-0.22 (m, 2H). LCMS B rt 3.69 min, m/z 379.1 [M + H]$^+$. |
| 95 | 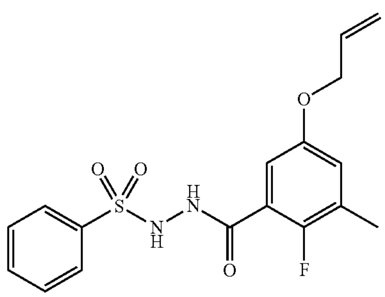 [SMILES: C=CCOc1cc(C)c(F)c(C(=O)NNS(=O)(=O)c2ccccc2)c1] | B | E8 | Colourless solid (62% yield). $^1$H NMR (400 MHz, DMSO) δ 10.50 (s, 1H), 10.10 (s, 1H), 7.88-7.83 (m, 2H), 7.64 (ddd, J = 6.6, 3.8, 1.2 Hz, 1H), 7.55 (dd, J = 10.4, 4.7 Hz, 2H), 7.01 (dd, J = 5.4, 3.2 Hz, 1H), 6.67 (dd, J = 4.7, 3.4 Hz, 1H), 6.01 (ddt, J = 17.2, 10.4, 5.2 Hz, 1H), 5.37 (ddd, J = 17.3, 3.4, 1.6 Hz, 1H), 5.26 (dd, J = 10.5, 1.6 Hz, 1H), 4.53 (dt, J = 5.1, 1.4 Hz, 2H), 2.19 (d, J = 1.8 Hz, 3H). LCMS B rt 3.68 min m/z 365.2 [M + H]$^+$. |
| 96 | 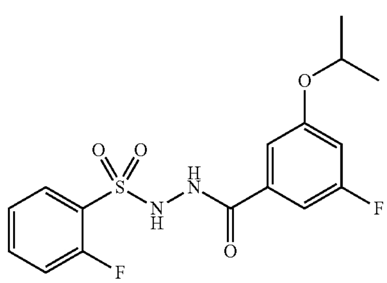 [SMILES: CC(C)Oc1cc(F)cc(C(=O)NNS(=O)(=O)c2ccccc2F)c1] | B | E5 | Colourless solid (63% yield). $^1$H NMR (400 MHz, DMSO) δ 10.77 (s, 1H), 10.33 (s, 1H), 7.78 (t, J = 7.4 Hz, 1H), 7.69 (dd, J = 12.4, 6.6 Hz, 1H), 7.44-7.36 (m, 1H), 7.30 (t, J = 7.6 Hz, 1H), 7.06 (s, 1H), 7.00 (dd, J = 8.8, 6.4 Hz, 2H), 4.66 (dt, J = 12.0, 6.0 Hz, 1H), 1.26 (d, J = 6.0 Hz, 6H). LCMS B rt 3.68 min, m/z 371.2 [M + H]$^+$. |
| 97 | 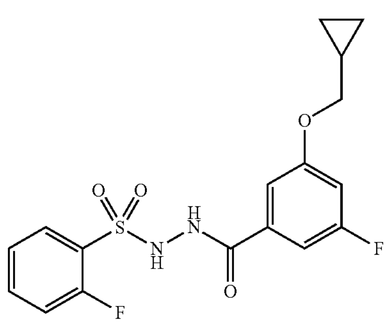 [SMILES: O=C(NNS(=O)(=O)c1ccccc1F)c1cc(F)cc(OCC2CC2)c1] | B | E6 | Colourless solid (72% yield). $^1$H NMR (400 MHz, DMSO) δ 10.77 (s, 1H), 10.35 (s, 1H), 7.79 (dd, J = 10.5, 4.4 Hz, 1H), 7.73-7.66 (m, 1H), 7.45-7.37 (m, 1H), 7.31 (t, J = 7.6 Hz, 1H), 7.10 (s, 1H), 7.02 (dd, J = 9.9, 1.5 Hz, 2H), 3.86 (d, J = 7.1 Hz, 2H), 1.22 (qd, J = 7.7, 3.8 Hz, 1H), 0.62-0.54 (m, 2H), 0.36-0.27 (m, 2H). LCMS B rt 3.69, m/z 383.1 [M + H]$^+$. |

| | Structure | M | Int | |
|---|---|---|---|---|
| 99 | (2-fluorophenyl)sulfonyl hydrazide of 3-(pyridazin-4-yl)benzoic acid | A | I4 | Pale brown solid (62% yield). $^1$H NMR (400 MHz, DMSO): δ 10.90 (s, 1H), 10.40 (s, 1H), 9.67 (dd, J = 2.5, 1.2 Hz, 1H), 9.33 (dd, J = 5.5, 1.2 Hz, 1H), 8.22 (t, J = 1.5, 1.5 Hz, 1H), 8.13-8.09 (m, 1H), 8.05 (dd, J = 5.4, 2.5 Hz, 1H), 7.84-7.78 (m, 2H), 7.75-7.64 (m, 1H), 7.65 (t, J = 7.7, 7.7 Hz, 1H), 7.44-7.37 (m, 1H), 7.30 (td, J = 7.6, 7.6, 1.1 Hz, 1H). LCMS B rt 3.30 min, m/z 373.1 [M + H]$^+$. |
| 100 | phenylsulfonyl hydrazide of 3-(furan-2-yl)-5-fluorobenzoic acid | A | I5 | Off-white solid (34% yield). $^1$H NMR (400 MHz, DMSO): δ 10.88 (d, J = 3.4 Hz, 1H), 10.15 (d, J = 3.3 Hz, 1H), 7.88-7.83 (m, 4H), 7.75-7.70 (m, 1H), 7.67-7.61 (m, 1H), 7.58-7.52 (m, 2H), 7.39-7.34 (m, 1H), 7.13 (dd, J = 3.4, 0.8 Hz, 1H), 6.65 (dd, J = 3.4, 1.8 Hz, 1H). LCMS B rt 3.69 min, m/z 361.1 [M + H]$^+$. |
| 101 | (2-fluorophenyl)sulfonyl hydrazide of 3-(furan-2-yl)-5-fluorobenzoic acid | A | I5 | Off-white solid (25% yield). $^1$H NMR (400 MHz, DMSO): δ 10.92 (s, 1H), 10.41 (s, 1H), 7.89-7.78 (m, 3H), 7.75-7.66 (m, 2H), 7.44-7.35 (m, 2H), 7.31 (td, J = 7.7, 7.6, 1.1 Hz, 1H), 7.14-7.10 (m, 1H), 6.65 (dd, J = 3.5, 1.8 Hz, 1H). LCMS B rt 3.63 min, m/z 379.1 [M + H]$^+$. |
| 102 | phenylsulfonyl hydrazide of 3-(furan-2-yl)-5-methoxybenzoic acid | A | I6 | Off-white solid (24% yield). $^1$H NMR (400 MHz, DMSO) δ 10.77 (d, J = 3.4 Hz, 1H), 10.07 (d, J = 3.3 Hz, 1H), 7.87-7.82 (m, 2H), 7.79 (dd, J = 1.7, 0.7 Hz, 1H), 7.66-7.58 (m, 2H), 7.57-7.52 (m, 2H), 7.38 (dd, J = 2.4, 1.4 Hz, 1H), 7.14 (dd, J = 2.4, 1.4 Hz, 1H), 7.03 (dd, J = 3.4, 0.8 Hz, 1H), 6.62 (dd, J = 3.4, 1.8 Hz, 1H). 3.83 (s, 3H). LCMS B rt 3.61 min, m/z 371.1 [M − H]$^-$. |
| 103 | (2-fluorophenyl)sulfonyl hydrazide of 3-(furan-2-yl)-5-methoxybenzoic acid | A | I6 | Off-white solid (46% yield). $^1$H NMR (400 MHz, DMSO): δ 10.80 (d, J = 2.7 Hz, 1H), 10.33 (d, J = 2.7 Hz, 1H), 7.83-7.77 (m, 2H), 7.73-7.66 (m, 1H), 7.61 (t, J = 1.5, 1.5 Hz, 1H), 7.44-7.37 (m, 2H), 7.30 (td, J = 7.6, 7.6, 1.1 Hz, 1H), 7.16-7.13 (m, 1H), 7.03 (dd, J = 3.4, 0.8 Hz, 1H), 6.62 (dd, J = 3.4, 1.8 Hz, 1H), 3.82 (s, 3H). LCMS B rt 3.61 min, m/z 391.1 [M + H]$^+$. |

| | Structure | M | Int | |
|---|---|---|---|---|
| 104 | (structure) | A | I7 | White solid (35% yield). ¹H NMR (400 MHz, DMSO) δ 10.91 (d, J = 3.4 Hz, 1H), 10.16 (d, J = 3.3 Hz, 1H), 7.96-7.93 (m, 2H), 7.89-7.82 (m, 3H), 7.68-7.62 (m, 1H), 7.60-7.51 (m, 3H), 7.16 (d, J = 3.4 Hz, 1H), 6.65 (dd, J = 3.4, 1.8 Hz, 1H). LCMS B rt 3.71 min, m/z 377.1 [M + H]⁺. |
| 105 | (structure) | B | I7 | White solid (63% yield). ¹H NMR (400 MHz, DMSO) δ 10.95 (d, J = 2.7 Hz, 1H), 10.43 (d, J = 2.6 Hz, 1H), 7.98-7.93 (m, 2H), 7.85-7.78 (m, 2H), 7.74-7.66 (m, 1H), 7.59 (t, J = 1.6 Hz, 1H), 7.46-7.37 (m, 1H), 7.31 (td, J = 7.6, 7.6, 1.1 Hz, 1H), 7.15 (d, J = 3.4 Hz, 1H), 6.65 (dd, J = 3.4, 1.8 Hz, 1H). LCMS B rt 3.38 min, m/z 395.1 [M + H]⁺. |
| 106 | (structure) | B | I8 | White solid (56% yield). ¹H NMR (400 MHz, DMSO): δ 11.09 (s, 1H), 10.25 (s, 1H), 8.78 (dd, J = 5.0, 0.8 Hz, 1H), 8.16 (dd, J = 1.5, 0.9 Hz, 1H), 8.12-8.08 (m, 2H), 7.88-7.84 (m, 2H), 7.68-7.62 (m, 1H), 7.59-7.46 (m, 6H). LCMS B rt 3.61 min, m/z 354.1 [M + H]⁺. |
| 107 | (structure) | B | I8 | White solid (59% yield). ¹H NMR (400 MHz, DMSO): δ 11.13 (s, 1H), 10.53 (s, 1H), 8.78 (dd, J = 5.0, 0.8 Hz, 1H), 8.16 (dd, J = 1.5, 0.9 Hz, 1H), 8.12-8.07 (m, 2H), 7.82 (td, J = 7.6, 7.4, 1.7 Hz, 1H), 7.75-7.68 (m, 1H), 7.57-7.46 (m, 4H), 7.42 (ddd, J = 10.6, 8.3, 1.1 Hz, 1H), 7.32 (td, J = 7.7, 7.6, 1.1 Hz, 1H). LCMS B rt 3.59 min, m/z 372.1 [M + H]⁺. |
| 108 | (structure) | B | I9 | Pale brown solid (43% yield). ¹H NMR (400 MHz, DMSO) δ 10.72 (s, 1H), 10.20 (s, 1H), 9.69 (dd, J = 2.5, 1.2 Hz, 1H), 9.34 (dd, J = 5.5, 1.2 Hz, 1H), 8.08 (dd, J = 5.5, 2.5 Hz, 1H), 7.94 (dd, J = 11.2, 1.7 Hz, 1H), 7.91-7.87 (m, 2H), 7.84 (dd, J = 8.1, 1.7 Hz, 1H), 7.68-7.63 (m, 1H), 7.61-7.54 (m, 3H). LCMS B rt 3.31 min, m/z 373.2 [M + H]⁺. |

-continued

| | Structure | M | Int | |
|---|---|---|---|---|
| 109 | 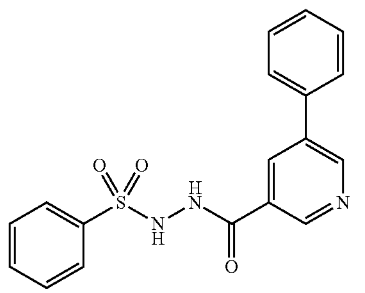 [SMILES: O=C(NNS(=O)(=O)c1ccccc1)c1cncc(-c2ccccc2)c1] | B | I10 | White solid (29% yield). ¹H NMR (400 MHz, DMSO): δ 11.00 (d, J = 3.4 Hz, 1H), 10.22 (d, J = 3.4 Hz, 1H), 9.04 (d, J = 2.3 Hz, 1H), 8.78 (d, J = 2.1 Hz, 1H), 8.31 (t, J = 2.2, 2.2 Hz, 1H), 7.90-7.85 (m, 2H), 7.80-7.75 (m, 2H), 7.67-7.62 (m, 1H), 7.59-7.51 (m, 4H), 7.49-7.44 (m, 1H). LCMS B rt 3.49 min, m/z 354.1 [M + H]⁺. |
| 110 | 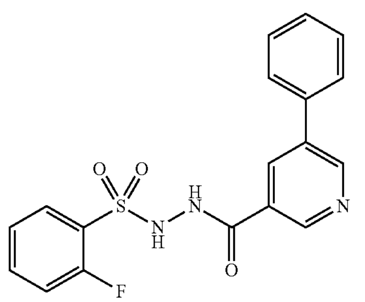 [SMILES: O=C(NNS(=O)(=O)c1ccccc1F)c1cncc(-c2ccccc2)c1] | B | I10 | White solid (60% yield). ¹H NMR (400 MHz, DMSO): δ 11.05 (d, J = 2.8 Hz, 1H), 10.50 (d, J = 2.8 Hz, 1H), 9.05 (d, J = 2.2 Hz, 1H), 8.80 (d, J = 2.1 Hz, 1H), 8.32 (t, J = 2.2, 2.2 Hz, 1H), 7.84 (td, J = 7.5, 7.5, 1.8 Hz, 1H), 7.79-7.76 (m, 2H), 7.74-7.67 (m, 1H), 7.56-7.51 (m, 2H), 7.48-7.40 (m, 2H), 7.32 (td, J = 7.7, 7.7, 1.1 Hz, 1H). LCMS B rt 3.53 min, m/z 372.1 [M + H]⁺. |
| 111 | 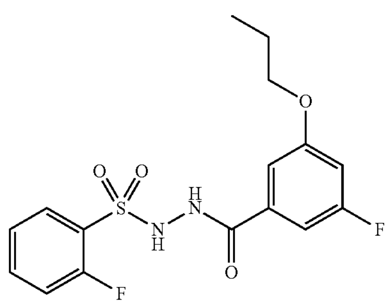 [SMILES: CCCOc1cc(F)cc(C(=O)NNS(=O)(=O)c2ccccc2F)c1] | B | I11 | White solid (59% yield). ¹H NMR (400 MHz, DMSO) δ 10.78 (s, 1H), 10.35 (s, 1H), 7.79 (td, J = 7.6, 7.6, 1.8 Hz, 1H), 7.74-7.65 (m, 1H), 7.40 (ddd, J = 10.6, 8.4, 1.2 Hz, 1H), 7.30 (td, J = 7.6, 7.6, 1.1 Hz, 1H), 7.09 (d, J = 1.5 Hz, 1H), 7.02 (dd, J = 9.8, 1.8 Hz, 2H), 3.95 (t, J = 6.5, 6.5 Hz, 2H), 1.72 (h, J = 7.5, 7.5, 7.5, 7.4, 7.4 Hz, 2H), 0.96 (t, J = 7.4, 7.4 Hz, 3H). LCMS B rt 3.68 min, m/z 371.1 [M + H]⁺. |
| 112 | 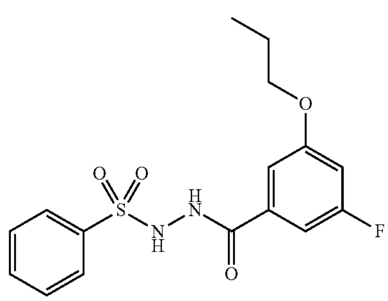 [SMILES: CCCOc1cc(F)cc(C(=O)NNS(=O)(=O)c2ccccc2)c1] | B | I11 | White solid (53% yield). ¹H NMR (400 MHz, DMSO) δ 10.74 (s, 1H), 10.08 (s, 1H), 7.84-7.80 (m, 2H), 7.67-7.61 (m, 1H), 7.58-7.51 (m, 2H), 7.11-7.08 (m, 1H), 7.01 (dd, J = 10.2, 2.0 Hz, 2H), 3.96 (t, J = 6.5, 6.5 Hz, 2H), 1.72 (h, J = 7.3, 7.3, 7.2, 7.2, 7.2 Hz, 2H), 0.97 (t, J = 7.4, 7.4 Hz, 3H). LCMS B rt 3.69 min, m/z 353.1 [M + H]⁺. |
| 113 | 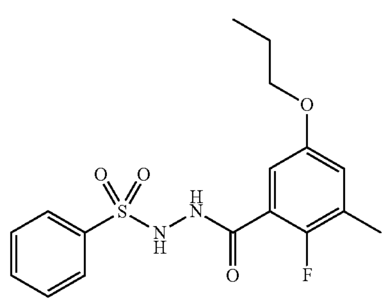 [SMILES: CCCOc1cc(C)c(F)c(C(=O)NNS(=O)(=O)c2ccccc2)c1] | B | I12 | White solid (55% yield). ¹H NMR (400 MHz, DMSO) δ 10.52 (s, 1H), 10.11 (s, 1H), 7.89-7.84 (m, 2H), 7.69-7.62 (m, 1H), 7.60-7.53 (m, 2H), 7.03-6.96 (m, 1H), 6.64 (dd, J = 5.0, 3.1 Hz, 1H), 3.88 (t, J = 6.5, 6.5 Hz, 2H), 1.70 (h, J = 7.4, 7.4, 7.3, 7.3, 7.3 Hz, 2H), 0.96 (t, J = 7.4 Hz, 3H). LCMS A rt 6.6 min, m/z 367.1 [M + H]⁺. |

| | Structure | M | Int | |
|---|---|---|---|---|
| 114 | 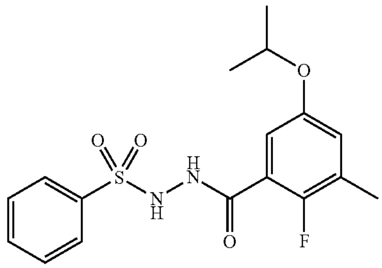 [SMILES: Cc1cc(OC(C)C)cc(C(=O)NNS(=O)(=O)c2ccccc2)c1F] | B | I13 | White solid (56% yield). $^1$H NMR (400 MHz, DMSO) δ 10.51 (d, J = 3.3 Hz, 1H), 10.10 (d, J = 3.3 Hz, 1H), 7.88-7.84 (m, 2H), 7.67-7.61 (m, 1H), 7.56 (dd, J = 8.3, 6.8 Hz, 2H), 6.96 (dd, J = 5.7, 3.1 Hz, 1H), 6.60 (dd, J = 5.0, 3.1 Hz, 1H), 4.51 (hept, J = 6.0 Hz, 1H), 2.18 (d, J = 2.1 Hz, 3H), 1.23 (d, J = 6.0 Hz, 6H). LCMS A rt 6.57 min, m/z 367.1 [M + H]$^+$. |
| 150 | 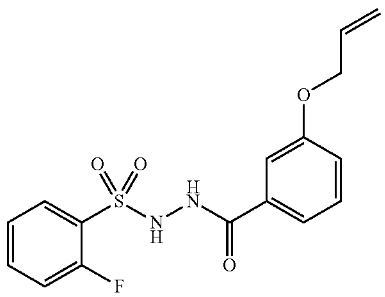 [SMILES: C=CCOc1cccc(C(=O)NNS(=O)(=O)c2ccccc2F)c1] | A | A14 | Colourless solid (51% yield). $^1$H NMR (400 MHz, DMSO) δ 10.68 (s, 1H), 10.26 (s, 1H), 7.79 (td, J = 7.7, 1.7 Hz, 1H), 7.69 (ddd, J = 7.3, 5.0, 1.7 Hz, 1H), 7.46-7.16 (m, 5H), 7.12 (dd, J = 8.2, 1.7 Hz, 1H), 6.04 (ddt, J = 17.2, 10.5, 5.2 Hz, 1H), 5.42-5.36 (m, 1H), 5.27 (ddd, J = 10.5, 3.0, 1.4 Hz, 1H), 4.59 (dt, J = 5.2, 1.5 Hz, 2H). LCMS B rt 3.57 min, m/z 351.1 [M + H]$^+$. |
| 151 | 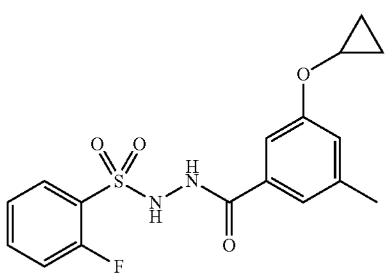 [SMILES: Cc1cc(OC2CC2)cc(C(=O)NNS(=O)(=O)c2ccccc2F)c1] | B | A15 | Colourless solid (38% yield). $^1$H NMR (400 MHz, DMSO) δ 10.61 (s, 1H), 10.21 (s, 1H), 7.79 (t, J = 7.4 Hz, 1H), 7.68 (d, J = 5.0 Hz, 1H), 7.45-7.35 (m, 1H), 7.30 (t, J = 7.7 Hz, 1H), 7.12 (d, J = 15.8 Hz, 2H), 7.02 (s, 1H), 4.38 (d, J = 3.5 Hz, 1H), 2.29 (s, 3H), 0.78 (d, J = 6.1 Hz, 2H), 0.63 (s, 2H). LCMS B rt 3.66 min, m/z 365.1 [M + H]$^+$. |
| 154 | 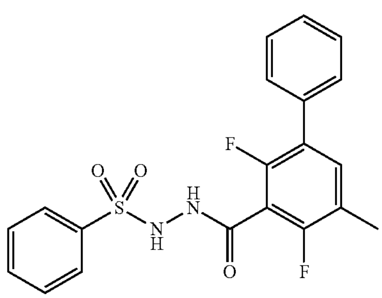 [SMILES: Cc1cc(-c2ccccc2)c(F)c(C(=O)NNS(=O)(=O)c2ccccc2)c1F] | A | I17 | Colourless solid (54% yield). $^1$H NMR (400 MHz, DMSO) δ 10.84 (s, 1H), 10.36 (s, 1H), 7.94-7.80 (m, 2H), 7.66 (t, J = 7.4 Hz, 1H), 7.61-7.46 (m, 7H), 7.43 (dd, J = 8.9, 4.6 Hz, 1H), 2.25 (d, J = 7.0 Hz, 3H). LCMS B rt 3.41 min, m/z 402.8 [M + H]$^+$. |
| 155 | 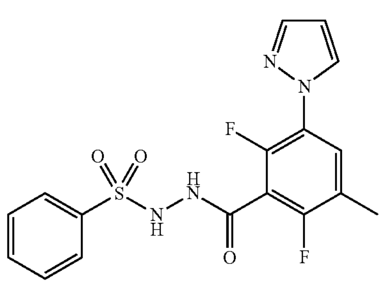 [SMILES: Cc1cc(-n2cccn2)c(F)c(C(=O)NNS(=O)(=O)c2ccccc2)c1F] | A | I19 | Colourless solid (47% yield). $^1$H NMR (400 MHz, DMSO) δ 10.89 (s, 1H), 10.39 (s, 1H), 8.14 (t, J = 2.5 Hz, 1H), 7.95-7.85 (m, 2H), 7.82-7.77 (m, 2H), 7.66 (d, J = 7.5 Hz, 1H), 7.59 (t, J = 7.6 Hz, 2H), 6.59-6.56 (m, 1H), 2.27 (s, 3H). LCMS B rt 3.20 min, m/z 393.4 [M + H]$^+$. |

|  | Structure | M | Int | |
|---|---|---|---|---|
| 156 | 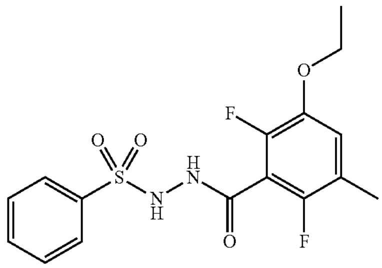 [SMILES: CCOc1cc(C)c(F)c(C(=O)NNS(=O)(=O)c2ccccc2)c1F] | A | I23 | Colourless solid (61% yield). $^1$H NMR (400 MHz, DMSO) δ 10.75 (s, 1H), 10.30 (s, 1H), 7.88-7.81 (m, 2H), 7.70-7.63 (m, 1H), 7.58 (d, J = 7.8 Hz, 2H), 7.23-7.12 (m, 1H), 4.07 (q, J = 7.0 Hz, 2H), 2.18 (s, 3H), 1.32 (t, J = 7.0 Hz, 3H). LCMS B rt 3.27 min, m/z 371.4 [M + H]$^+$. |
| 157 | 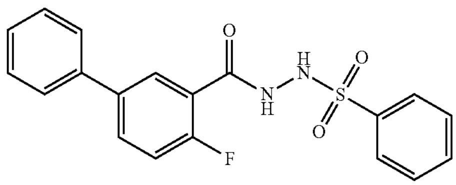 [SMILES: O=C(NNS(=O)(=O)c1ccccc1)c1cc(-c2ccccc2)ccc1F] | A | I24 | Colourless solid (5.5 mg, 3% yield). $^1$H NMR (400 MHz, DMSO) δ 10.69 (s, 1H), 10.18 (s, 1H), 7.89 (d, J = 7.4 Hz, 2H), 7.81 (s, 1H), 7.71-7.53 (m, 6H), 7.49 (t, J = 7.3 Hz, 2H), 7.44-7.26 (m, 2H). LCMS A rt 6.31 min, m/z 371.1 [M + H]$^+$. |

Example 4

The following compound was synthesised according to the specified Amide coupling (M) from commercially available starting materials:

|  | Structure | M | Product details |
|---|---|---|---|
| 98 | 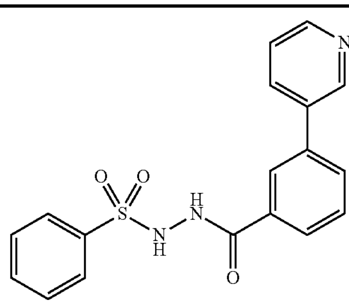 | C | Colourless solid (11% yield). $^1$H NMR (400 MHz, DMSO) δ 10.85 (s, 1H), 10.12 (s, 1H), 8.95 (s, 1H), 8.61 (s, 1H), 8.29-7.98 (m, 2H), 7.89 (dd, J = 22.7, 6.5 Hz, 3H), 7.74-7.44 (m, 6H). LCMS B rt 4.67, m/z 354.1 [M + H]$^+$. |
| 115 | 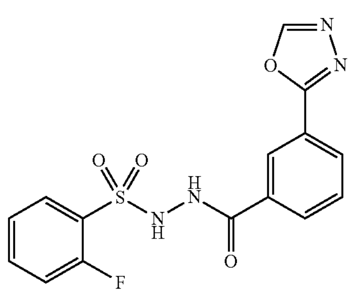 [SMILES: O=C(NNS(=O)(=O)c1ccccc1F)c1cccc(-c2nnco2)c1] | B | White solid (25% yield). $^1$H NMR (400 MHz, DMSO) δ 11.03 (s, 1H), 10.41 (s, 1H), 9.40 (s, 1H), 8.34 (t, J = 1.7, 1.7 Hz, 1H), 8.21-8.15 (m, 1H), 7.96-7.91 (m, 1H), 7.81 (td, J = 7.5, 7.5, 1.8 Hz, 1H), 7.73-7.66 (m, 2H), 7.48-7.37 (m, 1H), 7.30 (td, J = 7.6, 7.6, 1.1 Hz, 1H). LCMS B rt 3.35 min, m/z 363.1 [M + H]$^+$. |
| 116 | 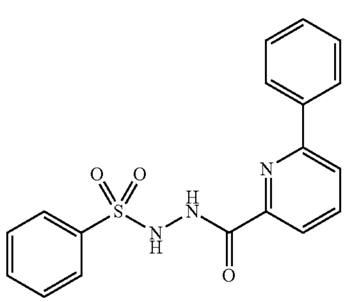 [SMILES: O=C(NNS(=O)(=O)c1ccccc1)c1cccc(-c2ccccc2)n1] | B | White solid (68% yield). $^1$H NMR (400 MHz, DMSO) δ 10.76 (d, J = 3.1 Hz, 1H), 10.11 (d, J = 3.1 Hz, 1H), 8.31 (dd, J = 8.0, 1.6 Hz, 2H). 8.20-8.16 (m, 1H), 8.01 (t, J = 7.8, 7.8 Hz, 1H), 7.89-7.86 (m, 2H), 7.76 (dd, J = 7.7, 0.8 Hz, 1H), 7.69-7.63 (m, 1H), 7.59-7.48 (m, 5H). LCMS B rt 3.68 min, m/z 354.1 [M + H]$^+$. |

| | Structure | M | Product details |
|---|---|---|---|
| 117 | 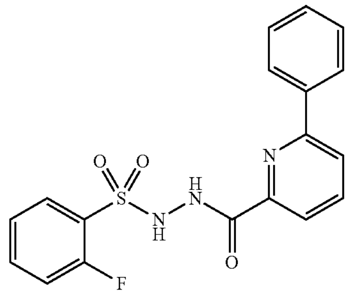 [SMILES: O=C(NNS(=O)(=O)c1ccccc1F)c1cccc(-c2ccccc2)n1] | B | White solid (70% yield). ¹H NMR (400 MHz, DMSO) δ 10.92 (d, J = 3.1 Hz, 1H), 10.37 (d, J = 2.9 Hz, 1H), 8.34 (d, J = 7.2 Hz, 2H), 8.18 (d, J = 7.9 Hz, 1H), 8.01 (t, J = 7.7, 7.7 Hz, 1H), 7.86-7.74 (m, 2H), 7.70 (dd, J = 11.9, 6.0 Hz, 1H), 7.57-7.38 (m, 4H), 7.29 (t, J = 7.6, 7.6 Hz, 1H). LCMS B rt 3.69 min, m/z 372.1 [M + H]⁺. |
| 118 | 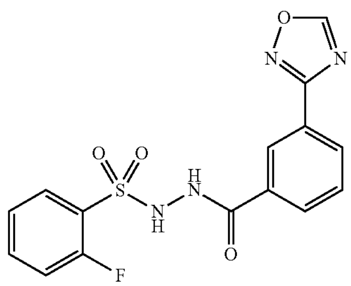 [SMILES: O=C(NNS(=O)(=O)c1ccccc1F)c1cccc(-c2ncon2)c1] | B | Colourless solid (56% yield). ¹H NMR (400 MHz, DMSO) δ ¹H NMR (400 MHz, DMSO) 5 11.00 (s, 1H), 10.39 (s, 1H), 9.77 (s, 1H), 8.36 (d, J = 1.5 Hz, 1H), 8.21 (d, J = 7.9 Hz, 1H), 7.92 (dd, J = 6.6, 1.5 Hz, 1H), 7.82 (td, J = 7.6, 1.6 Hz, 1H), 7.68 (dd, J = 9.1, 6.5 Hz, 2H), 7.49-7.38 (m, 1H), 7.30 (dd, J = 7.6, 1.0 Hz, 1H). LCMS B rt 3.11 min, m/z 363.1 [M + H]⁺. |
| 119 | 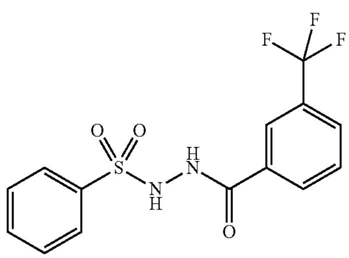 [SMILES: O=C(NNS(=O)(=O)c1ccccc1)c1cccc(C(F)(F)F)c1] | B | White solid (0.059 g, 33% yield). ¹H NMR (400 MHz, DMSO-d₆) δ 10.96 (d, J = 2.1 Hz, 1H), 10.16 (d, J = 2.7 Hz, 1H), 8.04-7.96 (m, 2H), 7.93 (d, J = 7.5 Hz, 1H), 7.85 (d, J = 7.5 Hz, 2H), 7.71 (t, J = 7.7 Hz, 1H), 7.64 (t, J = 7.2 Hz, 1H), 7.54 (t, J = 7.5 Hz, 2H). LCMS A rt 6.77 min, m/z 344.1 [M + H]⁺. |
| 120 | 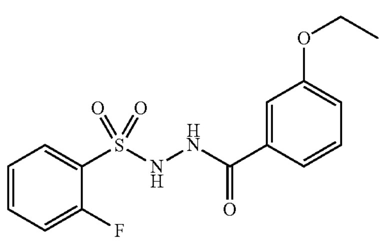 [SMILES: CCOc1cccc(C(=O)NNS(=O)(=O)c2ccccc2F)c1] | B | White solid (0.104 g, 34% yield). ¹H NMR (400 MHz, DMSO-d₆) δ 10.27 (s, 1H), 7.79 (td, J = 7.7, 1.5 Hz, 2H), 7.72-7.64 (m, 1H), 7.43-7.22 (m, 3H), 7.20 (s, 1H), 7.08 (dd, J = 8.1, 1.8 Hz, 1H), 4.03 (q, J = 6.9 Hz, 2H), 1.32 (t, J = 7.0 Hz, 3H). LCMS A rt 6.00 min, m/z 337.0 [M − H]⁻. |
| 121 | 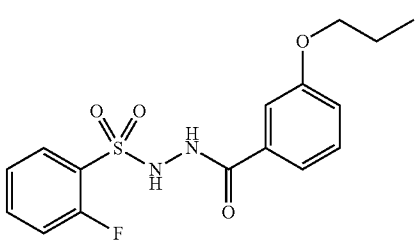 [SMILES: CCCOc1cccc(C(=O)NNS(=O)(=O)c2ccccc2F)c1] | B | White solid (0.101 g, 52% yield). ¹H NMR (400 MHz, DMSO-d₆) δ 10.68 (s, 1H), 10.25 (s, 1H), 7.79 (td, J = 7.7, 1.7 Hz, 1H), 7.69 (ddd, J = 8.3, 5.0, 1.7 Hz, 1H), 7.44-7.20 (m, 5H), 7.10 (dd, J = 8.2, 1.7 Hz, 1H), 3.94 (t, J = 6.5 Hz, 2H), 1.79-1.50 (m, 2H), 0.98 (t, J = 7.4 Hz, 3H). LCMS B rt 3.41 min, m/z 353.2 [M + H]⁺. |
| 122 | 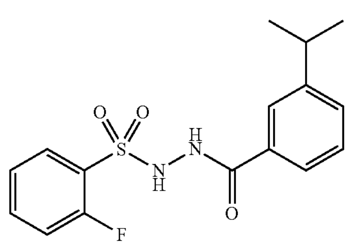 [SMILES: CC(C)c1cccc(C(=O)NNS(=O)(=O)c2ccccc2F)c1] | B | White solid (0.105 g, 51% yield). ¹H NMR (400 MHz, DMSO-d₆) δ 10.68 (s, 1H), 10.24 (s, 1H), 7.8 (td, J = 7.6, 1.7 Hz, 1H), 7.73-7.65 (m, 1H), 7.57 (s, 1H), 7.48 (d, J = 7.6 Hz, 1H), 7.45-7.32 (m, 3H), 7.30 (td, J = 7.7, 1.0 Hz, 1H), 2.9 (m, 1H), 1.21 (s, 3H), 1.19 (s, 3H). LCMS B rt 3.41, m/z 337.1 [M + H]⁺. |

-continued

| | Structure | M | Product details |
|---|---|---|---|
| 123 | 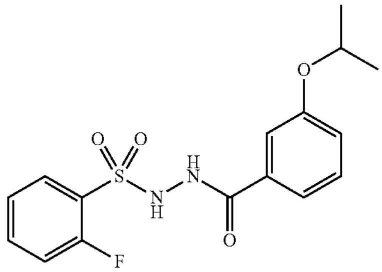 [SMILES: CC(C)Oc1cccc(C(=O)NNS(=O)(=O)c2ccccc2F)c1] | B | White solid (0.191 g, 99% yield). $^1$H NMR (400 MHz, DMSO-d$_6$) δ 10.69 (s, 1H), 10.27 (s, 1H), 7.79 (t, J = 6.9 Hz, 1H), 7.68 (d, J = 4.6 Hz, 1H), 7.44-7.35 (m, 1H), 7.31 (dt, J = 10.8, 7.8 Hz, 2H), 7.25-7.15 (m, 2H), 7.07 (d, J = 7.5 Hz, 1H), 4.77-4.50 (m, 1H), 1.25 (d, J = 5.8 Hz, 6H). LCMS A rt 6.87 min, m/z 353.1 [M + H]$^+$. |
| 124 | 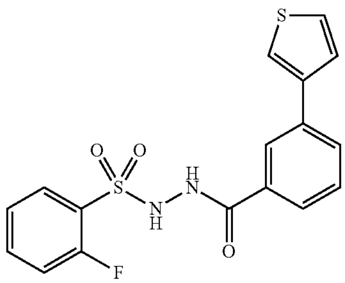 [SMILES: O=C(NNS(=O)(=O)c1ccccc1F)c1cccc(-c2ccsc2)c1] | B | White solid (0.191 g, 99% yield). $^1$H NMR (400 MHz, DMSO-d$_6$) δ 10.82 (s, 1H), 10.35 (s, 1H), 8.03 (s, 1H), 7.93 (d, J = 1.6 Hz, 1H), 7.89 (d, J = 7.7 Hz, 1H), 7.81 (t, J = 6.8 Hz, 1H), 7.73-7.65 (m, 2H), 7.58 (d, J = 6.2 Hz, 2H), 7.48 (t, J = 7.7 Hz, 1H), 7.44-7.37 (m, 1H), 7.30 (t, J = 7.6 Hz, 1H). LCMS A rt 6.90 min, m/z 377.1 [M + H]$^+$. |
| 125 | 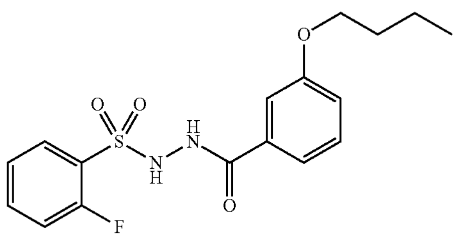 [SMILES: CCCCOc1cccc(C(=O)NNS(=O)(=O)c2ccccc2F)c1] | B | White solid (0.129 g, 70% yield). $^1$H NMR (400 MHz, DMSO-d$_6$) δ 10.70 (d, J = 2.3 Hz, 1H), 10.27 (d, J = 2.5 Hz, 1H), 7.82-7.75 (m, 1H), 7.72-7.64 (m, 1H), 7.44-7.19 (m, 5H), 7.09 (dd, J = 8.1, 1.7 Hz, 1H), 3.97 (t, J = 6.5 Hz, 2H), 1.75-1.62 (m, 2H), 1.42 (dd, J = 14.9, 7.4 Hz, 2H), 0.93 (t, J = 7.4 Hz, 3H). LCMS A rt 7.45 min, m/z 367.1 [M + H]$^+$. |
| 126 | 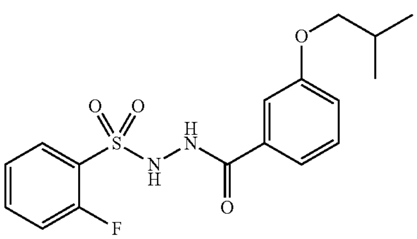 [SMILES: CC(C)COc1cccc(C(=O)NNS(=O)(=O)c2ccccc2F)c1] | B | White solid (0.145 g, 78% yield). $^1$H NMR (400 MHz, DMSO-d$_6$) δ 10.70 (s, 1H), 10.28 (s, 1H), 7.79 (td, J = 7.7, 1.6 Hz, 1H), 7.68 (ddd, J = 8.1, 5.0, 1.7 Hz, 1H), 7.44-7.21 (m, 5H), 7.09 (dd, J = 8.1, 1.7 Hz, 1H), 3.74 (d, J = 6.5 Hz, 2H), 2.00 (dt, J = 13.3, 6.6 Hz, 1H), 0.97 (d, J = 6.7 Hz, 6H). LCMS B rt 3.74, m/z 367.2 [M + H]$^+$. |
| 127 | 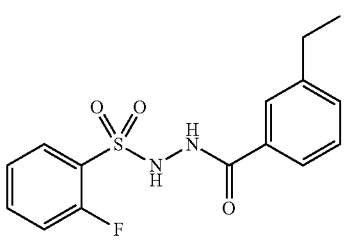 [SMILES: CCc1cccc(C(=O)NNS(=O)(=O)c2ccccc2F)c1] | B | White solid (0.081 g, 38% yield). $^1$H NMR (400 MHz, DMSO-D6) δ 10.67 (s, 1H), 10.24 (s, 1H), 7.79 (t, J = 7.5 Hz, 1H), 7.68 (dd, J = 12.5, 6.5 Hz, 1H), 7.53 (s, 1H), 7.49 (d, J = 7.4 Hz, 1H), 7.43-7.24 (m, 4H), 2.61 (q, J = 7.6 Hz, 2H), 1.17 (t, J = 7.6 Hz, 3H). LCMS A rt 6.90 min, m/z 323.1 [M + H]$^+$. |
| 128 | 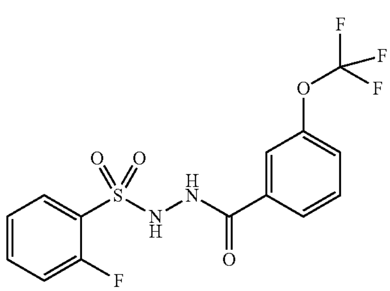 [SMILES: O=C(NNS(=O)(=O)c1ccccc1F)c1cccc(OC(F)(F)F)c1] | B | White solid (0.218 g, 79% yield). $^1$H NMR (400 MHz, DMSO) δ 10.94 (d, J = 2.4 Hz, 1H), 10.40 (d, J = 2.5 Hz, 1H), 7.80 (td, J = 7.7, 1.7 Hz, 1H), 7.76-7.66 (m, 2H), 7.65-7.56 (m, 3H), 7.45-7.38 (m, 1H), 7.31 (td, J = 7.7, 1.0 Hz, 1H). LCMS B rt 3.73 min, m/z 379.2 [M + H]$^+$. |

|   | Structure | M | Product details |
|---|---|---|---|
| 129 | 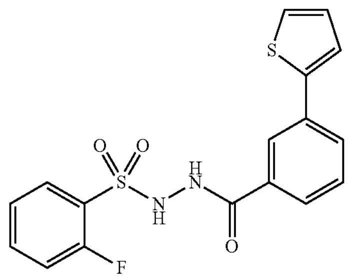 [SMILES: O=C(NNS(=O)(=O)c1ccccc1F)c1cccc(-c2cccs2)c1] | B | White solid (0.122 g, 65% yield). ¹H NMR (400 MHz, DMSO) δ 10.86 (s, 1H), 10.34 (s, 1H), 7.95 (s, 1H), 7.82 (dd, J = 12.9, 7.0 Hz, 2H), 7.70 (dd, J = 12.4, 6.7 Hz, 1H), 7.64-7.56 (m, 3H), 7.49 (t, J = 7.7 Hz, 1H), 7.45-7.38 (m, 1H), 7.31 (t, J = 7.6 Hz, 1H), 7.18 (dd, J = 5.0, 3.7 Hz, 1H). LCMS B rt 3.59, m/z 377.1 [M + H]⁺. |
| 130 | 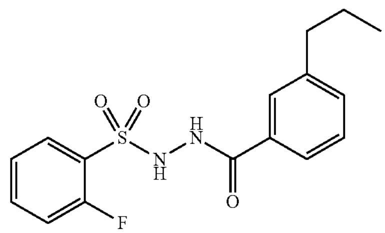 [SMILES: CCCc1cccc(C(=O)NNS(=O)(=O)c2ccccc2F)c1] | B | White solid (0.058 g, 48% yield). ¹H NMR (400 MHz, DMSO) δ 10.66 (s, 1H), 10.25 (s, 1H), 7.80 (td, J = 7.7, 1.7 Hz, 1H), 7.72-7.65 (m, 1H), 7.53-7.47 (m, 2H), 7.43-7.33 (m, 3H), 7.29 (td, J = 7.7, 1.0 Hz, 1H), 2.57 (t, J = 7.6, 2H), 1.70-1.48 (m, 2H), 0.88 (t, J = 7.3 Hz, 3H). LCMS B rt 3.66 min, m/z 337.2 [M + H]⁺. |
| 131 | 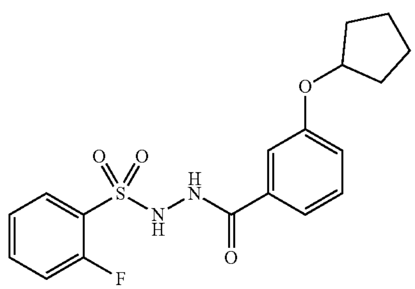 [SMILES: O=C(NNS(=O)(=O)c1ccccc1F)c1cccc(OC2CCCC2)c1] | B | White solid (0.127 g, 69% yield). ¹H NMR (400 MHz, DMSO) δ 10.64 (s, 1H), 10.26 (s, 1H), 7.79 (t, J = 6.7 Hz, 1H), 7.72-7.65 (m, 1H), 7.43-7.36 (m, 1H), 7.31 (dt, J = 10.3, 7.7 Hz, 2H), 7.22 (d, J = 7.8 Hz, 1H), 7.17 (s, 1H), 7.07 (d, J = 8.2 Hz, 1H), 4.92-4.74 (m, 1H), 1.98-1.86 (m, 2H), 1.76-1.64 (m, 4H), 1.63-1.53 (m, 2H). LCMS B rt 3.37 min, m/z 379.2 [M + H]⁺. |
| 132 | 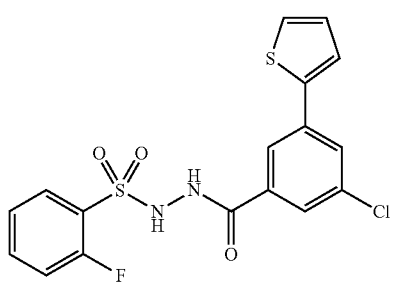 [SMILES: O=C(NNS(=O)(=O)c1ccccc1F)c1cc(Cl)cc(-c2cccs2)c1] | B | White solid (0.04 g, 94% yield). ¹H NMR (400 MHz, DMSO) δ 7.93 (s, 1H), 7.87 (s, 1H), 7.81 (t, J = 6.7 Hz, 1H), 7.73-7.64 (m, 3H), 7.59 (s, 1H), 7.45-7.37 (m, 1H), 7.31 (t, J = 7.6 Hz, 1H), 7.18 (dd, J = 5.0, 3.7 Hz, 1H). LCMS B rt 3.76 min, m/z 411.1 [M + H]⁺. |
| 133 | 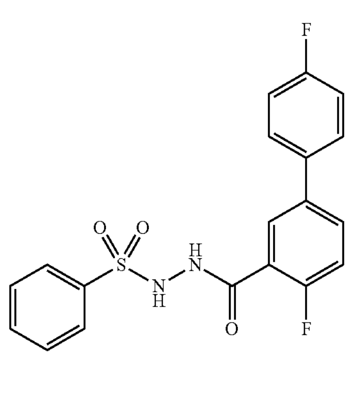 [SMILES: O=C(NNS(=O)(=O)c1ccccc1)c1cc(-c2ccc(F)cc2)ccc1F] | B | White solid (0.198 g, 60% yield). LCMS A rt 6.38 min, m/z 389.0 [M + H]⁺. |

| | Structure | M | Product details |
|---|---|---|---|
| 134 | (structure) | B | White solid (0.108 g, 81% yield). ¹H NMR (400 MHz, DMSO) δ 10.55 (d, J = 3.3 Hz, 1H), 10.11 (d, J = 3.4 Hz, 1H), 7.90-7.82 (m, 2H), 7.70-7.61 (m, 1H), 7.56 (t, J = 7.5 Hz, 2H), 7.16 (t, J = 9.3 Hz, 1H), 7.08-7.01 (m, 1H), 6.80 (dd, J = 5.5, 3.1 Hz, 1H), 4.64-4.42 (m, 1H), 1.24 (d, J = 6.0 Hz, 6H). LCMS B rt 3.61 min, m/z 353.1 [M + H]⁺. |
| 135 | (structure) | B | White solid (0.111 g, 91% yield). ¹H NMR (400 MHz, DMSO) δ 10.86 (s, 1H), 10.34 (s, 1H), 7.95 (s, 1H), 7.82 (dd, J = 12.9, 7.0 Hz, 2H), 7.70 (dd, J = 12.4, 6.7 Hz, 1H), 7.64-7.56 (m, 3H), 7.49 (t, J = 7.7 Hz, 1H), 7.45-7.38 (m, 1H), 7.31 (t, J = 7.6 Hz, 1H), 7.18 (dd, J = 5.0, 3.7 Hz, 1H). LCMS B rt 3.61 min, m/z 361.1 [M + H]⁺. |
| 136 | (structure) | B | White solid (0.111 g, 61% yield). ¹H NMR (400 MHz, DMSO) δ 10.55 (s, 1H), 10.12 (s, 1H), 7.86 (d, J = 7.3 Hz, 2H), 7.65 (t, J = 7.3 Hz, 1H), 7.56 (t, J = 7.5 Hz, 2H), 7.19 (t, J = 9.3 Hz, 1H), 7.13-7.04 (m, 1H), 6.86 (dd, J = 5.3, 3.2 Hz, 1H), 6.02 (ddd, J = 22.4, 10.4, 5.2 Hz, 1H), 5.38 (dd, J = 17.3, 1.6 Hz, 1H), 5.27 (d, J = 10.6 Hz, 1H), 4.56 (d, J = 5.1 Hz, 2H). LCMS B rt 3.57 min, m/z 351.1 [M + H]⁺. |
| 137 | (structure) | B | White solid (0.072 g, 73% yield). ¹H NMR (400 MHz, DMSO) δ 10.62 (s, 1H), 10.23 (s, 1H), 7.78 (td, J = 7.7, 1.5 Hz, 1H), 7.68 (ddd, J = 8.1, 5.0, 1.7 Hz, 1H), 7.43-7.35 (m, 1H), 7.32-7.26 (m, 1H), 7.07 (s, 1H), 7.02 (s, 1H), 6.91 (s, 1H), 4.01 (q, J = 6.9 Hz, 2H), 2.27 (s, 3H), 1.30 (t, J = 7.0 Hz, 3H). LCMS A rt 6.19 min, m/z 353.1 [M + H]⁺. |
| 138 | (structure) | B | White solid (0.078 g, 88% yield). ¹H NMR (400 MHz, DMSO) δ 10.51 (s, 1H), 10.10 (s, 1H), 7.86 (d, J = 7.5 Hz, 2H), 7.64 (t, J = 7.3 Hz, 1H), 7.56 (t, J = 7.5 Hz, 2H), 6.97 (dd, J = 5.3, 2.9 Hz, 1H), 6.78-6.48 (m, 1H), 3.98 (q, J = 6.9 Hz, 2H), 2.19 (s, 3H), 1.30 (t, J = 6.9 Hz, 3H). LCMS A rt 6.22 min, m/z 353.1 [M + H]⁺. |
| 139 | (structure) | B | White solid (0.085 g, 35% yield). ¹H NMR (400 MHz, DMSO) δ 10.62 (s, 1H), 10.23 (s, 1H), 7.78 (dd, J = 10.6, 4.3 Hz, 1H), 7.69 (dd, J = 12.3, 6.7 Hz, 1H), 7.44-7.36 (m, 1H), 7.30 (t, J = 7.6 Hz, 1H), 7.05 (s, 1H), 7.01 (s, 1H), 6.90 (s, 1H), 4.68-4.49 (m, 1H), 2.27 (s, 3H), 1.25 (d, J = 6.0 Hz, 6H). LCMS A rt 6.35 min, m/z 367.2 [M + H]⁺. |

|  | Structure | M | Product details |
| --- | --- | --- | --- |
| 140 | 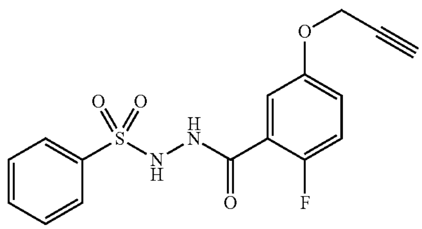 [SMILES: C#CCOc1ccc(F)c(C(=O)NNS(=O)(=O)c2ccccc2)c1] | B | White solid (0.069 g, 77% yield). $^1$H NMR (400 MHz, MeOD) δ 8.00-7.94 (m, 2H), 7.68-7.60 (m, 1H), 7.59-7.51 (m, 2H), 7.12 (dd, J = 6.0, 2.1 Hz, 2H), 7.06-7.01 (m, 1H), 4.72 (d, J = 2.4 Hz, 3H), 2.99 (t, J = 2.4 Hz, 1H). LCMS B rt 3.51 min, m/z 349.1 [M + H]$^+$. |
| 141 | 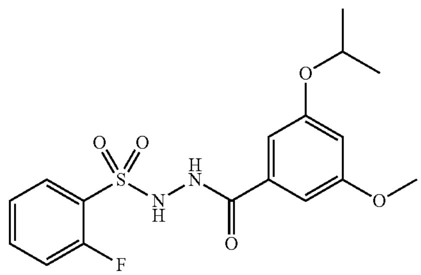 [SMILES: COc1cc(OC(C)C)cc(C(=O)NNS(=O)(=O)c2ccccc2F)c1] | B | White solid (0.102 g, 75% yield). $^1$H NMR (400 MHz, DMSO) δ 10.63 (s, 1H), 10.24 (s, 1H), 7.78 (t, J = 6.8 Hz, 1H), 7.68 (dd, J = 12.3, 6.5 Hz, 1H), 7.44-7.35 (m, 2H), 7.30 (t, J = 7.6 Hz, 1H), 6.79 (s, 1H), 6.61 (s, 1H), 4.60 (dt, J = 12.0, 6.0 Hz, 1H), 3.73 (s, 3H), 1.24 (d, J = 6.0 Hz, 6H). LCMS B rt 3.62 min, m/z 383.1 [M + H]$^+$. |
| 142 | 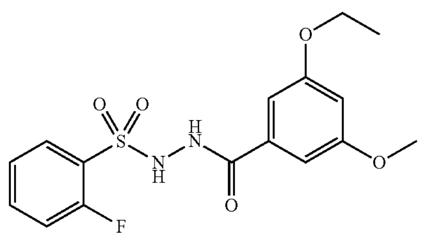 [SMILES: CCOc1cc(OC)cc(C(=O)NNS(=O)(=O)c2ccccc2F)c1] | B | White solid (0.093 g, 65% yield). $^1$H NMR (400 MHz, DMSO) δ 7.82-7.75 (m, 1H), 7.72-7.64 (m, 1H), 7.39 (dd, J = 9.9, 8.8 Hz, 1H), 7.29 (td, J = 7.7, 1.0 Hz, 1H), 6.80 (d, J = 2.3 Hz, 1H), 6.63 (t, J = 2.2 Hz, 1H), 4.01 (q, J = 7.0 Hz, 2H), 3.74 (s, 3H), 1.30 (t, J = 7.0 Hz, 3H). LCMS B rt 3.57 min, m/z 369.1 [M + H]$^+$. |
| 143 | 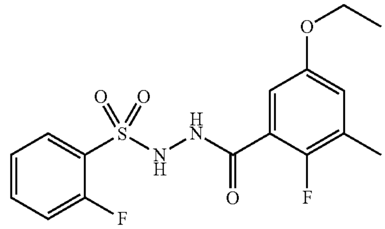 [SMILES: CCOc1cc(C)c(F)c(C(=O)NNS(=O)(=O)c2ccccc2F)c1] | B | White solid (0.025 g, 29% yield). $^1$H NMR (400 MHz, DMSO) δ 7.82-7.75 (m, 1H), 7.72-7.64 (m, 1H), 7.39 (dd, J = 9.9, 8.8 Hz, 1H), 7.29 (td, J = 7.7, 1.0 Hz, 1H), 6.80 (d, J = 2.3 Hz, 1H), 6.63 (t, J = 2.2 Hz, 1H), 4.01 (q, J = 7.0 Hz, 2H), 3.74 (s, 3H), 1.30 (t, J = 7.0 Hz, 3H). LCMS B rt 3.62 min, m/z 371.1 [M + H]$^+$. |
| 144 | 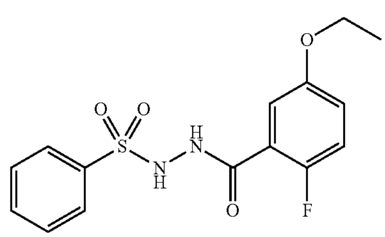 [SMILES: CCOc1ccc(F)c(C(=O)NNS(=O)(=O)c2ccccc2)c1] | B | White solid (0.069 g, 75% yield). $^1$H NMR (400 MHz, Acetone) δ 8.04-7.88 (m, 2H), 7.65 (dd, J = 10.5, 4.3 Hz, 1H), 7.56 (dd, J = 10.4, 4.7 Hz, 2H), 7.10 (ddd, J = 14.0, 13.1, 6.6 Hz, 2H), 7.01 (dd, J = 5.5, 3.1 Hz, 1H), 4.03 (q, J = 7.0 Hz, 2H), 1.34 (t, J = 7.0 Hz, 3H). LCMS A rt 6.03 min, m/z 339.1 [M + H]$^+$. |
| 145 | 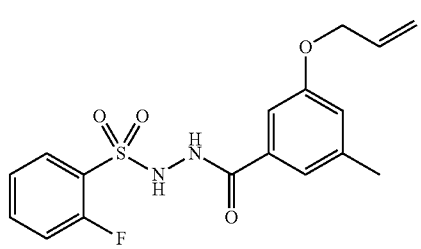 [SMILES: C=CCOc1cc(C)cc(C(=O)NNS(=O)(=O)c2ccccc2F)c1] | B | White solid (0.106 g, 37% yield). $^1$H NMR (400 MHz, DMSO) δ 10.51 (s, 1H), 10.10 (s, 1H), 7.86 (d, J = 7.4 Hz, 2H), 7.64 (t, J = 7.4 Hz, 1H), 7.56 (t, J = 7.6 Hz, 2H), 7.01 (dd, J = 5.6, 3.1 Hz, 1H), 6.75-6.57 (m, 1H), 6.01 (ddd, J = 22.4, 10.4, 5.2 Hz, 1H), 5.37 (dd, J = 17.3, 1.6 Hz, 1H), 5.26 (dd, J = 10.5, 1.4 Hz, 1H), 4.53 (d, J = 5.1 Hz, 2H), 2.19 (s, 3H). LCMS B rt 3.66 min, m/z 365.2 [M + H]$^+$. |

| | Structure | M | Product details |
|---|---|---|---|
| 146 | 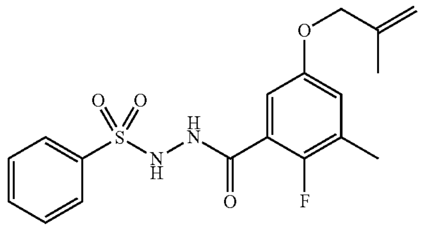 [SMILES: C=C(C)COc1cc(C)c(F)c(C(=O)NNS(=O)(=O)c2ccccc2)c1] | B | White solid (0.021 g, 68% yield). $^1$H NMR (400 MHz, DMSO) δ 10.51 (d, J = 3.0 Hz, 1H), 10.10 (d, J = 3.0 Hz, 1H), 7.86 (d, J = 7.4 Hz, 2H), 7.64 (t, J = 7.3 Hz, 1H), 7.56 (t, J = 7.5 Hz, 2H), 7.01 (d, J = 1.9 Hz, 1H), 6.77-6.56 (m, 1H), 4.99 (d, J = 28.4 Hz, 2H), 4.43 (s, 2H), 2.19 (s, 3H), 1.75 (s, 3H). LCMS B rt 3.72 min, m/z 379.2 [M + H]$^+$. |

Compound 147 was made by analogous methods:

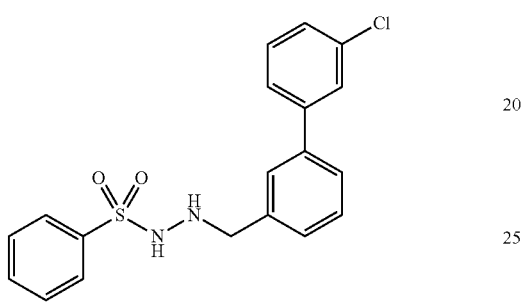

Commercial Compounds

| | Structure | Supplier |
|---|---|---|
| 148 | 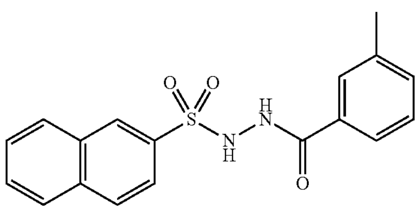 [SMILES: Cc1cccc(C(=O)NNS(=O)(=O)c2ccc3ccccc3c2)c1] | Princeton BioMolecular Research |
| 149 | 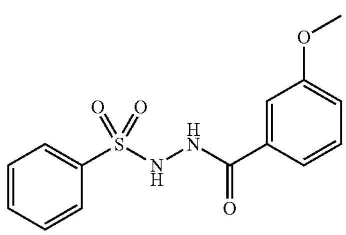 | Chembridge |

Example 5

(a) N'-(2-Fluoro-5-(furan-2-yl)-3-methylbenzoyl)benzenesulfonohydrazide (152)

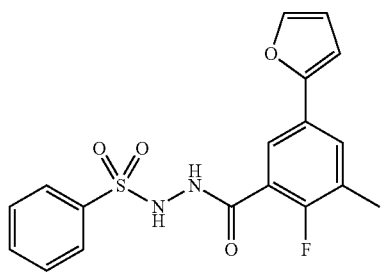 [SMILES: Cc1cc(-c2ccco2)cc(C(=O)NNS(=O)(=O)c2ccccc2)c1F]

2-Fluoro-5-(furan-2-yl)-3-methylbenzoic acid (I15) (0.045 g, 0.204 mmol), benzenesulfonyl hydrazide (0.044 g, 0.255 mmol), HOAt (0.035 g, 0.255 mmol) and EDCI.HCl (0.049 g, 0.255 mmol) were dissolved in MeCN (3 mL), under an atmosphere of nitrogen. The solution was heated to 40° C. and allowed to stir for 17 h, upon which the reaction was cooled, concentrated in vacuo, then loaded directly onto silica for purification. The crude material was purified by silica gel chromatography (Isolera Biotage, 12 g Si Cartridge, 0-60% EtOAc in petroleum benzine 40-60° C.) with the fractions containing suspected product collected and concentrated in vacuo, to yield the title compound (0.018 g, 24% yield) as a white solid.

$^1$H NMR (400 MHz, DMSO) δ 10.63 (d, J=3.3 Hz, 1H), 10.17 (d, J=3.3 Hz, 1H), 7.90-7.86 (m, 2H), 7.77 (dd, J=1.7, 0.7 Hz, 1H), 7.75 (dd, J=6.4, 2.0 Hz, 1H), 7.66 (tt, J=6.6, 6.6, 1.3, 1.3 Hz, 1H), 7.61-7.54 (m, 2H), 7.45 (dd, J=6.0, 2.2 Hz, 1H), 6.95 (dd, J=3.4, 0.8 Hz, 1H), 6.60 (dd, J=3.4, 1.8 Hz, 1H), 2.27 (d, J=2.0 Hz, 3H). LCMS B rt. 3.692 min, m/z 375.1 [M+H]+.

(b) 2-Fluoro-N'-(3-(furan-2-yl)-5-methylbenzoyl)benzenesulfonohydrazide (153)

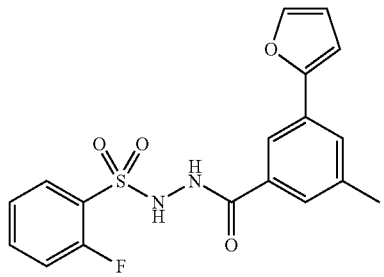 [SMILES: Cc1cc(C(=O)NNS(=O)(=O)c2ccccc2F)cc(-c2ccco2)c1]

3-(Furan-2-yl)-5-methylbenzoic acid (I14) (0.045 g, 0.223 mmol), 2 fluorobenzenesulfonyl hydrazide (0.053 g, 0.278 mmol), HOAt (0.038 g, 0.278 mmol) and EDCI.HCl (0.053 g, 0.278 mmol) were dissolved in MeCN (3 mL) under an atmosphere of nitrogen. The solution was heated to 40° C. and allowed to stir for 17 h, upon which the reaction was cooled, concentrated in vacuo, then loaded directly onto silica for purification. The crude material was purified by silica gel chromatography (Isolera Biotage, 12 g Si Cartridge, 0-60% EtOAc in petroleum benzine 40-60° C.) with the fractions containing suspected product collected and concentrated in vacuo, to yield the title compound (0.020 g, 24% yield) as a white solid.

$^1$H NMR (400 MHz, DMSO): δ 10.77 (d, J=2.7 Hz, 1H), 10.30 (d, J=2.7 Hz, 1H), 7.84-7.76 (m, 3H), 7.72-7.65 (m, 2H), 7.43-7.37 (m, 2H), 7.30 (td, J=7.6, 7.6, 1.1 Hz, 1H), 6.98-6.96 (m, 1H), 6.61 (dd, J=3.4, 1.8 Hz, 1H), 2.35 (s, 3H). LCMS B rt 3.70 min, m/z 373.0 [M−H]−.

Example 6—Moz Biochemical Assay

Compounds of the invention may be tested for in vitro activity in the following assay: Active Moz protein was expressed as N-terminal fusion protein with a His$_6$ tag in BL21 E. coli cells. Protein purification was performed via nickel-immobilized metal ion affinity chromatography followed by gel filtration. To determine the inhibition of Moz activity by the test compounds, assay reactions were conducted in a volume of 8 μL in 384-well low volume assay plates. The reactions were performed in assay buffer (100 mM Tris-HCl, pH 7.8, 15 mM NaCl, 1 mM EDTA, 0.01% Tween-20, 1 mM Dithiothreitol, and 0.02% m/v chicken egg white albumin). Reactions were set up with 0.4 μM Acetyl coenzyme A (AcCoA), 50 nM N-terminal histone H4 peptide (sequence SGRGKGGKGLGKGGAKRHRKV-GGK-biotin), 10 nM MOZ enzyme, and an acetyl-lysine specific antibody (final dilution 1:10000). 11-point dilution series of the compounds of the invention were prepared in DMSO; a volume of 100 nL was transferred using a pin tool into assay plates containing substrates, before adding enzyme to start the reaction. Positive (no compound) and negative (AcCoA omitted) control reactions were included on the same plates and received the same amount of DMSO as the compound treated wells. After adding all reagents, the plates were sealed with adhesive seals and incubated for 90 minutes at room temperature. An additional 4 μL of assay buffer containing AlphaScreen® Protein A acceptor beads and Streptavidin donor beads (PerkinElmer, Waltham, Mass.) to a final concentration of 4 μg/mL was then added. After incubation for 2 hours the plates were read using an EnVision 2103 multi label plate reader (PerkinElmer) in HTS AlphaScreen® mode. IC$_{50}$ values were obtained from the raw readings by calculating percent inhibition (%I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC$_{50}$ value, and D is the slope.

Results

| | IC$_{50}$ (μM) |
|---|---|
| 1 | 2.951 |
| 2 | 0.287 |
| 3 | 7.795 |
| 4 | 0.195 |
| 5 | 0.123 |
| 6 | 2.044 |
| 7 | 7.438 |
| 8 | 0.162 |
| 9 | 0.449 |
| 10 | 6.865 |
| 11 | 0.475 |
| 12 | 125.000 |
| 13 | 0.998 |
| 14 | 0.470 |
| 15 | 3.173 |
| 16 | 1.672 |
| 17 | 3.789 |
| 18 | 0.432 |
| 19 | 2.436 |
| 20 | 0.378 |
| 21 | 2.353 |
| 22 | 8.465 |
| 23 | 0.406 |
| 24 | 0.139 |
| 25 | 3.834 |
| 26 | 40.034 |
| 27 | 11.242 |
| 28 | 3.215 |
| 29 | 0.548 |
| 30 | 0.721 |
| 31 | 8.549 |
| 32 | 25.807 |
| 33 | 0.270 |
| 34 | 8.016 |
| 35 | 0.082 |
| 36 | 0.055 |
| 37 | 85.376 |
| 38 | 0.674 |
| 39 | 0.181 |
| 40 | 0.635 |
| 41 | 0.142 |
| 42 | 0.077 |
| 43 | 0.100 |
| 44 | 0.075 |
| 45 | 0.097 |
| 46 | 0.051 |
| 47 | 0.393 |
| 48 | 0.085 |
| 49 | 0.089 |
| 50 | 0.231 |
| 51 | 0.449 |
| 52 | 0.073 |
| 53 | 0.065 |
| 54 | 0.137 |
| 55 | 0.150 |
| 56 | 1.253 |
| 57 | 0.126 |
| 58 | 0.123 |
| 59 | 0.047 |
| 60 | 0.062 |
| 61 | 0.097 |
| 62 | 1.174 |
| 63 | 0.097 |
| 64 | 0.070 |
| 65 | 0.440 |
| 66 | 0.120 |
| 67 | 0.060 |

|     | IC$_{50}$ (µM) |
| --- | --- |
| 68  | 0.153 |
| 69  | 0.068 |
| 70  | 0.203 |
| 71  | 0.078 |
| 72  | 0.426 |
| 73  | 0.411 |
| 74  | 0.552 |
| 75  | 0.094 |
| 76  | 0.119 |
| 77  | 0.303 |
| 78  | 0.122 |
| 79  | 0.084 |
| 80  | 0.126 |
| 81  | 0.748 |
| 82  | 0.221 |
| 83  | 0.331 |
| 84  | 0.058 |
| 85  | 0.087 |
| 86  | 0.091 |
| 87  | 0.041 |
| 88  | 0.054 |
| 89  | 0.140 |
| 90  | 0.116 |
| 91  | 0.060 |
| 92  | 0.106 |
| 93  | 0.084 |
| 94  | 0.061 |
| 95  | 0.050 |
| 96  | 0.093 |
| 97  | 0.091 |
| 98  | 13.148 |
| 99  | 63.672 |
| 100 | 0.144 |
| 101 | 0.066 |
| 102 | 0.478 |
| 103 | 0.109 |
| 104 | 0.106 |
| 105 | 0.093 |
| 106 | 18.961 |
| 107 | 1.915 |
| 108 | 125.000 |
| 109 | 21.345 |
| 110 | 2.592 |
| 111 | 0.072 |
| 112 | 0.422 |
| 113 | 0.052 |
| 114 | 0.064 |
| 115 | 4.623 |
| 116 | 16.622 |
| 117 | 4.550 |
| 118 | 0.488 |
| 119 | 10.491 |
| 120 | 0.126 |
| 121 | 0.117 |
| 122 | 0.966 |
| 123 | 0.093 |
| 124 | 0.066 |
| 125 | 0.437 |
| 126 | 0.176 |
| 127 | 0.675 |
| 128 | 0.558 |
| 129 | 0.077 |
| 130 | 0.120 |
| 131 | 0.244 |
| 132 | 0.096 |
| 133 | 0.839 |
| 134 | 0.060 |
| 135 | 0.098 |
| 136 | 0.053 |
| 137 | 0.062 |
| 138 | 0.062 |
| 139 | 0.043 |
| 140 | 0.151 |
| 141 | 0.133 |
| 142 | 0.167 |
| 143 | 0.074 |
| 144 | 0.185 |
| 145 | 0.100 |
| 146 | 0.055 |
| 147 | 90.950 |
| 148 | 1.774 |
| 149 | 7.067 |
| 150 | 0.043 |
| 151 | 0.145 |
| 152 | 0.008 |
| 153 | 0.010 |
| 154 | 0.010 |
| 155 | 0.071 |
| 157 | 0.017 |

Example 7—Bioassays for Development of MOZ Specific Inhibitors

Mouse embryonic fibroblasts are isolated from wild type or Moz heterozygous animals and cultured at 3% oxygen/5% carbon dioxide/92% nitrogen. Cells are plated at a density of 1,020 cells/cm$^2$ or 2,040 cells/cm$^2$ or 10,204 cells/cm$^2$. A reference value for MOZ inhibition is generated through comparison with cells with a complete null mutation of MOZ. The absence of a functional Moz gene leads to senescence in 7-14 days at 3% oxygen.

Bioassay 1

Cells are plated in triplicate cultures at 10,204 cells/cm$^2$ in the presence of a test compound. Compounds are tested at 500 nM, 1 µM, 2 µM, 5 µM, 10 µM and 20 µM. Control compounds include those that have a similar structure but show no activity in biochemical assays. After 48 hours, cells are passaged and counted, then replated at 10,204/cm$^2$. This procedure is continued for 336 hours. The total number of cells produced at each passage is then calculated and compared between treatment groups. Cellular senescence is determined by cell cycle arrest, i.e. reduced incorporation of BrdU, reduced level of Ki67 staining and flow cytometric analysis of DNA content, combined with increased expression of β-galactosidase (determined after 384 hours), likewise determined by flow cytometry. Cells are analysed by flow cytometry for the absence of markers of apoptosis by staining with propidium iodide and FITC-conjugated annexin V. The level of DNA damaged is assessed by γH2A.X staining, a marker of DNA strand breaks. Moz heterozygous cells are used to demonstrate that the primary effect of the active compounds is on-target by demonstrating that Moz heterozygous cells have an increased sensitivity to active inhibitors.

Bioassay 2

Cells are plated in triplicate at 2,040 cells/cm$^2$ in the presence of a test compound. Compounds are tested at 500 nM, 1 µM, 2 µM, 5 µM, 10 µM and 20 µM. Control compounds include those that have a similar structure but show no activity in biochemical assays. Cells are grown for 144 hours then harvested for RNA purification or chromatin immunoprecipitation assays. RT-qPCR is used to assay the levels of MOZ target genes Ink4a, ink4b, Arf, Cdc6, Cdca8, Cdca2, E2f2, Ezh2, Skp2 and Melk. Chromatin immunoprecipitation is used to demonstrate that the target of MOZ acetyltransferase activity, histone 3 lysine 9 acetylation, is reduced, but that histone 3 lysine 14 acetylation, which is not a MOZ target, is not affected.

Bioassay 3

Cells are plated in triplicate at 1,020 cells/cm2 in the presence of a test compound. Compounds are tested at 500 nM, 1 µM, 2 µM, 5 µM, 10 µM and 20 µM. Control compounds include those that have a similar structure but show no activity in biochemical assays. Cells are grown for 144 hours then harvested for assessment of population doublings and percentage of dead cells.

Bioassay 4

To test if cells expressing mutant forms of RAS sensitized to senescence induction, MOZ inhibitors were combined with the ectopic expression of KRASG12V. Cells are plated in triplicate cultures at 10,204 cells/cm2 then transfected with control retroviral vectors pBABE or pBABE containing a mutant KrasG12V expression cassette. Cultures were maintained at 3% O2. Selection for transfected cells is achieved using puromycin. Compounds are tested at 0 µM 1 µM, 2.5 µM, and 5 µM. After 48 hours, cells are passaged and counted, then replated at 10,204/cm2. This procedure is continued for 336 hours. The total number of cells produced at each passage is then calculated and compared between treatment groups. Cellular senescence is determined by cell cycle arrest. Comparisons are between cells treated with vehicle only expressing the control vector, cells treated with 5 µM expressing the control vector (concentration shown in bioassay 1 to produce cellular senescence) and cells treated with 0 uM 1 µM, 2.5 µM, and 5 µM expressing the KrasV12 expressing vector vector Bioassay 5

Using a loss of function mutation in MOZ (KAT6a) we have demonstrated that MOZ is required for proliferation of B cells and that even heterozygous loss of MOZ delays onset of lymphoma 3.9 fold. (Sheikh et al 2015b). Therefore the agents disclosed herein may be useful in preventing relapse of patients in remission after standard treatments or in combination with standard treatments, since inhibition of proliferation of the target progenitor or stem cell may reduce the probability of acquiring additional mutations that would otherwise enhance the cancer phenotype.

Pro-B cells are purified by positive selection using antiCD19-magnetic beads and fluorescence activated cell sorting using the criterion: cell surface expression of B220, CD19 and cKit but not IgM. After purification, 25,000 pro-B cells are seeded onto 3.5 cm culture dishes plate containing methylcellulose (MethoCult M3630, STEM CELL technologies) for 7 days. After 7 days culture, colonies in which there were more than 50 cells are counted. Subsequently, 190,000 pro-B cells are replated into methylcellulose for another 7 days of culture, followed by enumeration. Wild type or Eµ-Myc pre-leukemia pre B cells are treated with vehicle (DMSO), compound 108 or compound 36 at various concentrations Bioassay 6

Pre B cells are isolated from bone marrow according to the criterion: cell surface expression of B220, CD19, but not cKit or IgM. Proliferation curves of wild type pre-B cells and Ep-Myc pre-leukemia pre B cells are generated by counting cells cultured on OP9 cell feeder layer in the presence of the growth factor IL-7. Media is changed every two days and cells are passaged every 4 days. Wild type or Ep-Myc pre-leukemia pre B cells are treated with vehicle (DMSO), inactive compound or active compounds at various concentrations Bioassay 7

Pre B cells are isolated from bone marrow according to the criterion: cell surface expression of B220, CD19, but not cKit or IgM. Pre-B cells are cultured on OP9 cells with IL7 in the presence of compounds at concentrations from 0.01 µM to 20 µM in vitro for 4 days. Cell number is then enumerated and an IC50 is calculated.

Bioassay 8

Pre B cells are isolated from bone marrow according to the criterion: cell surface expression of B220, CD19, but not cKit or IgM. Pre-B cells are cultured on OP9 cells with IL7 in the presence of compounds at various concentrations. The stages of the cell cycle in cultured pre-B cells with and without treatment is analysed by flow cytometry using a stain for DNA content combined with the cell cycle marker Ki67 to enumerate the proportion of cells in different phases of the cell cycle.

Bioassay 9

Pre B cells are isolated from bone marrow according to the criterion: cell surface expression of B220, CD19, but not cKit or IgM. Pre-B cells are cultured on OP9 cells with IL7 in the presence of compounds at various concentrations. The stages of the cell cycle in pre-B cells with and without treatment is analysed using flow cytometry to assay, using a stain for DNA content combined with BrdU to determine the proportion of cells in S phase.

Bioassay 10

Mice were treated with compounds at the dosage of 50 mg/kg by I.P injection. Compounds are prepared for injection as a slurry in 50% PEG400/H2O. The effect on the B cell lineage is determined by fluorescent cytometry using characteristic cell surface markers expressed at different stages of B cell development.

Results

Bioassay 1

Testing compound 36 in Bioassay 1 allows calculation of a dose at which 50% senescence occur (IC50).

| | IC50 (µM) | $R^2$ |
|---|---|---|
| 36 | 1.600 | 0.965 |

An end point of cellular senescence was confirmed at doses of 5 µM, 10 µM and 20 µM by the absence of proliferation, cellular morphology and up regulation of β-galactosidase by 186% (5 µM) 195% (10 µM) and 185% (20 µM) at 384 hours after plating, which is equivalent to the effect of genetic deletion of MOZ. The mechanism of action of these compounds, i.e. causing cell cycle arrest and senescence, was confirmed by repeating this assay using cells in which the INK4a/ARF pathways was inactivated by genetic deletion of a key exon common to both INK4a and the alternative splice product of the CDKN2a locus ARF. In the absence of INK4a and ARF cells cannot undergo senescence and no inhibition of cell proliferation was detected when INK4a and ARF null cells were treated with compound 37 at 1 µM, 2 µM, 5 µM, 10 µM, or the control compound.

Bioassay 2

Four active compounds tested using Bioassay 2. Treatment of cells at a does of 5 µM showed a reduction of mRNA coding for the MOZ regulated gene Cdc6. The reduction in gene expression, compared to vehicle, is similar to that observed in the genetic knock out of MOZ function.

| | CDC6 mRNA % control [5 µM] |
|---|---|
| 36 | 65.1% |
| 137 | 67.5% |
| 64 | 60.9% |
| 53 | 62.8% |

Bioassay 3

Testing compounds in Bioassay 3 allows calculation of a dose at which cell proliferation is inhibited 50% (IC50).

| | $IC_{50}$ (µM) | $R^2$ |
|---|---|---|
| 36 | 0.551 | 0.995 |
| 137 | 1.168 | 0.870 |
| 120 | 0.651 | 0.984 |
| 58 | 0.481 | 0.995 |

| | IC$_{50}$ (µM) | R$^2$ |
|---|---|---|
| 64 | 0.992 | 0.985 |
| 53 | 0.635 | 0.958 |
| 88 | 1.257 | 0.706 |
| 87 | 0.614 | 0.941 |

Bioassay 4

Compound 36 treatment of mouse embryonic fibroblasts shows a dose dependent decrease in cell number in the presence of mutant KRas (KrasG12).

| Treatment | | 0 h | Cumulative Cell Counts | | | |
|---|---|---|---|---|---|---|
| | | | 96 h | 168 h | 264 h | 336 h |
| pBABE | vehicle | 100000 | 216666.7 | 362666.7 | 681866.7 | 1033253 |
| | 5 µm | 100000 | 198333.3 | 233500 | 300666.7 | 226600 |
| KrasG12V | vehicle | 100000 | 136666.7 | 157166.7 | 266316.7 | 180760 |
| KrasG12V | 1 µm | 100000 | 128333.3 | 129833.3 | 145100 | 132000 |
| KrasG12V | 2.5 µm | 100000 | 141666.7 | 121666.7 | 101433.3 | 94133.33 |
| KrasG12V | 5 µm | 100000 | 126666.7 | 106166.7 | 81641.67 | 50940 |
| pBABE S.E.M | vehicle | 0 | 11155.47 | 26831.16 | 60355.8 | 284707.7 |
| | 5 µm | 0 | 12224.75 | 14430.87 | 40846.96 | 38168.57 |
| KrasG12V S.E.M | vehicle | 0 | 4944.132 | 11816.42 | 44086.33 | 14682.29 |
| | 1 µm | 0 | 6009.252 | 5393.927 | 9436.631 | 7937.254 |
| | 2.5 µm | 0 | 9098.229 | 7666.667 | 11683.2 | 20231.06 |
| | 5 µm | 0 | 9189.366 | 11417.58 | 10548.07 | 7294.628 |

Bioassay 5

Enumeration of FACs-purified pro-B cell colonies in methylcellulose culture subjected to inhibitor treatment. The active compound 36 greatly inhibits colony formation as compared to vehicle or inactive compound 108. Compound 36 is equally effective in inhibiting proliferation and secondary colony formation of cells expressing the oncogene cMyc.

| | colony number | S.E.M |
|---|---|---|
| Treatment wild type pro-B cells | | |
| DMSO(n = 4) | 247.125 | 4.7 |
| 1 µM Compound 108 (n = 4) | 245.125 | 6.4 |
| 1 µM Compound 36 (n = 4) | 161.25 | 7.2 |
| Treatment Eµ-Myc pre-leukemia pro-B cells | | |
| DMSO(n = 4) | 177.5 | 5.0 |
| 1 µM Compound 108 (n = 4) | 180.5 | 7.0 |
| 1 µM Compound 36 (n = 4) | 104.625 | 2.4 |

| | colony number | S.E.M |
|---|---|---|
| Treatment wild type pro-B cells secondary colony formation | | |
| DMSO vehicle (n = 4) | 76.375 | 2.9 |
| 1 µM Compound 108 (n = 4) | 77 | 1.9 |
| 1 µM Compound 36 (n = 4) | 12.25 | 1.7 |

-continued

| | colony number | S.E.M |
|---|---|---|
| Treatment Eµ-Myc pre-leukemia pro-B cells secondary colony formation | | |
| DMSO vehicle (n = 4) | 78.375 | 2.3 |
| 1 µM Compound 108 (n = 4) | 78 | 1.7 |
| 1 µM Compound 36 (n = 4) | 9.75 | 0.9 |

Bioassay 6

The proliferation wild type and pre-leukaemic B cell progenitors is inhibited with active compound 36 compared to vehicle. Results are presented as cumulative average cell number with the S.E.M tabulated below.

| Treatment | Day 0 | Day 4 | Day 8 | Day 12 |
|---|---|---|---|---|
| | Wild type pre B cells- cell count | | | |
| Vehicle (n = 3) | 15000 | 65777 | 2212281 | 8768019 |
| 10 µM Compound 36 (n = 3) | 15000 | 26111 | 8192 | 0.000 |
| 5 µM Compound 36 (n = 3) | 15000 | 32555 | 19925 | 0.000 |
| 1 µM Compound 36 (n = 3) | 15000 | 54333 | 73474 | 15097 |
| | Wild type pre B cells S.E.M | | | |
| Vehicle (n = 3) | 0 | 3045 | 245283 | 1710161 |
| 10 µM Compound 36 (n = 3) | 0 | 3045 | 440 | 0.000 |
| 5 µM Compound 36 (n = 3) | 0 | 1637 | 739 | 0.000 |
| 1 µM Compound 36 (n = 3) | 0 | 1953 | 10515 | 12912 |

-continued

| Treatment | Day 0 | Day 4 | Day 8 | Day 12 | Day 16 |
|---|---|---|---|---|---|
| Eµ-Myc pre-leukemia pre-B cells- cell count | | | | | |
| Vehicle (n = 3) | 100000 | 449444 | 4859277 | 20013531 | 526508291 |
| 5 µM Compound 36 (n = 3) | 100000 | 79444 | 33236 | 0 | 0 |
| 1 µM Compound 36 (n = 3) | 100000 | 172777 | 135815 | 29983 | 0 |
| 0.2 µM Compound 36 (n = 3) | 100000 | 373055 | 1110631 | 464403 | 81501 |
| Eµ-Myc pre-leukemia pre-B cells- SEM | | | | | |
| Vehicle (n = 3) | 0 | 15880 | 221940 | 2045775 | 7840593 |
| 5 µM Compound 36 (n = 3) | 0 | 4747 | 2866 | 0 | 0 |
| 1 µM Compound 36 (n = 3) | 0 | 17148 | 4295 | 2614 | 0 |
| 0.2 µM Compound 36 (n = 3) | 0 | 11142 | 63477 | 99859 | 46278 |

Bioassay 7

Dose response wild type and pre B cells treated with different concentrations of active compound 36 and inactive but structurally similar compound 108. Note that compound 36 is effective in suppression of pre B cell proliferation even when these cells express the cMyc oncogene at high levels, whereas inactive compound 108 has no effect.

| Cells | Compound | IC50 µM |
|---|---|---|
| wild type Pre B cells | Compound 36 | 0.364 |
| Eµ-Myc pre-leukemia pre B cells | Compound 36 | 0.421 |
| wild type Pre B cells | Compound 108 | $2.45e^{-10}$ |

Bioassay 8

Cell cycle analysis of wild type pre-B cells treated with compound 36 or inactive compound compound 108. The number of cells in S phase was down-regulated by 40 percent in wild type pre-B cells after compound 36 treatment. Four biological replicates for each treatment were performed.

Data are presented as mean±s.e.m.

| Treatment | G0 | G1 | S | G2/M | S.E.M. G0 | S.E.M.G1 | S.E.M. S | S.E.M. G2/M |
|---|---|---|---|---|---|---|---|---|
| Cell cycle analysis of wild type pre B cells cultured for 4 days | | | | | | | | |
| Vehicle (n = 4) | 10.5% | 52.3% | 25.0% | 11.6% | 0.007 | 0.009 | 0.008 | 0.003 |
| 1 µM Compound 108 (n = 4) | 10.8% | 53.7% | 23.6% | 12.1% | 0.014 | 0.014 | 0.006 | 0.005 |
| 1 µM Compound 36 (n = 4) | 14.5% | 55.9% | 15.6% | 12.7% | 0.013 | 0.006 | 0.005 | 0.003 |
| Cell cycle analysis of wild type pre B cells cultured for 6 days | | | | | | | | |
| Vehicle (n = 4) | 7.8% | 62.9% | 15.0% | 7.5% | 1.1% | 1.3% | 0.6% | 0.2% |
| 1 µM Compound 108 (n = 4) | 8.6% | 62.0% | 14.7% | 8.5% | 0.9% | 0.9% | 0.7% | 0.4% |
| 1 µM compound 36 (n = 4) | 11.0% | 66.6% | 8.3% | 9.0% | 1.5% | 1.2% | 0.8% | 0.3% |

Bioassay 9

Cell cycle analysis of wild type pre-B cells treated with compound 36 or inactive compound compound 108 using the S-phase marker BrdU. Note that treatment with the active compound 36 treatment leads to a reduction of cells in S-phase and a corresponding increase in cells in G0/G1. Three biological replicates for each treatment were performed.

| Treatment | G0/G1 | S | G2/M |
|---|---|---|---|
| vehicle (n = 3) | 42.7 | 44.0 | 6.8 |
| 1 µM Compound 108 (n = 3) | 44.2 | 46.2 | 5.2 |
| 1 µM Compound 36 (n = 3) | 54.9 | 32.7 | 5.5 |

Bioassay 10.

Treatment of mice with active compounds 46 and 137 displayed markedly reduced numbers of pre B cells in the bone marrow after daily I.P. injection. This result is similar to the suppression of pre B cell numbers seen after ablation of the Moz gene providing evidence of an on-target effect in vivo.

| | Wild type mice treated with compound daily, data are percentage of WBC per femur | | | |
|---|---|---|---|---|
| Treatment | pro-B cells | pre-B cells | immature B cells | mature B cells |
| vehicle (n = 3) | 1.66% | 21.66% | 4.40% | 2.82% |
| Compound 46 (n = 3) | 1.14% | 10.59% | 3.33% | 3.65% |

-continued

| | Wild type mice treated with compound daily, data are percentage of WBC per femur | | | |
|---|---|---|---|---|
| Treatment | pro-B cells | pre-B cells | immature B cells | mature B cells |
| Compound 137 (n = 3) | 1.01% | 12.71% | 3.92% | 3.16% |

REFERENCES

| | |
|---|---|
| Andreeff et al., 2008 | Andreeff, M., Ruvolo, V., Gadgil, S., Zeng, C., Coombes, K., Chen, W., Kornblau, S., Barón, A. E., and Drabkin, H. A. *Leukemia* 22(11): 2041-2047 (2008) |
| Berndsen et al., 2007 | C. E. Berndsen, B. N. Albaugh, S. Tan et al., *Biochemistry* 46 (3), 623 (2007) |
| Borrow et al., 1996 | J. Borrow, VP Jr. Stanton, J M. Andresen et al., *Nat. Genet.* 14, 33 (1996) |
| Cortes et al., 2004 | J. Cortes, S. O'Brien, and H. Kantarjian, *Blood* 104 (7), 2204 (2004) |
| Decker et al., 2008 | P. V. Decker, D. Y. Yu, M. Iizuka et al., *Genetics* 178 (3), 1209 (2008) |
| Gervais et al., 2008 | C. Gervais, A. Murati, C. Helias et al., *Leukemia* (2008) |
| Huntly et al., 2004 | B. J. Huntly, H. Shigematsu, K. Deguchi et al., *Cancer Cell* 6 (6), 587 (2004) |
| Ichikawa et al., 2004 | M. Ichikawa, T. Asai, T. Saito et al., *Nat Med* 10 (3), 299 (2004) |
| Jemal et al 2002 | A. Jemal, A. Thomas, T. Murray et al., *CA Cancer J Clin* 52 (1), 23 (2002) |
| Li et al., 2006 | H. Li, S. Ilin, W. Wang et al., *Nature* 442 (7098), 91 (2006); J. Wysocka, T. Swigut, H. Xiao et al., *Nature* 442 (7098), 86 (2006); X. Shi, T. Hong, K. L. Walter et al., *Nature* 442 (7098), 96 (2006) |
| Merson et al., 2006 | T. D. Merson, M. P. Dixon, C. Collin et al., *J Neurosci* 26 (44), 11359 (2006) |
| Moen et al., 2007 | M. D. Moen, K. McKeage, G. L. Plosker et al., *Drugs* 67 (2), 299 (2007) |
| Murati et al., 2009 | Murati, A., Gervais, C., Carbuccia, N., Finetti, P., Cervera, N., Adélaïde, J., Struski, S., Lippert, E., Mugneret, F., Tigaud, I. et al. *Leukemia* 23(1): 85-94 (2009) |
| Panagopoulos et al., 2001 | I. Panagopoulos, T. Fioretos, M. Isaksson et al., *Hum Mol Genet* 10 (4), 395 (2001) |
| Pelletier et al., 2003 | N. Pelletier, N. Champagne, H. Lim et al., *Methods* 31 (1), 24 (2003) |
| Perez-Campo et al., 2009 | Perez-Campo, F. M., Borrow, J., Kouskoff, V., and Lacaud, G. *Blood* 113(20): 4866-4874 (2009) |
| Shah and Sukumar 2010 | Shah, N. and Sukumar, S. *Nat Rev Cancer* 10(5): 361-371 (2010) |
| Sheikh et al., 2015a | Sheikh B N, Phipson B., El-Saafin F Vanyai H K, Downer N L, Bird M J, Kueh A J, May R E, Smyth G K, Voss A K*, Thomas T*. (2015). Moz (MYST3, KAT6a) inhibitis senescence via the INK4A-ARF pathway. Oncogene 34: 5807. |
| Sheikh et al., 2015b | Sheikh B N, Lee S C, El-Saafin F, Vanyai H K, Hu Y, Pang S H, Grabow S, Strasser A, Nutt S L, Alexander W S, Smyth G K, Voss A K*, Thomas T*. (2015) MOZ regulates B cell progenitors and, consequently, Moz haploinsufficiency dramatically retards MYC-induced lymphoma development. Blood. 125: 1910. |
| Stark et al., 1995 | B. Stark, P. Resnitzky, M. Jeison et al., *Leuk Res* 19 (6), 367 (1995) |
| Thomas et al., 2000 | T. Thomas, A. K. Voss, K. Chowdhury et al., *Development* 127 (12), 2537 (2000) |
| Thomas et al., 2006 | T. Thomas, L M. Corcoran, R. Gugasyan et al., *Genes Dev* 20 (9), 1175 (2006) |
| Thomas et al., 2007 | T. Thomas and A. K. Voss, *Cell Cycle* 6 (6), 696 (2007) |
| Vizmanos et al. 2003 | Vizmanos, J. L., Larráyoz, M. J., Lahortiga, I., Fioristán, F., Alvarez, C., Odero, M. D., Novo, F. J., and Calasanz, M. J. *Genes Chromosomes Cancer* 36(4): 402-405 (2003) |
| Zeisig et al., 2004 | Zeisig, B. B., Milne, T., García-Cuéllar, M. P., Schreiner, S., Martin, M. E., Fuchs, U., Borkhardt, A., Chanda, S. K., Walker, J., Soden, R. et al. *Mol Cell Biol* 24(2): 617-628 (2004) |

The invention claimed is:

1. A compound of formula I:

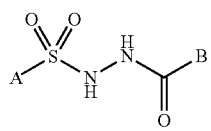

(I)

wherein:

A is selected from the group consisting of:

(i)

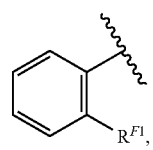

wherein $R^{F1}$ is H or F;

(ii)

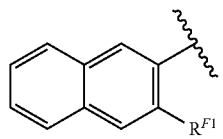

wherein $R^{F1}$ is H or F; and
(iii) a N-containing $C_6$ heteroaryl group; and
B is

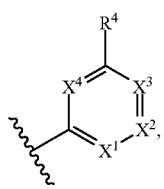

wherein $X^1$ is either $CR^{F2}$ or N, wherein $R^{F2}$ is H or F; $X^2$ is either $CR^3$ or N, wherein $R^3$ is selected from the group consisting of H, Me, Cl, F, and OMe; $X^3$ is CH; $X^4$ is either $CR^{F3}$ or N, wherein $R^{F3}$ is H or F; wherein only one or two of $X^1$, $X^2$, and $X^4$ may be N; and $R^4$ is selected from the group consisting of optionally substituted phenyl, optionally substituted $C_{5-6}$ heteroaryl; optionally substituted $C_{1-6}$ alkyl and optionally substituted $C_{2-6}$ alkoxy and $OCF_3$, with the proviso that the compound is not P1 or P2:

P1

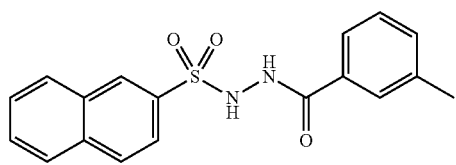

P2

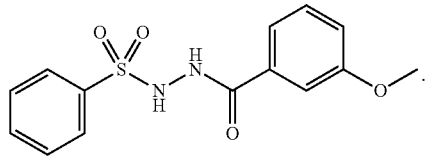

2. The compound according to claim 1, wherein A is:

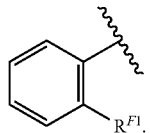

3. The compound according to claim 1, wherein $R^{F1}$ is H.
4. The compound according to claim 1, wherein $R^{F1}$ is F.
5. The compound according to claim 1, wherein none of $X^1$, $X^2$, and $X^4$ are N.
6. The compound according to claim 2, wherein none of $X^1$, $X^2$, and $X^4$ are N, and $R^{F1}$, $R^{F2}$, $R^3$ and $R^{F3}$ are selected from one of the combinations below:

|        | $R^{F1}$ | $R^{F2}$ | $R^3$ | $R^{F3}$ |
|--------|----------|----------|-------|----------|
| (i)    | H        | H        | H     | H        |
| (ii)   | F        | H        | H     | H        |
| (iii)  | H        | H        | H     | F        |
| (iv)   | H        | H        | Cl    | H        |
| (v)    | H        | F        | Cl    | H        |
| (vi)   | F        | H        | Cl    | H        |
| (vii)  | H        | H        | Me    | H        |
| (viii) | H        | F        | Me    | H        |
| (ix)   | F        | H        | Me    | H        |
| (x)    | H        | H        | OMe   | H        |
| (xi)   | F        | H        | OMe   | H        |
| (xii)  | H        | H        | F     | H        |
| (xiii) | F        | H        | F     | H        |

7. The compound according to claim 1, wherein one of $X^1$, $X^2$, and $X^4$ is N.

8. The compound according to claim 1, wherein $R^4$ is unsubstituted phenyl.

9. The compound according to claim 1, wherein $R^4$ is phenyl substituted by a single substituent selected from the group consisting of halo, cyano and $C_{1-4}$ alkoxy.

10. The compound according to claim 9, wherein the substituent is halo and is selected from F and Cl.

11. The compound according to claim 9, wherein the substituent is cyano.

12. The compound according to claim 9, wherein the substituent is methoxy.

13. The compound according to claim 1, wherein $R^4$ is optionally substituted $C_{5-6}$ heteroaryl, and is selected from the group consisting of:

(a) $C_6$ ($N_1$):

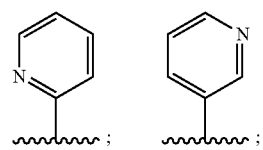 [SMILES: *c1ccccn1 ; *c1cccnc1]

(b) $C_6$ ($N_2$):

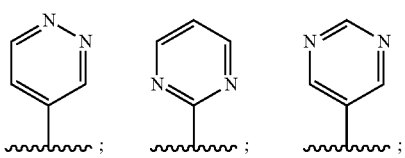 [SMILES: *c1ccnnc1 ; *c1ncccn1 ; *c1cncnc1]

(c) $C_5$ ($O_1$ or $S_1$):

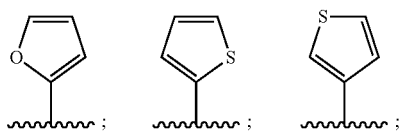

(d) $C_5$ ($N_2$):

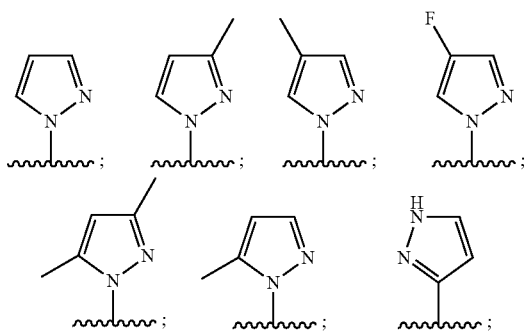

(e) $C_5$ ($N_3$):

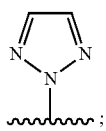

(f) $C_5$ ($N_1S_1$)

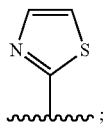

and (g) $C_5$ ($N_2O_1$)

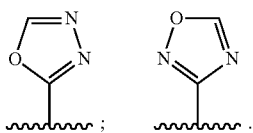

14. The compound according to claim 1, wherein $R^4$ is selected from methyl, ethyl, iso-propyl and $CF_3$.

15. The compound according to claim 1, wherein $R^4$ is selected from the group consisting of:

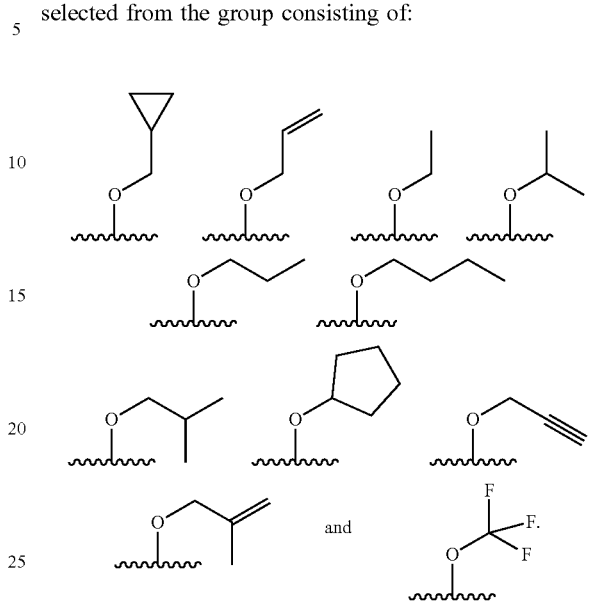

16. A pharmaceutical composition comprising a compound according to claim 1, and a pharmaceutically acceptable excipient.

17. A method of treatment of cancer associated with aberrant proliferation of B cells, comprising administering to a patient in need of treatment, a compound according to claim 1.

18. A method of treatment of a condition ameliorated by the inhibition of MOZ, comprising administering to a patient in need of treatment, a compound according to claim 1.

* * * * *